United States Patent
Kortylewski et al.

(10) Patent No.: US 10,829,765 B2
(45) Date of Patent: Nov. 10, 2020

(54) STAT3 INHIBITORS AND USES THEREOF

(71) Applicant: City of Hope, Duarte, CA (US)

(72) Inventors: Marcin Tomasz Kortylewski, Monrovia, CA (US); Piotr Marek Swiderski, San Dimas, CA (US)

(73) Assignee: CITY OF HOPE, Duarte, CA (US)

( * ) Notice: Subject to any disclaimer, the term of this patent is extended or adjusted under 35 U.S.C. 154(b) by 266 days.

(21) Appl. No.: 15/984,086

(22) Filed: May 18, 2018

(65) Prior Publication Data

US 2018/0312843 A1    Nov. 1, 2018

Related U.S. Application Data

(60) Division of application No. 15/160,865, filed on May 20, 2016, now Pat. No. 9,976,147, which is a continuation of application No. PCT/US2014/066969, filed on Nov. 21, 2014.

(60) Provisional application No. 62/077,035, filed on Nov. 7, 2014, provisional application No. 61/907,953, filed on Nov. 22, 2013.

(51) Int. Cl.
| | |
|---|---|
| C12N 15/117 | (2010.01) |
| C07H 21/02 | (2006.01) |
| A61K 39/39 | (2006.01) |
| C12N 15/11 | (2006.01) |
| A61K 47/54 | (2017.01) |
| C07H 21/04 | (2006.01) |
| A61K 47/64 | (2017.01) |
| A61K 39/00 | (2006.01) |

(52) U.S. Cl.
CPC ............ *C12N 15/117* (2013.01); *A61K 39/39* (2013.01); *A61K 47/549* (2017.08); *A61K 47/64* (2017.08); *C07H 21/02* (2013.01); *C07H 21/04* (2013.01); *C12N 15/111* (2013.01); *A61K 2039/55561* (2013.01); *C12N 2310/13* (2013.01); *C12N 2310/17* (2013.01); *C12N 2310/315* (2013.01); *C12N 2310/351* (2013.01); *C12N 2310/3519* (2013.01); *C12N 2320/30* (2013.01); *C12N 2320/32* (2013.01)

(58) Field of Classification Search
None
See application file for complete search history.

(56) References Cited

U.S. PATENT DOCUMENTS

| 9,976,147 B2 | 5/2018 | Kortylewski et al. |
| 2002/0064515 A1 | 5/2002 | Krieg |
| 2006/0293264 A1 | 12/2006 | Grandis et al. |
| 2012/0065125 A1 | 3/2012 | Yu et al. |
| 2012/0288536 A1 | 11/2012 | Grandis et al. |

OTHER PUBLICATIONS

Pearce et al. "Failure modes in anticancer drug discovery and development" Cancer Drug Design and Discovery, Neidle, ed. Boston: Elsevier (2006) 424-435.*
Gewirtz et al. "Nucleic Acid Therapies: State of the Art and Future Prospects" 92(3) Blood 712-736 (1998).*
Alvarez-Salas "Nucleic Acids as Therapeutic Agents" 8 Current Topics in Medicinal Chemistry 1379-1404 (2008).*
Cameron "Recent Advances in Transgenic Technology" 7 Molcular Biotechnology 253-265 (1997).*
Gura et al. "Systems for Identifying New Drugs Are Often Faulty" 278 Science 1041-1042 (1997).*
Hayun. M. et al. (May 2009). "Induction therapy in a multiple myeloma mouse model using a combination of AS101 and melphalan, and the activity of AS101 in a tumor microenvironment model," *Exp Hematol* 37(5):593-603.
International Search Report dated Nov. 12, 2015, for PCT Application No. PCT/US2014/066969, filed on Nov. 21, 2014, 5 pages.
Kortylewski, M. et al. (Dec. 2005, e-published Nov. 20, 2005). "Inhibiting Stat3 signaling in the hematopoietic system elicits multicomponent antitumor immunity," *Nat Med* 11(12):1314-1321.
Kortylewski, M. et al. (Oct. 2009, e-published Sep. 13, 2009). "TLR agonist-Stat3 siRNA conjugates: cell-specific gene silencing and enhanced antitumor immune responses," *Nat Biotechnol* 27(10):925-932.
Kuo, Y.H. et al. (Jan. 2006). "Cbf β-SMMHC induces distinct abnormal myeloid progenitors able to develop acute myeloid leukemia," *Cancer Cell* 9(1):57-68.
Landrette, S.F. et al. (Apr. 2011, e-published Jan. 25, 2011). "The transcription factor PlagL2 activates Mpl transcription and signaling in hematopoietic progenitor and leukemia cells," *Leukemia* 25(4):655-662.
Leong, P.L. et al. (Apr. 1, 2003, e-published Mar. 14, 2003). "Targeted inhibition of Stat3 with a decoy oligonucleotide abrogates head and neck cancer cell growth," *Proc Natl Acad Sci USA* 100(7):4138-4143.
Written Opinion dated Nov. 12, 2015, for PCT Application No. PCT/US2014/066969, filed on Nov. 21, 2014, 5 pages.
Zhang, Q. et al. (Mar. 31, 2006, e-published Jan. 21, 2016). "Serum-resistant CpG-STAT3 decoy for targeting survival and immune checkpoint signaling in acute myeloid leukemia," *Blood* 127(13):1687-1700.

* cited by examiner

*Primary Examiner* — Nancy J Leith
(74) *Attorney, Agent, or Firm* — Edward D. Grieff; Mintz, Levin, Cohn, Ferris, Glovsky and Popeo, P.C.

(57) ABSTRACT

Described herein, inter alia, are STAT-binding nucleic acids-including compositions and methods of using the same.

20 Claims, 39 Drawing Sheets
Specification includes a Sequence Listing.

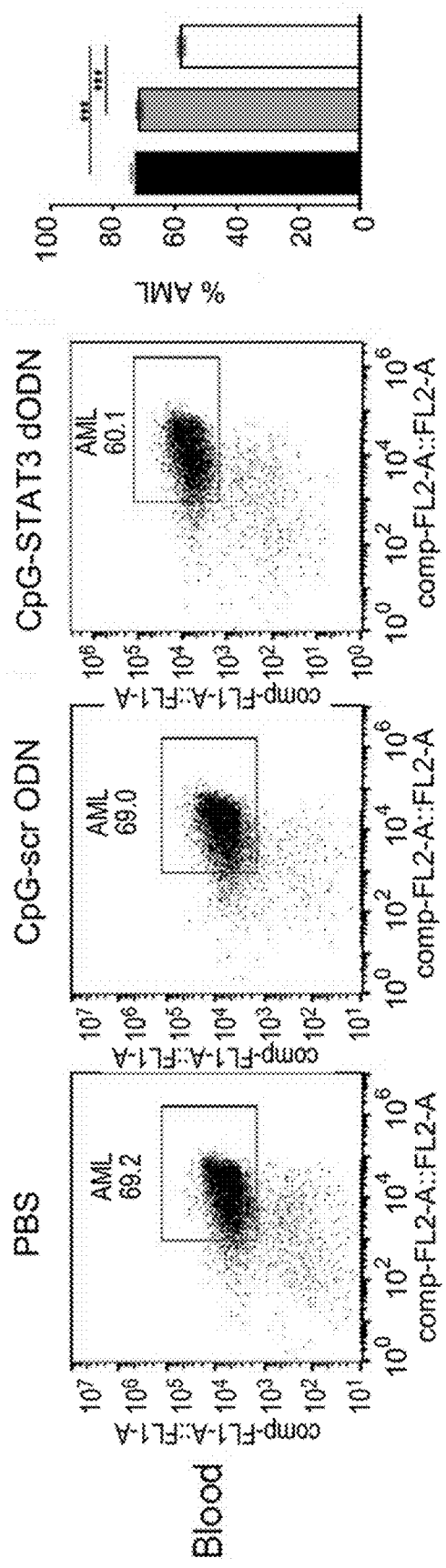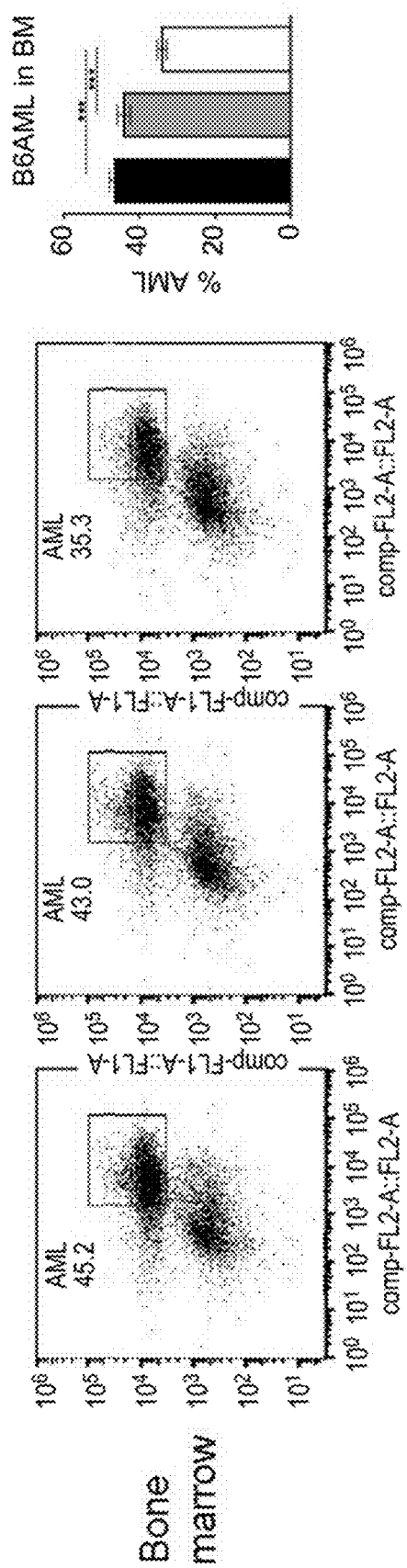
FIG. 21A
FIG. 21B

SEQUENCE LISTING

<160> NUMBER OF SEQ ID NOS: 26

<210> SEQ ID NO 1
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 1
catttcccgt aaatc                                                          15

<210> SEQ ID NO 2
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 2
atttcccgta aat                                                            13

<210> SEQ ID NO 3
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 3
tttcccgtaa a                                                              11

<210> SEQ ID NO 4
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 4 ttcccgtaa                                                                  9

<210> SEQ ID NO 5
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 5 ttccgggaa                                                                  9

<210> SEQ ID NO 6
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Bond to 3'-residue modified to thiophosphate
<220> FEATURE:
<221> NAME/KEY: misc_feature
<222> LOCATION: (16)..(19)
<223> OTHER INFORMATION: Bond to 3'-residue modified to thiophosphate
<220> FEATURE:
<221> NAME/KEY: misc_feature

```
<222> LOCATION: (20)..(20)
<223> OTHER INFORMATION: Bond to 3'-residue modified to
      penta(propylphosphate)
<220> FEATURE:
<221> NAME/KEY: misc_feature
<222> LOCATION: (21)..(23)
<223> OTHER INFORMATION: Bond to 3'-residue modified to thiophosphate
<220> FEATURE:
<221> NAME/KEY: misc_feature
<222> LOCATION: (35)..(35)
<223> OTHER INFORMATION: Bond to 3'-residue modified to
      tetra(propylphosphate)
<220> FEATURE:
<221> NAME/KEY: misc_feature
<222> LOCATION: (47)..(49)
<223> OTHER INFORMATION: Bond to 3'-residue modified to thiophosphate
<220> FEATURE:
<221> NAME/KEY: misc_feature
<222> LOCATION: (50)..(50)
<223> OTHER INFORMATION: 3'-terminal modified to
      tetra(propylphosphate)hexylamine

<400> SEQUENCE: 6
ggtgcatcga tgcagggggg catttcccgt aaatcgattt acgggaaatg          50

<210> SEQ ID NO 7
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Bond to 3'-residue modified to thiophosphate
<220> FEATURE:
<221> NAME/KEY: misc_feature
<222> LOCATION: (16)..(19)
<223> OTHER INFORMATION: Bond to 3'-residue modified to thiophosphate
<220> FEATURE:
<221> NAME/KEY: misc_feature
<222> LOCATION: (20)..(20)
<223> OTHER INFORMATION: Bond to 3'-residue modified to
      hexa(propylphosphate)
<220> FEATURE:
<221> NAME/KEY: misc_feature
<222> LOCATION: (21)..(23)
<223> OTHER INFORMATION: Bond to 3'-residue modified to thiophosphate
<220> FEATURE:
<221> NAME/KEY: misc_feature
<222> LOCATION: (35)..(35)
<223> OTHER INFORMATION: Bond to 3'-residue modified to
      tetra(propylphosphate)
<220> FEATURE:
<221> NAME/KEY: misc_feature
<222> LOCATION: (47)..(49)
<223> OTHER INFORMATION: Bond to 3'-residue modified to thiophosphate
<220> FEATURE:
<221> NAME/KEY: misc_feature
<222> LOCATION: (50)..(50)
<223> OTHER INFORMATION: 3'-terminal modified to
      tetra(propylphosphate)hexylamine

<400> SEQUENCE: 7
ggtgcatgca tgcaggggggg catttcccgt aaatcgattt acgggaaatg          50

<210> SEQ ID NO 8
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
```

```
<223> OTHER INFORMATION: Bond to 3'-residue modified to thiophosphate
<220> FEATURE:
<221> NAME/KEY: misc_feature
<222> LOCATION: (16)..(19)
<223> OTHER INFORMATION: Bond to 3'-residue modified to thiophosphate
<220> FEATURE:
<221> NAME/KEY: misc_feature
<222> LOCATION: (20)..(20)
<223> OTHER INFORMATION: Bond to 3'-residue modified to
      hexa(propylphosphate)
<220> FEATURE:
<221> NAME/KEY: misc_feature
<222> LOCATION: (21)..(23)
<223> OTHER INFORMATION: Bond to 3'-residue modified to thiophosphate
<220> FEATURE:
<221> NAME/KEY: misc_feature
<222> LOCATION: (35)..(35)
<223> OTHER INFORMATION: Bond to 3'-residue modified to
      penta(propylphosphate)
<220> FEATURE:
<221> NAME/KEY: misc_feature
<222> LOCATION: (47)..(49)
<223> OTHER INFORMATION: Bond to 3'-residue modified to thiophosphate
<220> FEATURE:
<221> NAME/KEY: misc_feature
<222> LOCATION: (50)..(50)
<223> OTHER INFORMATION: 3'-terminal modified to
      tetra(propylphosphate)hexylamine

<400> SEQUENCE: 8
ggtgcatcga tgcagggggg actcttgcca attacgtaat tggcaagagt         50

<210> SEQ ID NO 9
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(10)
<223> OTHER INFORMATION: Bond to 3'-residue modified to thiophosphate
<220> FEATURE:
<221> NAME/KEY: misc_feature
<222> LOCATION: (20)..(20)
<223> OTHER INFORMATION: Bond to 3'-residue modified to
      penta(propylphosphate)
<220> FEATURE:
<221> NAME/KEY: misc_feature
<222> LOCATION: (21)..(23)
<223> OTHER INFORMATION: Bond to 3'-residue modified to thiophosphate
<220> FEATURE:
<221> NAME/KEY: misc_feature
<222> LOCATION: (35)..(35)
<223> OTHER INFORMATION: Bond to 3'-residue modified to
      tetra(propylphosphate)
<220> FEATURE:
<221> NAME/KEY: misc_feature
<222> LOCATION: (47)..(49)
<223> OTHER INFORMATION: Bond to 3'-residue modified to thiophosphate
<220> FEATURE:
<221> NAME/KEY: misc_feature
<222> LOCATION: (50)..(50)
<223> OTHER INFORMATION: 3'-terminal modified to
      tetra(propylphosphate)hexylamine

<400> SEQUENCE: 9
tccatgacgt tcctgatgct catttcccgt aaatcgattt acgggaaatg         50

<210> SEQ ID NO 10
<211> LENGTH: 50
<212> TYPE: DNA
<213> ORGANISM: Artificial Sequence
<220> FEATURE:
<223> OTHER INFORMATION: Synthetic polynucleotide
```

```
<220> FEATURE:
<221> NAME/KEY: misc_feature
<222> LOCATION: (1)..(10)
<223> OTHER INFORMATION: Bond to 3'-residue modified to thiophosphate
<220> FEATURE:
<221> NAME/KEY: misc_feature
<222> LOCATION: (20)..(20)
<223> OTHER INFORMATION: Bond to 3'-residue modified to
      penta(propylphosphate)
<220> FEATURE:
<221> NAME/KEY: misc_feature
<222> LOCATION: (21)..(23)
<223> OTHER INFORMATION: Bond to 3'-residue modified to thiophosphate
<220> FEATURE:
<221> NAME/KEY: misc_feature
<222> LOCATION: (35)..(35)
<223> OTHER INFORMATION: Bond to 3'-residue modified to
      tetra(propylphosphate)
<220> FEATURE:
<221> NAME/KEY: misc_feature
<222> LOCATION: (47)..(49)
<223> OTHER INFORMATION: Bond to 3'-residue modified to thiophosphate
<220> FEATURE:
<221> NAME/KEY: misc_feature
<222> LOCATION: (50)..(50)
<223> OTHER INFORMATION: 3'-terminal modified to
      tetra(propylphosphate)hexylamine

<400> SEQUENCE: 10
tccatgacgt tcctgatgct catttccctt aaatcgattt aagggaaatg           50

<210> SEQ ID NO 11
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Bond to 3'-residue modified to thiophosphate
<220> FEATURE:
<221> NAME/KEY: misc_feature
<222> LOCATION: (20)..(20)
<223> OTHER INFORMATION: Bond to 3'-residue modified to
      hexa(propylphosphate)
<220> FEATURE:
<221> NAME/KEY: misc_feature
<222> LOCATION: (21)..(23)
<223> OTHER INFORMATION: Bond to 3'-residue modified to thiophosphate
<220> FEATURE:
<221> NAME/KEY: misc_feature
<222> LOCATION: (35)..(35)
<223> OTHER INFORMATION: Bond to 3'-residue modified to
      tetra(propylphosphate)
<220> FEATURE:
<221> NAME/KEY: misc_feature
<222> LOCATION: (47)..(49)
<223> OTHER INFORMATION: Bond to 3'-residue modified to thiophosphate
<220> FEATURE:
<221> NAME/KEY: misc_feature
<222> LOCATION: (50)..(50)
<223> OTHER INFORMATION: 3'-terminal modified with
      tetra(propylphosphate)hexylamine

<400> SEQUENCE: 11
tccatgacgt tcctgatgct actcttgcca attacgtaat tggcaagagt           50

<210> SEQ ID NO 12
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (1)..(1)
<223> OTHER INFORMATION: 5'terminal modified with penta(propylphosphate)
<220> FEATURE:
<221> NAME/KEY: misc_feature
<222> LOCATION: (1)..(3)
<223> OTHER INFORMATION: Bond to 3'-residue modified to thiophosphate
<220> FEATURE:
<221> NAME/KEY: misc_feature
<222> LOCATION: (15)..(15)
<223> OTHER INFORMATION: Bond to 3'-residue modified to
      tetra(propylphosphate)
<220> FEATURE:
<221> NAME/KEY: misc_feature
<222> LOCATION: (27)..(29)
<223> OTHER INFORMATION: Bond to 3'-residue modified to thiophosphate
<220> FEATURE:
<221> NAME/KEY: misc_feature
<222> LOCATION: (30)..(30)
<223> OTHER INFORMATION: 3'-terminal modified to
      tetra(propylphosphate)hexylamine

<400> SEQUENCE: 12
catttcccgt aaatcgattt acgggaaatg                                            30

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Bond to 3'-residue modified to thiophosphate
<220> FEATURE:
<221> NAME/KEY: misc_feature
<222> LOCATION: (15)..(19)
<223> OTHER INFORMATION: Bond to 3'-residue modified to thiophosphate

<400> SEQUENCE: 13
ggggtcaacg ttgagggggg                                                       20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Bond to 3'-residue modified to thiophosphate
<220> FEATURE:
<221> NAME/KEY: misc_feature
<222> LOCATION: (15)..(19)
<223> OTHER INFORMATION: Bond to 3'-residue modified to thiophosphate

<400> SEQUENCE: 14
ggggtcaacg ttgagggggg                                                       20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Bond to 3'-residue modified to thiophosphate
<220> FEATURE:
<221> NAME/KEY: misc_feature
```

<222> LOCATION: (16)..(19)
<223> OTHER INFORMATION: Bond to 3'-residue modified to thiophosphate

<400> SEQUENCE: 15
gggggacgat cgtcgggggg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Bond to 3'-residue modified to thiophosphate
<220> FEATURE:
<221> NAME/KEY: misc_feature
<222> LOCATION: (15)..(19)
<223> OTHER INFORMATION: Bond to 3'-residue modified to thiophosphate

<400> SEQUENCE: 16
gggggacgat cgtcgggggg                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Bond to 3'-residue modified to thiophosphate
<220> FEATURE:
<221> NAME/KEY: misc_feature
<222> LOCATION: (16)..(19)
<223> OTHER INFORMATION: Bond to 3'-residue modified to thiophosphate

<400> SEQUENCE: 17
ggtgcatcga tgcagggggg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Bond to 3'-residue modified to thiophosphate
<220> FEATURE:
<221> NAME/KEY: misc_feature
<222> LOCATION: (16)..(19)
<223> OTHER INFORMATION: Bond to 3'-residue modified to thiophosphate

<400> SEQUENCE: 18
ggtgcatcga tgcagggggg                                               20

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Bond to 3'-residue modified to thiophosphate
<220> FEATURE:

```
<221> NAME/KEY: misc_feature
<222> LOCATION: (16)..(20)
<223> OTHER INFORMATION: Bond to 3'-residue modified to thiophosphate

<400> SEQUENCE: 19
ggggacgacg tcgtgggggg g                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Bond to 3'-residue modified to thiophosphate
<220> FEATURE:
<221> NAME/KEY: misc_feature
<222> LOCATION: (16)..(20)
<223> OTHER INFORMATION: Bond to 3'-residue modified to thiophosphate

<400> SEQUENCE: 20
ggggacgacg tcgtgggggg g                                              21

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Bond to 3'-residue modified to thiophosphate

<400> SEQUENCE: 21
tccatgacgt tcctgatgct                                                20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Bond to 3'-residue modified to thiophosphate

<400> SEQUENCE: 22
tccatgacgt tcctgacgtt                                                20

<210> SEQ ID NO 23
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Bond to 3'-residue modified to thiophosphate

<400> SEQUENCE: 23
tcgtcgtttt gtcgttttgt cgtt                                           24

<210> SEQ ID NO 24
<211> LENGTH: 22
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Bond to 3'-residue modified to thiophosphate

<400> SEQUENCE: 24
tcgtcgttgt cgttttgtcg tt                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Bond to 3'-residue modified to thiophosphate

<400> SEQUENCE: 25
tcgtcgtttt cggcgcgcgc cg                                              22

<210> SEQ ID NO 26
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(24)
<223> OTHER INFORMATION: Bond to 3'-residue modified to thiophosphate

<400> SEQUENCE: 26
tcgtcgtcgt tcgaacgacg ttgat                                           25
```

US 10,829,765 B2

STAT3 INHIBITORS AND USES THEREOF

CROSS-REFERENCES TO RELATED APPLICATIONS

This application is a divisional of U.S. application Ser. No. 15/160,865 filed May 20, 2016, issued as U.S. Pat. No. 9,976,147, which is a continuation of International Application No. PCT/US2014/066969 filed Nov. 21, 2014, which claims priority to U.S. Application No. 61/907,953 filed Nov. 22, 2013, and U.S. Application No. 62/077,035 filed Nov. 7, 2014, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. CA155367 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 48440-537 C02US_ST25.TXT, created Jul. 11, 2018, 12,506 bytes, machine format IBM-PC, MS-Windows operating system, is hereby incorporated by reference.

BACKGROUND

STAT3 transcription factor, which is persistently activated in cancer cells and in diverse tumor-associated immune cells, is a critical mediator of tumorigenesis and immune evasion. As a convergence point for cytokine, growth factor and oncogenic kinase signaling, STAT3 is a highly desirable therapeutic target. However, pharmacological inhibition of proteins lacking enzymatic activity, such as STAT3, is challenging and requires alternative strategies. One of them is to block STAT3 DNA binding and transcriptional activation using competitive inhibitors, such as decoy oligodeoxynucleotides (dODN). Decoy ODNs comprise the specific, consensus sequence of the transcription factor binding site. The limiting factor in the clinical application of dODNs is difficulty in their targeted delivery, additionally complicated by the inherent sensitivity of the immune system to nucleic acids. However, immune cells may themselves be essential therapeutic targets in cancer therapy. We previously demonstrated that ligand for the intracellular receptor TLR9 (CpG ODN) allows for the delivery of oligonucleotides, such as siRNA, specifically to TLR9-positive target cells without any transfection or packaging reagents. Disclosed herein are solutions to these and other problems in the art.

BRIEF SUMMARY

In an aspect is provided a compound including a TLR-binding nucleic acid substituent conjugated to a STAT-binding nucleic acid substituent.

In an aspect is provided a pharmaceutical composition including a pharmaceutically acceptable excipient and a compound described herein (including in an aspect, embodiment, table, figure, claim, sequence listing, or example).

In an aspect is provided a method of treating cancer in a patient in need of the treatment, the method including administering a therapeutically effective amount of a compound described herein (including in an aspect, embodiment, table, figure, claim, sequence listing, or example).

In an aspect is provided a method of treating a viral disease associated with STAT3-dependent immunosuppression in a patient in need of the treatment, the method including administering a compound, or pharmaceutically acceptable salt thereof, described herein (including in an aspect, embodiment, table, figure, claim, sequence listing, or example).

In an aspect is provided a method of inhibiting the growth of a cancer cell including contacting the cancer cell with a compound described herein (including in an aspect, embodiment, table, figure, claim, sequence listing, or example).

In an aspect is provided a method of stimulating the immune system of a patient in need thereof including administering an effective amount of a compound described herein (including in an aspect, embodiment, table, figure, claim, sequence listing, or example).

In an aspect is provided a method of reducing the activity of a STAT transcription factor in a cell including contacting the cell with a compound described herein (including in an aspect, embodiment, table, figure, claim, sequence listing, or example).

BRIEF DESCRIPTION OF THE DRAWINGS

FIG. 1A: Sequence of the single stranded CpG-STAT3 dODN conjugate (SEQ ID NO:6). FIG. 1B: Predicted hairpin structure of the folded CpG-STAT3 dODN with both parts of the conjugate indicated, wherein o=x (e.g. C3 carbon chain or alkylphosphate) as in FIG. 1A. FIG. 1C: Chemically-modified CpG-STAT3 dODN has improved resistance to degradation in human serum.

FIG. 3A: Mouse splenocytes were incubated with fluorescently-labeled CpG-STAT3 dODN in indicated concentrations for 2 h without any transfection reagents. Percentages of Cy3-positive cells pDCs (CD11c+B220+), mDCs (CD11c+B220−), macrophages (MAC; F4/80+Gr1−), B cells (B220+CD11c−), granulocytes (Gr1+F4/80−) and T cells (CD3+) were assessed using flow cytometry. FIG. 3B: Rapid internalization of CpG-STAT3 dODN by transformed mouse macrophages (RAW264.7) and various types of mouse cancer cells, such as M2 and B16 melanoma, TC2 neuroendocrine and MB49 bladder cancer cells. FIG. 3C: CpG(A)-STAT3 dODN, with A-type CpG sequence optimized for immunostimulation of human cells is internalized with similar efficiency as CpG(B)-STAT3 dODN by mouse macrophages and cancer cells.

FIG. 6A: Human B cell lymphoma (Daudi), AML (MV4-11) and prostate cancer cells (DU145) were incubated with 500 nM CpG(A)-STAT3 dODN for 2 days. The induction of cell death was measured after Annexin V and 7AAD staining using flow cytometry. The percentages of early apoptotic (Annexin V+7AAD−) and late apoptotic (Annexin V+7AAD+) cells is shown. FIG. 6B: Mouse M2 melanoma and Cbfb/MYH11/Mp11 AML (CMM) cells were incubated 500 nM CpG(B)-STAT3 dODN for 2 days and analyzed as described for FIG. 6A.

FIG. 7A: Disclosed is Xenogen imaging before and during treatment to detect AML regression after repeated injections of CpG(A)-STAT3 dODN compared to both control groups. FIG. 7B: CpG(A)-STAT3 dODN treatment reduces the percentage of AML cells in various organs including bone marrow (BM) and blood as assessed using flow cytometry. Shown are combined results from 6 mice/group; means±SEM.

FIG. 8A: Figure depicts the effect of CpG-STAT3 dODN treatments on spleen cellularity. Shown are representative spleen sizes (left) and the measurement of spleens weight (right). FIG. 8B: Flow cytometric analysis of GFP+c-Kit+ AML cells in blood, bone marrows, spleens, left to right, and (FIG. 8C) the percentage of CD8+ T cells infiltrating spleens from various groups of mice. Shown are combined results from 6 mice/group; means±SEM.

FIGS. 16A-16B: Chemically-modified CpG-STAT3 dODN has improved resistance to degradation by serum nucleases. CpG-STAT3 dODN was incubated in 50% in mouse (FIG. 16A) or human sera (FIG. 16B) for up to 7 days, then resolved on 7.5M Urea/15% PAGE gel and stained using ethidium bromide. FIGS. 16A-16B: Top panel—representative gel images. Bottom—graphs showing quantification of band intensities from 3 independent experiments; shown are means±SEM. The estimated halflife of CpG(A)-STAT3dODN was indicated.

FIG. 17A: Levels of STAT3 activity in human MV4-11 AML cells incubated for 48 h with CpG-STAT3dODN in comparison to CpG-scrODN (with scrambled decoy sequence) or GpC-STAT3dODN (lacking TLR9-targeting motif) used as negative controls. The phosphorylation of tyrosine 705 in STAT3 (pSTAT3) in comparison to total STAT3 levels was assessed using western blotting. FIG. 17B: Splenocytes were incubated with different concentrations of CpG-STAT3dODN for 48 h. pSTAT3 was assessed using intracellular staining with specific antibodies and assessed using flow cytometry; means±SEM.

FIGS. 18A-18B: Reporter pGL3 plasmids encoding STAT3 responsive a2M-promoter-luciferase constructs or empty vectors were transiently expressed MV4-11 (FIG. 18A) and KG1a (FIG. 18B) acute myeloid leukemia cells. One day later cells were incubated for 48 h with various doses of CpGSTAT3dODN in comparison to CpG-scrODN or GpC-STAT3dODN used as negative controls. The level of STAT3-induced transcriptional activity was assessed in cell lysates by measuring luciferase activity in 3 independent experiments; means±SEM.

(FIG. 20A) CpG-STAT3dODN treatment reduces splenomegaly (FIG. 20A) and the percentage of AML cells in spleen (FIGS. 20B-20C—top row) and bone marrow (FIG. 20C—bottom row) as assessed using flow cytometry. Shown are results from 4 independent experiments; means±SEM (n=5). (FIG. 20D) STAT3 inhibition results in decreased levels of STAT3 and Bcl-XL proteins expression in splenic AML cells isolated from 5 different mice. Shown are results of western blotting using β-actin for loading control.

FIGS. 21A-21C. Lack of functional immune effector cells in NSG mice reduces the efficacy of CpGSTAT3dODN treatment against AML. The immunodeficient NSG mice were injected i.v. using Cbfb-MYH11 AML cells. After leukemia was established (1-5% of circulating AML cells), mice were injected 6 times every other day i.v. using 5 mg/kg of CpG-STAT3dODN or control CpG-scrODN as in FIG. 20A-D. Percentages of AML cells in blood (FIG. 21A), bone marrow (FIG. 21B) and spleens (FIG. 21C) were assessed using flow cytometry. Shown are representative dot plots (left panels) and results summary (right panel); means±SEM (n=5).

(FIG. 25A) PBMCs from AML patients' were incubated for 1 h with 250 nM of Cy3-labeled CpG-STAT3dODN conjugate or STAT3dODN alone. The uptake of indicated oligonucleotides CFSE was assessed using flow cytometry. Left—representative dot plot; right—data summary; means±SD (n=4). (FIGS. 25B-25E) CpG-STAT3 dODN inhibits STAT3 phosphorylation (FIG. 25B) and arginase expression levels (FIG. 25C), while weakly inhibiting PD-L1 (FIG. 25D) and upregulating HLA-DR (FIG. 25E) in pts' AML cells as measured using flow cytometry; means±SD (n=5). (FIG. 25F) Blocking STAT3 using CpG-dODN strategy reverses immunosuppressive effect of AML cells on T cell proliferation. CFSE dilution assay using 4:1 ration of AML to T cells; gated are proliferating T cells.

(FIG. 26A) CD15+ MDSC generated in the presence of human prostate cancer cells (DU145) are potently immunosuppressive. PBMCs from healthy subjects were cultured in the presence of DU145 supernatant for 7 days and the used for autologous T cell proliferation assays in comparison with CD15− and total PBMCs. Shown are results from one of three independent assays. (FIG. 26B) CpG-STAt3dODN is quickly internalized by CD15+ MDSC in dose-dependent manner. (FIG. 26C) CpG-STAT3dODN but not CpG-scrODN reverses immunosuppressive effect of MDSCs on T cell proliferation as measured using CFSE dilution assay; means±SD (n=3).

FIG. 28A) TLR9 expression at the mRNA and protein levels in the indicated human immune cells (gMDSC=granulocytic myeloid-derived suppressor cells). (FIG. 28B) TLR9 expression at the mRNA and protein levels in mouse Cbfb/Myh11 acute myeloid leukemia cells.

DETAILED DESCRIPTION

Figures 1A, 1B:
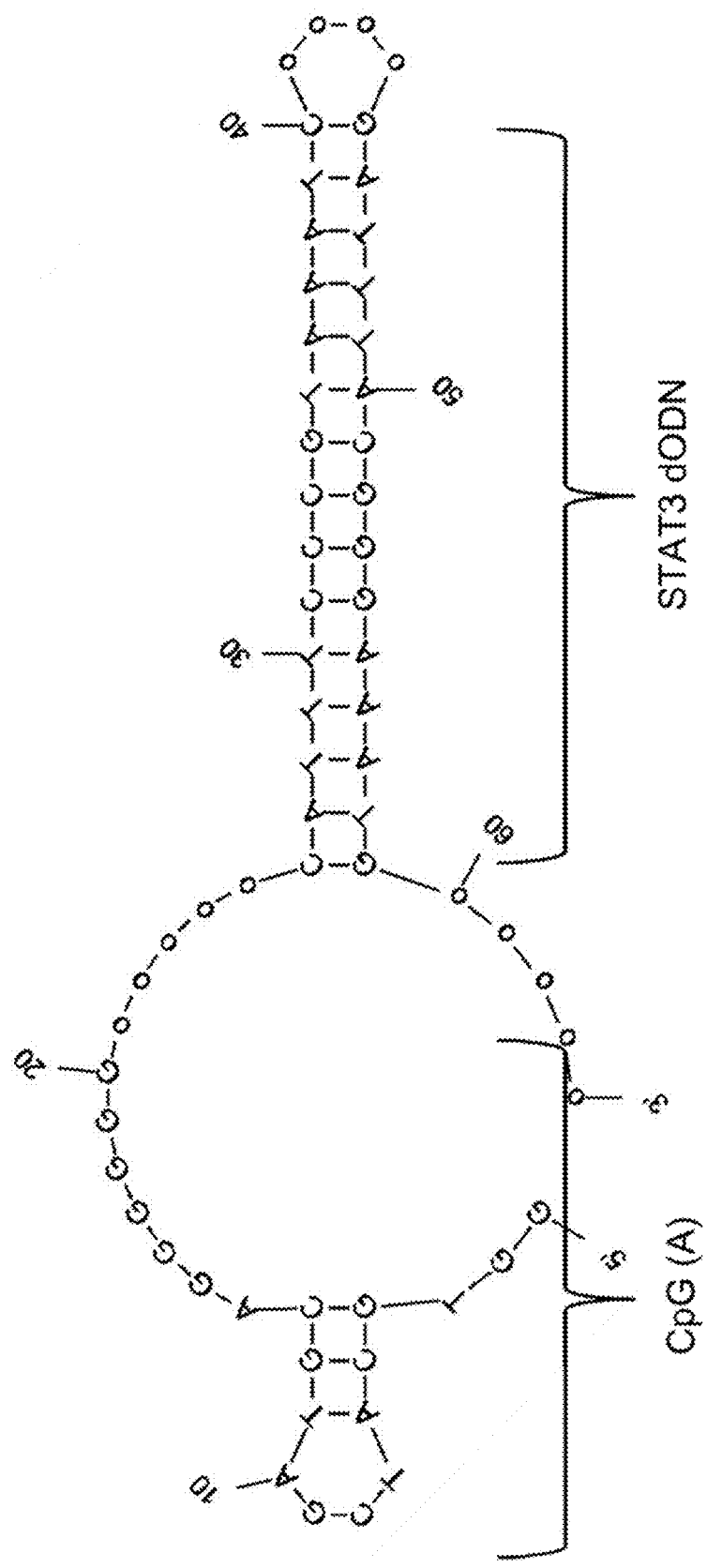
FIGS. 1A-1C. Design of CpG-STAT3 decoy oligodeoxynucleotide (dODN) and chemical modification for enhanced serum stability.

Disclosed herein are compositions including the ligand for the intracellular receptor TLR9 (CpG ODN) and method of using the same for the delivery of oligonucleotides, specifically to TLR9-positive target cells without any transfection or packaging reagents. Disclosed herein is use of this approach to deliver STAT3 decoy ODN into variety of human and mouse target cells both in vitro and in vivo. These include normal myeloid cells or B lymphocytes and malignant cells, such as acute myeloid leukemia (AML), B cell lymphoma and castration-resistant prostate cancer cells. Due to extensive chemical modification (phosphothioation) of the backbone, the CpG-STAT3 dODN are highly resistant to serum degradation with half-life exceeding 48 hrs. Thus, CpG-dODNs are suitable for systemic administration against metastatic cancers. As disclosed herein, using a disseminated model of human AML, repeated intravenous administration of CpG-STAT3 dODN results in eradication of MV4-11 leukemia within two weeks of treatment. The antitumor efficacy of this strategy seems to be further enhanced by immunostimulatory effect of combined TLR9-triggering and STAT3 blocking. In syngeneic mouse model of Cbfb/MYH11/Mp11 leukemia, i.v. injections of CpG-STAT3 dODN resulted in tumor regression from bone marrow, spleen and blood within 12 days of treatment. The antitumor effect was accompanied by immune cell activation and T cell infiltration into various organs. Thus, CpG-dODN strategy can overcome the limitations of small molecule drugs by expanding the list of therapeutic targets to crucial yet currently non-druggable molecules (e.g. transcription factors).

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)N R'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC (O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)-(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula -(CRR')$_s$-X'—(C"R"R'")$_d$—, where s and d are independently integers of from 0 to 3, and X' is —O—, —S—, —S(O)—, —S(O)$_2$, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from: (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from: (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

The symbol "⤳" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) would be known or may be determined by a person of ordinary skill in the art. The term "treating" and conjugations thereof, include prevention of an injury, pathology, condition, or disease (e.g. preventing the development of one or more symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)). For example certain methods herein treat viral disease (e.g. herpesvirus infection associated disease or hepatitis virus infection associated disease or HIV infection associated disease) by decreasing or reducing or preventing the occurrence, growth, or progression of the virus infection or virus; or treat viral disease (e.g. herpesvirus infection associated disease or hepatitis virus infection associated disease or HIV infection associated disease) by decreasing a symptom of viral disease (e.g. herpesvirus infection associated disease or hepatitis virus infection associated disease or HIV infection associated disease).

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)) means that the disease (e.g. cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)) is caused by (in whole or in part), or a symptom of the disease is caused by (in whole or in part) the substance or substance activity or function. For example, a symptom of a disease or condition associated with an increase in STAT3 activity may be a symptom that results (entirely or partially) from an increase in STAT3 activity (e.g increase in STAT3 transcriptional activation, increase in STAT3 activation of a signal transduction or signalling pathway). As used herein, what is described as being associated with a disease, if a causative agent, could be a target for treatment of the disease. For example, a disease associated with increased STAT3 activity (e.g increase in STAT3 transcriptional activation, increase in STAT3 activation of a signal transduction or signalling pathway), may be treated with an agent (e.g. compound as described herein) effective for decreasing the level of activity of STAT3 or STAT3 pathway. For example, a disease associated with STAT3, may be treated with an agent (e.g. compound as described herein) effective for decreasing the level of activity of STAT3 or a downstream component or effector of STAT3. For example, a symptom of a disease or condition associated with an increase in STAT (e.g. STAT1, STAT2, STAT3, STAT4, STAT5A, STAT5B, or STAT6) activity may be a symptom that results (entirely or partially) from an increase in STAT (e.g. STAT1, STAT2, STAT3, STAT4, STAT5A, STAT5B, or STAT6) activity (e.g increase in STAT (e.g. STAT1, STAT2, STAT3, STAT4, STAT5A, STAT5B, or STAT6) transcriptional activation, increase in STAT (e.g. STAT1, STAT2, STAT3, STAT4, STAT5A, STAT5B, or STAT6) activation of a signal transduction or signalling pathway). As used herein, what is described as being associated with a disease, if a causative agent, could be a target for treatment of the disease. For example, a disease associated with increased STAT (e.g. STAT1, STAT2, STAT3, STAT4, STAT5A, STAT5B, or STAT6) activity (e.g increase in STAT (e.g. STAT1, STAT2, STAT3, STAT4, STAT5A, STAT5B, or STAT6) transcriptional activation, increase in STAT (e.g. STAT1, STAT2, STAT3, STAT4, STAT5A, STAT5B, or STAT6) activation of a signal transduction or signalling pathway), may be treated with an agent (e.g. compound as described herein) effective for decreasing the level of activity of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway. For example, a disease associated with a STAT transcription factor (e.g. STAT1, STAT2, STAT3, STAT4, STAT5A, STAT5B, or STAT6) may be treated with an agent (e.g. compound as described herein) effective for decreasing the level of activity of a STAT transcription factor (e.g. STAT1, STAT2, STAT3, STAT4, STAT5A, STAT5B, or STAT6) or a downstream component or effector of a STAT transcription factor (e.g. STAT1, STAT2, STAT3, STAT4, STAT5A, STAT5B, or STAT6).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. a STAT transcription factor (e.g. STAT1, STAT2, STAT3, STAT4, STAT5A, STAT5B, or STAT6)). In some embodiments contacting includes allowing a compound described herein to interact with a protein or enzyme that is involved in a signaling pathway (e.g. a STAT transcription factor (e.g. STAT1, STAT2, STAT3, STAT4, STAT5A, STAT5B, or STAT6) pathway).

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g. a STAT transcription factor (e.g. STAT1, STAT2, STAT3, STAT4, STAT5A, STAT5B, or STAT6) activated pathway). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. level of a STAT transcription factor (e.g. STAT1, STAT2, STAT3, STAT4, STAT5A, STAT5B, or STAT6) activity or protein or level or activity of a component of a STAT transcription factor (e.g. STAT1, STAT2, STAT3, STAT4, STAT5A, STAT5B, or STAT6) pathway, wherein each is associated with cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)) or a viral disease (e.g. herpesvirus infection associated disease or hepatitis virus infection associated disease or HIV infection associated disease). Inhibition may include, at least in part, partially or totally decreasing stimulation, decreasing or reducing activation, or deactivating, desensitizing, or down-regulating signal transduction or enzymatic activity or the amount of a protein (e.g. a STAT transcription factor (e.g. STAT1, STAT2, STAT3, STAT4, STAT5A, STAT5B, or STAT6), protein downstream in a pathway from a STAT transcription factor (e.g. STAT1, STAT2, STAT3, STAT4, STAT5A, STAT5B, or STAT6), protein downstream in a pathway activated by a STAT transcription factor (e.g. STAT1, STAT2, STAT3, STAT4, STAT5A, STAT5B, or STAT6)) that may modulate the level of another protein or increase cell survival (e.g. a STAT transcription factor (e.g. STAT1, STAT2, STAT3, STAT4, STAT5A, STAT5B, or STAT6) pathway activity may increase cell survival in cells that may or may not have an increase in a STAT transcription factor (e.g. STAT1, STAT2, STAT3, STAT4, STAT5A, STAT5B, or STAT6) pathway activity relative to a non-disease control or decrease in a STAT transcription factor (e.g. STAT1, STAT2, STAT3, STAT4, STAT5A, STAT5B, or STAT6) pathway activity may increase cell survival in cells that may or may not have a decrease in a STAT transcription factor (e.g. STAT1, STAT2, STAT3, STAT4, STAT5A, STAT5B, or STAT6) pathway activity relative to a non-disease control). In embodiments, the activity or function of a STAT transcription factor (e.g. STAT1, STAT2, STAT3, STAT4, STAT5A, STAT5B, or STAT6) that is inhibited is STAT (e.g. STAT1, STAT2, STAT3, STAT4, STAT5A, STAT5B, or STAT6) transcriptional activation. In embodiments, the activity or function of a STAT transcription factor (e.g. STAT1, STAT2, STAT3, STAT4, STAT5A, STAT5B, or STAT6) that is inhibited is STAT (e.g. STAT1, STAT2, STAT3, STAT4, STAT5A, STAT5B, or STAT6) transcriptional inhibition. In embodiments, the activity or function of a STAT transcription factor (e.g. STAT1, STAT2, STAT3, STAT4, STAT5A, STAT5B, or STAT6) that is inhibited is STAT transcription factor (e.g. STAT1, STAT2, STAT3, STAT4, STAT5A, STAT5B, or STAT6) binding to genomic DNA. In embodiments, the activity or function of a STAT transcription factor (e.g. STAT1, STAT2, STAT3, STAT4, STAT5A, STAT5B, or STAT6) that is inhibited is STAT (e.g. STAT1, STAT2, STAT3, STAT4, STAT5A, STAT5B, or STAT6) binding to a STAT (e.g. STAT1, STAT2, STAT3, STAT4, STAT5A, STAT5B, or STAT6) binding site in genomic DNA.

As defined herein, the term "activation", "activate", "activating" and the like in reference to a protein-activator (e.g. agonist) interaction means positively affecting (e.g. increasing) the activity or function of the protein (e.g. a STAT transcription factor (e.g. STAT1, STAT2, STAT3, STAT4, STAT5A, STAT5B, or STAT6), component of a pathway including a STAT transcription factor (e.g. STAT1, STAT2, STAT3, STAT4, STAT5A, STAT5B, or STAT6), or component of a pathway including a STAT transcription factor (e.g. STAT1, STAT2, STAT3, STAT4, STAT5A, STAT5B, or STAT6)) relative to the activity or function of the protein in the absence of the activator (e.g. compound described herein). In some embodiments, activation refers to an increase in the activity of a signal transduction pathway or signaling pathway (e.g. a STAT transcription factor (e.g. STAT1, STAT2, STAT3, STAT4, STAT5A, STAT5B, or STAT6) pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of STAT (e.g. STAT1, STAT2, STAT3, STAT4, STAT5A, STAT5B, or STAT6) activity or level of protein or activity decreased by a STAT transcription factor (e.g. STAT1, STAT2, STAT3, STAT4, STAT5A, STAT5B, or STAT6) or protein associated with cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)). Activation may include, at least in part, partially or totally increasing stimulation, increasing or enabling activation, or activating, sensitizing, or up-regulating signal transduction or enzymatic activity or the amount of a protein (e.g. a STAT transcription factor (e.g. STAT1, STAT2, STAT3, STAT4, STAT5A, STAT5B, or STAT6), protein downstream of a STAT transcription factor (e.g. STAT1, STAT2, STAT3, STAT4, STAT5A, STAT5B, or STAT6), protein activated or upregulated by a STAT transcription factor (e.g. STAT1, STAT2, STAT3, STAT4, STAT5A, STAT5B, or STAT6)) that may modulate the level of another protein or increase cell survival (e.g. increase in a STAT transcription factor (e.g. STAT1, STAT2, STAT3, STAT4, STAT5A, STAT5B, or STAT6) activity may increase cell survival in cells that may or may not have an increase in a STAT transcription factor (e.g. STAT1, STAT2, STAT3, STAT4, STAT5A, STAT5B, or STAT6) activity relative to a non-disease control).

The term "modulator" refers to a composition that increases or decreases the level of a target molecule or the function of a target molecule (e.g. a STAT transcription factor (e.g. STAT1, STAT2, STAT3, STAT4, STAT5A, STAT5B, or STAT6) transcriptional activation or a STAT transcription factor (e.g. STAT1, STAT2, STAT3, STAT4, STAT5A, STAT5B, or STAT6) binding to genomic DNA, or a STAT transcription factor (e.g. STAT1, STAT2, STAT3, STAT4, STAT5A, STAT5B, or STAT6) binding to a STAT transcription factor (e.g. STAT1, STAT2, STAT3, STAT4, STAT5A, STAT5B, or STAT6) binding site on DNA). In some embodiments, a modulator of a STAT transcription factor (e.g. STAT1, STAT2, STAT3, STAT4, STAT5A, STAT5B, or STAT6) or a STAT transcription factor (e.g.

STAT1, STAT2, STAT3, STAT4, STAT5A, STAT5B, or STAT6) pathway is a compound that reduces the severity of one or more symptoms of a disease associated with a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway (e.g. disease associated with an increase in the level of a STAT transcription factor (e.g. STAT1, STAT2, STAT3, STAT4, STAT5A, STAT5B, or STAT6) activity or protein or a STAT transcription factor (e.g. STAT1, STAT2, STAT3, STAT4, STAT5A, STAT5B, or STAT6) pathway activity or protein, for example cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)) or a disease that is not caused by a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway but may benefit from modulation of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway activity (e.g. decreasing in level or level of activity of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway). In embodiments, a modulator of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway is an anti-cancer agent. In embodiments, a modulator of a STAT transcription factor (e.g. STAT1, STAT2, STAT3, STAT4, STAT5A, STAT5B, or STAT6) or a STAT transcription factor (e.g. STAT1, STAT2, STAT3, STAT4, STAT5A, STAT5B, or STAT6) pathway is an anti-viral agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Disease" or "condition" refer to a state of being or health status of a patient or subject capable of being treated with a compound, pharmaceutical composition, or method provided herein. In some embodiments, the disease is a disease related to (e.g. caused by) an increase in the level of a STAT transcription factor (e.g. STAT1, STAT2, STAT3, STAT4, STAT5A, STAT5B, or STAT6), STAT (e.g. STAT1, STAT2, STAT3, STAT4, STAT5A, STAT5B, or STAT6) phosphorylation, or a STAT transcription factor (e.g. STAT1, STAT2, STAT3, STAT4, STAT5A, STAT5B, or STAT6) pathway activity, or pathway activated by a STAT transcription factor (e.g. STAT1, STAT2, STAT3, STAT4, STAT5A, STAT5B, or STAT6). In some embodiments, the disease is cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma). In embodiments, the disease is a viral disease (e.g. herpesvirus infection associated disease or hepatitis virus infection associated disease or HIV infection associated disease) associated with STAT3-dependent immunosuppression.

Examples of diseases, disorders, or conditions include, but are not limited to, cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma). In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

Further examples of diseases, disorders, or conditions include, but are not limited to viral diseases (e.g. herpesvirus infection associated disease or hepatitis virus infection associated disease or HIV infection associated disease) associated with STAT3-dependent immunosuppression. A viral disease associated with STAT3-dependent immunosuppression is a disease wherein the causative agent is a virus and wherein a symptom of the viral disease (i.e. virus infection) is immunosuppression dependent on STAT3. A herpesvirus infection associated disease is a disease wherein the causative agent is a herpesvirus (e.g. HHV-1, HHV-4 HHV-5 HHV-6A, HHV-6B, HHV-7, or HHV-8). A hepatitis infection associated disease is a disease wherein the causative agent is a hepatitis virus (e.g. hepatitis A virus, hepatitis B virus, hepatitis C virus, hepatitis D virus, or hepatitis E virus). An HIV infection associated disease is a disease wherein the causative agent is HIV. In embodiments, the viral disease associated with STAT3-dependent immunosuppression is HSV-1 infection and the causative agent is HHV-1 (herpes simplex virus-1, HSV-1). In embodiments, the viral disease associated with STAT3-dependent immunosuppression is HSV-2 infection and the causative agent is HHV-2 (herpes simplex virus-2, HSV-2). In embodiments, the viral disease associated with STAT3-dependent immunosuppression is chickenpox, shingles, or VZV infection, and the causative agent is HHV-3 (varicella zoster virus, VZV). In embodiments, the viral disease associated with STAT3-dependent immunosuppression is infectious mononucleosis, Burkitt's lymphoma, CNS lymphoma, post-transplant lymphoproliferative syndrome (PTLD), nasopharyngeal carcinoma, hairy leukoplakia, or CMV infection, and the causative agent is HHV-5 (cytomegalovirus, CMV). In embodiments, the viral disease associated with STAT3-dependent immunosuppression is sixth disease, roseola infantum, exanthema subitum, or HHV-6 infection and the causative agent is HHV-6A or HHV-6B (roseolovirus, herpes lymphotropic virus). In embodiments, the viral disease associated with STAT3-dependent immunosuppression is roseola infantum, exanthema subitum, or HHV-7 infection and the causative agent is HHV-7 (pityriasis rosea). In embodiments, the viral disease associated with STAT3-dependent immunosuppression is Kaposi's sarcoma, primary effusion lymphoma, multicentric Castleman's disease, or HHV-8 infection and the causative agent is HHV-8 (Kaposi's sarcoma-associated herpesvirus, KSHV). In embodiments, the viral disease associated with STAT3-dependent immunosuppression is hepatitis A and the causative agent is hepatitis A virus. In embodiments, the viral disease associated with STAT3-dependent immunosuppression is hepatitis B and the causative agent is hepatitis B virus. In embodiments, the viral disease associated with STAT3-dependent immunosuppression is hepatitis C and the causative agent is hepatitis C virus. In embodiments, the viral disease associated with STAT3-dependent immunosuppression is hepatitis D and the causative agent is hepatitis D virus. In embodiments, the viral disease associated with STAT3-dependent immunosuppression is hepatitis E and the causative agent is hepatitis E virus. In embodiments, the viral disease associated with STAT3-dependent immunosuppression is HIV infection or AIDS and the causative agent is HIV (human immunodeficiency virus) (e.g. HIV-1 or HIV-2).

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic) . . . . The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm.* Res. 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. a STAT transcription factor (e.g. STAT1, STAT2, STAT3, STAT4, STAT5A, STAT5B, or STAT6)), and/or reducing, eliminating, or slowing the progression of disease symptoms (e.g. symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) or viral disease (e.g. herpesvirus infection associated disease or hepatitis virus infection associated disease or HIV infection associated disease)). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma)), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma), or with other active agents known to be useful in treating viral disease (e.g. herpesvirus infection associated disease or hepatitis virus infection associated disease or HIV infection associated disease), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. prostate cancer, castration-resistant prostate cancer, breast cancer, triple negative breast cancer, glioblastoma, ovarian cancer, lung cancer, squamous cell carcinoma (e.g head, neck, or esophagus), colorectal cancer, leukemia, acute myeloid leukemia, lymphoma, B cell lymphoma, or multiple myeloma) such as surgery or with other treatments known to be useful in treating viral disease (e.g. herpesvirus infection associated disease or hepatitis virus infection associated disease or HIV infection associated disease).

The term "STAT" or "STAT transcription factor" are used interchangeably and refer to a "Signal transducer and activator of transcription" protein and homologs thereof (e.g. STAT1, STAT2, STAT3, STAT4, STAT5A, STAT5B, or STAT6). In embodiments, "STAT transcription factor" refers to a human protein (e.g. STAT1, STAT2, STAT3, STAT4, STAT5A, STAT5B, or STAT6). Included in the term "STAT transcription factor" are the wildtype and mutant forms of the protein (e.g. STAT1, STAT2, STAT3, STAT4, STAT5A, STAT5B, or STAT6). In embodiments, "STAT transcription factor" refers to the wildtype protein (e.g. STAT1, STAT2, STAT3, STAT4, STAT5A, STAT5B, or STAT6). In embodiments, "STAT transcription factor" refers to a mutant protein (e.g. STAT1, STAT2, STAT3, STAT4, STAT5A, STAT5B, or STAT6). "Phosphorylated STAT" refers to a STAT protein (e.g. STAT1, STAT2, STAT3, STAT4, STAT5A, STAT5B, or STAT6) that is phosphorylated and activated by the phosphorylation. In embodiments, activation of a STAT transcription factor (e.g. STAT1, STAT2, STAT3, STAT4, STAT5A, STAT5B, or STAT6) means the STAT (e.g. STAT1, STAT2, STAT3, STAT4, STAT5A, STAT5B, or STAT6) is capable of activating transcription. In embodiments, activated STAT (e.g. STAT1, STAT2, STAT3, STAT4, STAT5A, STAT5B, or STAT6) is phosphorylated on STAT1 Y701, STAT2, Y690, STAT3 Y705, STAT4 Y693, STAT5A Y694, STAT5B Y694, STAT6 Y641, or a residue corresponding to one of those residues, forms dimers (e.g. homodimers or heterodimers), translocates to the nucleus, and activates transcription. In embodiments, activated STAT (e.g. STAT1, STAT2, STAT3, STAT4, STAT5A, STAT5B, or STAT6) forms homodimers. In embodiments, activated STAT (e.g. STAT1, STAT2, STAT3, STAT4, STAT5A, STAT5B, or STAT6) forms heterodimers. An example of a protein that phosphorylates STAT (e.g. STAT1, STAT2, STAT3, STAT4, STAT5A, STAT5B, or STAT6) and thereby activate a STAT (e.g. STAT1, STAT2, STAT3, STAT4, STAT5A, STAT5B, or STAT6) includes JAK.

The term "STAT-binding nucleic acid sequence" refers to a nucleic acid capable of binding to a STAT (e.g. STAT1, STAT2, STAT3, STAT4, STAT5A, STAT5B, or STAT6) or a nucleic acid that forms part of a STAT-binding substituent (e.g. STAT1-, STAT2-, STAT3-, STAT4-, STAT5A-, STAT5B-, or STAT6-binding substituent). A STAT3-binding nucleic acid sequence is a nucleic acid capable of binding to STAT3 or a nucleic acid that forms part of a STAT3-binding substituent (STAT3-binding nucleic acid substituent).

The term "STAT1" refers to a "Signal transducer and activator of transcription 1" protein and homologs thereof. In embodiments, "STAT1" refers to the protein associated with Entrez Gene 6772, OMIM 600555, UniProt P42224, and/or RefSeq (protein) NP_009330. In embodiments, the reference numbers immediately above refer to the protein, and associated nucleic acids, known as of the date of filing of this application.

The term "STAT2" refers to a "Signal transducer and activator of transcription 2" protein and homologs thereof. In embodiments, "STAT2" refers to the protein associated with Entrez Gene 6773, OMIM 600556, UniProt P52630, and/or RefSeq (protein) NP_005410. In embodiments, the reference numbers immediately above refer to the protein, and associated nucleic acids, known as of the date of filing of this application.

The term "STAT4" refers to a "Signal transducer and activator of transcription 4" protein and homologs thereof. In embodiments, "STAT4" refers to the protein associated with Entrez Gene 6775, OMIM 600558, UniProt Q14765, and/or RefSeq (protein) NP_001230764. In embodiments, the reference numbers immediately above refer to the protein, and associated nucleic acids, known as of the date of filing of this application.

The term "STAT5A" refers to a "Signal transducer and activator of transcription 5A" protein and homologs thereof. In embodiments, "STAT5A" refers to the protein associated with Entrez Gene 6776, OMIM 601511, UniProt P42229, and/or RefSeq (protein) NP_003143. In embodiments, the reference numbers immediately above refer to the protein, and associated nucleic acids, known as of the date of filing of this application.

The term "STAT5B" refers to a "Signal transducer and activator of transcription 5B" protein and homologs thereof. In embodiments, "STAT5B" refers to the protein associated with Entrez Gene 6777, OMIM 604260, UniProt P51692, and/or RefSeq (protein) NP_036580. In embodiments, the reference numbers immediately above refer to the protein, and associated nucleic acids, known as of the date of filing of this application.

The term "STAT6" refers to a "Signal transducer and activator of transcription 6" protein and homologs thereof. In embodiments, "STAT6" refers to the protein associated with Entrez Gene 6778, OMIM 601512, UniProt P42226, and/or RefSeq (protein) NP_001171549. In embodiments, the reference numbers immediately above refer to the protein, and associated nucleic acids, known as of the date of filing of this application.

The term "STAT3" refers to the protein "Signal transducer and activator of transcription 3" and homologs thereof. In embodiments, "STAT3" refers to the human protein. Included in the term "STAT3" are the wildtype and mutant forms of the protein. In embodiments, "STAT3" refers to the wildtype protein. In embodiments, "STAT3" refers to a mutant protein. In embodiments, "STAT3" refers to the protein associated with Entrez Gene 6774, OMIM 102582, UniProt P40763, and/or RefSeq (protein) NP_003141. In embodiments, the reference numbers immediately above refer to the protein, and associated nucleic acids, known as of the date of filing of this application. "Phosphorylated STAT3" refers to a STAT3 protein that is phosphorylated and activated by the phosphorylation. In embodiments, a phosphorylated STAT3 is phosphorylated on tyrosine 705 or the residue corresponding to tyrosine 705 in homologs. In embodiments, activation of STAT3 means the STAT3 is capable of activating transcription. In embodiments, activated STAT3 is phosphorylated on tyrosine 705, or the residue corresponding to tyrosine 705, forms dimers (e.g. homodimers or heterodimers), translocates to the nucleus, and/or activates transcription. In embodiments, activated STAT3 forms homodimers. Examples of proteins that phosphorylate STAT3 and thereby activate STAT3 include JAK2, EGFR, c-MET, and PDGF-R.

"Anti-viral agent" is used in accordance with its plain ordinary meaning and refers to a composition (e.g. compound, drug, antagonist, inhibitor, modulator) having anti-infective properties or the ability to inhibit the growth or proliferation of virus. In some embodiments, an anti-viral agent is an agent identified herein having utility in methods of treating viral disease (e.g. herpesvirus infection associated disease or hepatitis virus infection associated disease or HIV infection associated disease). In some embodiments, an anti-viral agent is an agent approved by the FDA or similar regulatory agency of a country other than the USA, for treating viral disease (e.g. herpesvirus infection associated disease or hepatitis virus infection associated disease or HIV infection associated disease). Examples of anti-viral agents are well known in the art and include agents for treating herpesvirus infection associated disease, hepatitis virus infection associated disease, and HIV infection associated disease.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments, the nucleic acids herein contain phosphodiester bonds. In other embodiments, nucleic acid analogs are included that may have alternate backbones (e.g. phosphodiester derivatives), including, e.g., phosphoramidate, phosphorodiamidate, phosphorothioate (also know as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An amino acid residue in a protein "corresponds" to a given residue when it occupies the same essential structural position within the protein as the given residue. For example, a selected residue in a selected protein (e.g. homolog of human STAT, STAT1, STAT2, STAT4, STAT5A, STAT5B, or STAT6) corresponds to STAT1 Y701, STAT2, Y690, STAT3 Y705, STAT4 Y693, STAT5A Y694, STAT5B Y694, or STAT6 Y641 when the selected residue occupies the same essential spatial or other structural relationship as STAT1 Y701, STAT2, Y690, STAT3 Y705, STAT4 Y693, STAT5A Y694, STAT5B Y694, or STAT6 Y641 in each respective STAT protein. In some embodiments, where a selected protein is aligned for maximum homology with the a STAT protein, the position in the aligned selected protein aligning with STAT1 Y701, STAT2, Y690, STAT3 Y705, STAT4 Y693, STAT5A Y694, STAT5B Y694, or STAT6 Y641 is said to correspond to STAT1 Y701, STAT2, Y690, STAT3 Y705, STAT4 Y693, STAT5A Y694, STAT5B Y694, or STAT6 Y641 respectively. Instead of a primary sequence alignment, a three dimensional structural alignment can also be used, e.g., where the structure of the selected protein is aligned for maximum correspondence with the a human STAT protein and the overall structures compared. In this case, an amino acid that occupies the same essential position as STAT1 Y701, STAT2, Y690, STAT3 Y705, STAT4 Y693, STAT5A Y694, STAT5B Y694, or STAT6 Y641 in the structural model is said to correspond to STAT1 Y701, STAT2, Y690, STAT3 Y705, STAT4 Y693, STAT5A Y694, STAT5B Y694, or STAT6 Y641.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

A "label" or a "detectable moiety" is a composition detectable by spectroscopic, photochemical, biochemical, immunochemical, chemical, magnetic resonance imaging, or other physical means. For example, useful detectable moieties include $^{32}P$, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline SPIO, monochrystalline SPIO aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/ or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g. compound described herein). Any method known in the art for conjugating an oligonucleotide or protein to the label may be employed, e.g., using methods described in Hermanson, *Bioconjugate Techniques* 1996, Academic Press, Inc., San Diego.

MRI can be used to non-invasively acquire tissue images with high resolution. Paramagnetic agents or USPIO nanoparticles or aggregates thereof enhance signal attenuation on $T_2$-weighted magnetic resonance images, and conjugation of such nanoparticles to binding ligands permits the detection of specific molecules at the cellular level. For example, MRI with nanoparticle detection agents can detect small foci of cancer. See e.g., Y. W. Jun et al., 2005, *J. Am. Chern. Soc.* 127:5732-5733; Y. M. Huh et al., 2005, *J. Am. Chern. Soc.* 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, *NMR Biomed.* 17:484-499. Fluorescent dyes and fluorophores (e.g. fluorescein, fluorescein isothiocyanate, and fluorescein derivatives) can be used to non-invasively acquire tissue images with high resolution, with for example spectrophotometry, two-photon fluorescence, two-photon laser microscopy, or fluorescence microscopy (e.g. of tissue biopsies). MRI can be used to non-invasively acquire tissue images with high resolution, with for example paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents. MRI can be used to non-invasively acquire tissue images with high resolution, with for example Gadolinium, including liposomes or other delivery vehicles containing Gadolinium chelate ("Gd-chelate") molecules. Positron emission tomography (PET), PET/computed tomography (CT), single photon emission computed tomography (SPECT), and SPECT/CT can be used to non-invasively acquire tissue images with high resolution, with for example radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia. Ultrasound (ultrasonography) and contrast enhanced ultrasound (contrast enhanced ultrasonography) can be used to non-invasively acquire tissue images with high resolution, with for example biocolloids or microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.). X-ray imaging (radiography) or CT can be used to non-invasively acquire tissue images with high resolution, with for example iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, or gold nanoparticle aggregates. These detection methods and instruments and detectable moieties capable of being measured or detected by the corresponding method are non-limiting examples.

As used herein, the term "ultrasmall superparamagnetic iron oxide nanoparticle" or "USPIO nanoparticle" refers to superparamagnetic iron oxide particles ranging from 1 to 50 nm in diameter, more typically between 5 and 40 nm in diameter (excluding any coating applied after synthesis). USPIO nanoparticles are commonly made of maghemite ($Fe_2O_3$) or magnetite ($Fe_3O_4$) having crystal-containing regions of unpaired spins. Those magnetic domains are disordered in the absence of a magnetic field, but when a field is applied (i.e., while taking an MRI), the magnetic domains align to create a magnetic moment much greater than the sum of the individual unpaired electrons without resulting in residual magnetization of the particles.

As used herein, the term "TLR-binding nucleic acid substituent" refers to a substituent or moiety capable of binding to a toll-like receptor ("TLR") or activating a toll-like receptor, including at least one nucleic acid. In embodiments, a TLR-binding nucleic acid substituent is capable of binding a TLR. In embodiments, a TLR-binding nucleic acid substituent is capable of activating a TLR. In embodiments, a TLR-binding nucleic acid substituent is capable of activating a TLR without directly binding the TLR. In embodiments, a TLR-binding nucleic acid substituent is capable of binding a TLR without activating the TLR. In embodiments, a TLR-binding nucleic acid substituent is a nucleic acid. In embodiments, the TLR-binding nucleic acid substituent includes at least one nucleic acid analog. In embodiments, the TLR-binding nucleic acid substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In embodiments, a TLR-binding nucleic acid substituent includes or is DNA. In embodiments, a TLR-binding nucleic acid substituent includes or is RNA. In embodiments, a TLR-binding nucleic acid substituent includes or is a nucleic acid having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In embodiments, a TLR-binding nucleic acid substituent consists of a nucleic acid having internucleotide linkages selected from phosphodiesters and phosphorothioates. In embodiments, a TLR-binding nucleic acid substituent includes or is a nucleic acid having backbone linkages selected from phosphodiesters and phosphorodithioates. In embodiments, a TLR-binding nucleic acid substituent includes or is a nucleic acid having phosphodiester backbone linkages. In embodiments, a TLR-binding nucleic acid substituent includes or is a nucleic acid having phosphorothioate backbone linkages. In embodiments, a TLR-binding nucleic acid substituent includes or is a nucleic acid having phosphorodithioate backbone linkages. In embodiments, a TLR-binding nucleic acid substituent preferentially binds TLR9 over other TLR. In embodiments, a TLR-binding nucleic acid substituent specifically binds TLR9. In embodiments, a TLR-binding nucleic acid substituent preferentially binds TLR3 over other TLR. In embodiments, a TLR-binding nucleic acid substituent specifically binds TLR3. In embodiments, a TLR-binding nucleic acid substituent preferentially binds TLR7 over other TLR. In embodiments, a TLR-binding nucleic acid substituent specifically binds TLR7. In embodiments, a TLR-binding nucleic acid substituent preferentially binds TLR8 over other TLR. In embodiments, a TLR-binding nucleic acid substituent specifically binds TLR8. In embodiments, a TLR-binding nucleic acid substituent specifically binds a cellular subcompartment (e.g. endosome) associated TLR (e.g. TLR3, TLR7, TLR8, or TLR9). In embodiments, a TLR-binding nucleic acid substituent includes or is a G-rich nucleic acid (e.g. about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides). In embodiments, a TLR-binding nucleic acid substituent includes single stranded RNA (including phophodiester internucleotide linkages, phosphodiester derivative internucleotide linkages, or a combination both). In embodiments, a TLR-binding nucleic acid substituent includes double stranded RNA (including phophodiester internucleotide linkages, phosphodiester derivative internucleotide linkages, or a combination both) (e.g. poly (I:C). In embodiments, a TLR-binding nucleic acid substituent is a TLR3-binding nucleic acid substituent. In embodiments, a TLR-binding nucleic acid substituent is a TLR7-binding nucleic acid substituent. In embodiments, a TLR-binding nucleic acid substituent is a TLR8-binding nucleic acid substituent. In embodiments, a TLR-binding nucleic acid substituent is a TLR9-binding nucleic acid substituent. In embodiments, a TLR-binding nucleic acid substituent is a TLR-binding DNA substituent. In embodiments, a TLR-binding nucleic acid substituent is a TLR9-binding DNA substituent.

As used herein, the term "TLR-binding DNA substituent" refers to a substituent or moiety capable of binding to a toll-like receptor ("TLR"), including at least one deoxyribonucleic acid. In embodiments, a TLR-binding DNA substituent is a nucleic acid. In embodiments, the TLR-binding DNA substituent includes at least one nucleic acid analog. In embodiments, the TLR-binding DNA substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In embodiments, a TLR-binding DNA substituent includes DNA. In embodiments, all nucleotide sugars in a TLR-binding DNA substituent are deoxyribose (e.g., all nucleotides are DNA). In embodiments, a TLR-binding DNA substituent consists of DNA. In embodiments, a TLR-binding DNA substituent includes or is DNA having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In embodiments, a TLR-binding DNA substituent consists of DNA having internucleotide linkages selected from phosphodiesters and phosphorothioates. In embodiments, a TLR-binding DNA substituent includes or is DNA having backbone linkages selected from phosphodiesters and phosphorodithioates. In embodiments, a TLR-binding DNA substituent includes or is DNA including phosphodiester backbone linkages. In embodiments, a TLR-binding DNA substituent includes or is DNA including phosphorothioate backbone linkages. In embodiments, a TLR-binding DNA substituent includes or is DNA including phosphorodithioate backbone linkages. In embodiments, a TLR-binding DNA substituent preferentially binds TLR9 over other TLR. In embodiments, a TLR-binding DNA substituent specifically binds TLR9. In embodiments, a TLR-binding DNA substituent specifically binds TLR3. In embodiments, a TLR-binding DNA substituent specifically binds TLR7. In embodiments, a TLR-binding DNA substituent specifically binds TLR8. In embodiments, a TLR-binding DNA substituent specifically binds a cellular subcompartment (e.g. endosome) associated TLR (e.g. TLR3, TLR7, TLR8, or TLR9). In embodiments, a TLR-bonding DNA substituent includes or is a G-rich oligonucleotide (e.g. about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% G nucleotides). In embodiments, a TLR-binding DNA substituent includes a CpG motif, wherein C and G are nucleotides and p is the phosphate connecting the C and G. In embodiments, the CpG motif is unmethylated. In embodiments, a TLR-binding DNA substituent is a Class A CpG oligodeoxynucleotide (ODN). In embodiments, a TLR-binding DNA substituent is a Class B CpG oligodeoxynucleotide (ODN). In embodiments, a TLR-binding DNA substituent is a Class C CpG oligodeoxynucleotide (ODN). In embodiments, a TLR-binding DNA substituent (e.g., TLR9-binding DNA substituent) consists of deoxyribonucleic acids with A, G, C, or T bases and phosphodiester linkages and/or phosphodiester derivative linkages (e.g., phosphorothioate linkage(s)).

As used herein, the term "CpG motif" refers to a 5' C nucleotide connected to a 3' G nucleotide through a phosphodiester internucleotide linkage or a phosphodiester derivative internucleotide linkage. In embodiments, a CpG motif includes a phosphodiester internucleotide linkage. In embodiments, a CpG motif includes a phosphodiester derivative internucleotide linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate. Examples of Class A CpG ODNs include ODN D19, ODN 1585, ODN 2216, and ODN 2336.

As used herein, the term "Class B CpG ODN" or "B-class CpG ODN" or "K-type CpG ODN" or "Class B CpG DNA sequence" is used in accordance with its common meaning in the biological and chemical sciences and refers to a CpG motif including oligodeoxynucleotide including one or more of a 6mer motif including a CpG motif; phosphodiester derivatives linking all deoxynucleotides. In embodiments, a Class B CpG ODN includes one or more copies of a 6mer motif including a CpG motif and phosphodiester derivatives linking all deoxynucleotides. In embodiments, the phosphodiester derivative is phosphorothioate. In embodiments, a Class B CpG ODN includes one 6mer motif including a CpG motif. In embodiments, a Class B CpG ODN includes two copies of a 6mer motif including a CpG motif. In embodiments, a Class B CpG ODN includes three copies of a 6mer motif including a CpG motif. In embodiments, a Class B CpG ODN includes four copies of a 6mer motif including a CpG motif. Examples of Class B CpG ODNs include ODN 1668, ODN 1826, ODN 2006, and ODN 2007.

As used herein, the term "Class C CpG ODN" or "C-class CpG ODN" or "C-type CpG DNA sequence" is used in accordance with its common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 and ODN M362.

As used herein, the term "STAT-binding substituent" or "STAT-binding nucleic acid substituent" refers to a composition including one or more nucleic acids capable of binding to a STAT transcription factor (e.g. STAT1, STAT2, STAT3, STAT4, STAT5A, STAT5B, or STAT6). In embodiments, a STAT-binding substituent includes DNA (e.g. including phosphodiester internucleotide linkages, phosphodiester derivative internucleotide linkages, or a combination of phosphodiester and phosphodiester derivative internucleotide linkages). In embodiments, a STAT-binding substituent (e.g. STAT1-, STAT2-, STAT3-, STAT4-, STAT5A-, STAT5B-, or STAT6-binding substituent) includes a DNA sequence identical (except that it may include one or more phosphodiester derivative linkage(s)) to the genomic DNA sequence a STAT transcription factor (e.g. STAT1, STAT2, STAT3, STAT4, STAT5A, STAT5B, or STAT6) binds when modulating transcription. In embodiments, a STAT-binding substituent (e.g. STAT1-, STAT2-, STAT3-, STAT4-, STAT5A-, STAT5B-, or STAT6-binding substituent) is a DNA sequence identical (except that it may include one or more phosphodiester derivative linkage(s)) to the genomic DNA sequence a STAT transcription factor (e.g. STAT1, STAT2, STAT3, STAT4, STAT5A, STAT5B, or STAT6) binds when modulating transcription. In embodiments, a STAT-binding substituent (e.g. STAT1-, STAT2-, STAT3-, STAT4-, STAT5A-, STAT5B-, or STAT6-binding substituent) includes a DNA sequence identical (except that it may include one or more phosphodiester derivative linkage(s)) to the genomic DNA sequence phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, or STAT6) binds when modulating transcription. In embodiments, a STAT-binding substituent (e.g. STAT1-, STAT2-, STAT3-, STAT4-, STAT5A-, STAT5B-, or STAT6-binding substituent) is a DNA sequence identical (except that it may include one or more phosphodiester derivative linkage(s)) to the genomic DNA sequence phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, or STAT6) binds when modulating transcription. In embodiments, a STAT-binding substituent (e.g. STAT1-, STAT2-, STAT3-, STAT4-, STAT5A-, STAT5B-, or STAT6-binding substituent) includes a DNA sequence identical (except that it may include one or more phosphodiester derivative linkage(s)) to the genomic DNA sequence a STAT (e.g. STAT1, STAT2, STAT3, STAT4, STAT5A, STAT5B, STAT6, or combinations thereof) dimer binds when modulating transcription. In embodiments, a STAT-binding substituent (e.g. STAT1-, STAT2-, STAT3-, STAT4-, STAT5A-, STAT5B-, or STAT6-binding substituent) is a DNA sequence identical (except that it may include one or more phosphodiester derivative linkage(s)) to the genomic DNA sequence a STAT (e.g. STAT1, STAT2, STAT3, STAT4, STAT5A, STAT5B, STAT6, or combinations thereof) dimer binds when modulating transcription. In embodiments, a STAT-binding substituent (e.g. STAT1-, STAT2-, STAT3-, STAT4-, STAT5A-, STAT5B-, or STAT6-binding substituent) includes a DNA sequence identical (except that it may include one or more phosphodiester derivative linkage(s)) to the genomic DNA sequence a phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, STAT6, or combinations thereof) dimer binds when modulating transcription. In embodiments, a STAT-binding substituent (e.g. STAT1-, STAT2-, STAT3-, STAT4-, STAT5A-, STAT5B-, or STAT6-binding substituent) is a DNA sequence identical (except that it may include one or more phosphodiester derivative linkage(s)) to the genomic DNA sequence a phosphorylated (e.g. on STAT1 Y701, STAT2, Y690, STAT3 Y705, STAT4 Y693, STAT5A Y694, STAT5B Y694, STAT6 Y641, or a residue corresponding to one of those residues) STAT (e.g. STAT1, STAT2, STAT3, STAT4, STAT5A, STAT5B, STAT6, or combinations thereof) dimer binds when modulating transcription.

As used herein, the term "STAT3-binding nucleic acid substituent" or "STAT3-binding substituent" refers to a composition including one or more nucleic acids capable of binding to STAT3. In embodiments, a STAT3-binding substituent includes DNA (e.g. including phosphodiester internucleotide linkages, phosphodiester derivative internucleotide linkages, or a combination of phosphodiester and phosphodiester derivative internucleotide linkages) (a "STAT3-binding DNA substituent"). In embodiments, all nucleotide sugars in a STAT3-binding DNA substituent are deoxyribose (e.g., all nucleotides are DNA). In embodiments, a STAT3-binding substituent is DNA (e.g. including phosphodiester internucleotide linkages, phosphodiester derivative internucleotide linkages, or a combination of phosphodiester and phosphodiester derivative internucleotide linkages). In embodiments, a STAT3-binding substituent includes a DNA sequence identical (except that it may include one or more phosphodiester derivative linkage(s)) to the genomic DNA sequence STAT3 binds when modulating transcription. In embodiments, a STAT3-binding substituent is a DNA sequence identical (except that it may include one or more phosphodiester derivative linkage(s)) to the genomic DNA sequence STAT3 binds when modulating transcription. In embodiments, a STAT3-binding substituent includes a DNA sequence identical (except that it may include one or more phosphodiester derivative linkage(s)) to the genomic DNA sequence phosphorylated (e.g. on Y705 or residue corresponding to human STAT3 Y705) STAT3 binds when modulating transcription. In embodiments, a STAT3-binding substituent is a DNA sequence identical (except that it may include one or more phosphodiester derivative linkage(s)) to the genomic DNA sequence phosphorylated (e.g. on Y705 or residue corresponding to human STAT3 Y705) STAT3 binds when modulating transcription. In embodiments, a STAT3-binding substituent includes a DNA sequence identical (except that it may include one or more phosphodiester derivative linkage(s)) to the genomic DNA sequence a STAT3 dimer binds when modulating transcription. In embodiments, a STAT3-binding substituent is a DNA sequence identical (except that it may include one or more phosphodiester derivative linkage(s)) to the genomic DNA sequence a STAT3 dimer binds when modulating transcription. In embodiments, a STAT3-binding substituent includes a DNA sequence identical (except that it may include one or more phosphodiester derivative linkage(s)) to the genomic DNA sequence a phosphorylated (e.g. on Y705 or residue corresponding to human STAT3 Y705) STAT3 dimer binds when modulating transcription. In embodiments, a STAT3-binding substituent is a DNA sequence identical (except that it may include one or more phosphodiester derivative linkage(s)) to the genomic DNA sequence a phosphorylated (e.g. on Y705 or residue corresponding to human STAT3 Y705) STAT3 dimer binds when modulating transcription. In embodiments, a STAT3-binding substituent includes the DNA (e.g. including phosphodiester linkages and/or phosphodiester derivative linkages) sequence CATTTCCCGTAAATC (SEQ ID NO:1). In embodiments, a STAT3-binding substituent includes the complement to DNA (e.g. including phosphodiester linkages and/or phosphodiester derivative linkages) sequence CATTTCCCGTAAATC (SEQ ID NO:1). In embodiments, a STAT3-binding substituent includes the DNA (e.g. including phosphodiester linkages and/or phosphodiester derivative linkages) sequence CATTTCCCGTAAATC (SEQ ID NO:1) and the complement of the sequence. In embodiments, a STAT3-binding substituent includes the DNA (e.g. including phosphodiester linkages and/or phosphodiester derivative linkages) sequence ATTTCCCGTAAAT (SEQ ID NO:2). In embodiments, a STAT3-binding substituent includes the complement to DNA (e.g. including phosphodiester linkages and/or phosphodiester derivative linkages) sequence ATTTCCCGTAAAT (SEQ ID NO:2). In embodiments, a STAT3-binding substituent includes the DNA (e.g. including phosphodiester linkages and/or phosphodiester derivative linkages) sequence ATTTCCCGTAAAT (SEQ ID NO:2) and the complement of the sequence. In embodiments, a STAT3-binding substituent includes the DNA (e.g. including phosphodiester linkages and/or phosphodiester derivative linkages) sequence TTTCCCGTAAA (SEQ ID NO:3). In embodiments, a STAT3-binding substituent includes the complement to DNA (e.g. including phosphodiester linkages and/or phosphodiester derivative linkages) sequence TTTCCGTAAA (SEQ ID NO:3). In embodiments, a STAT3-binding substituent includes the DNA (e.g. including phosphodiester linkages and/or phosphodiester derivative linkages) sequence TTTCCCGTAAA (SEQ ID NO:3) and the complement of the sequence. In embodiments, a STAT3-binding substituent includes the DNA (e.g. including phosphodiester linkages and/or phosphodiester derivative linkages) sequence TTCCCGTAA (SEQ ID NO:4). In embodiments, a STAT3-binding substituent includes the complement to DNA (e.g. including phosphodiester linkages and/or phosphodiester derivative linkages) sequence TTCCCGTAA (SEQ ID NO:4). In embodiments, a STAT3-binding substituent includes the DNA (e.g. including phosphodiester linkages and/or phosphodiester derivative linkages) sequence TTCCCGTAA (SEQ ID NO:4) and the complement of the sequence. In embodiments, a STAT3-binding substituent includes the DNA (e.g. including phosphodiester linkages and/or phosphodiester derivative linkages) sequence TTCCGGGAA (SEQ ID NO:5). In embodiments, a STAT3-binding substituent includes the complement to DNA (e.g. including phosphodiester linkages and/or phosphodiester derivative linkages) sequence TTCCGGGAA (SEQ ID NO:5). In embodiments, a STAT3-binding substituent includes the DNA (e.g. including phosphodiester linkages and/or phosphodiester derivative linkages) sequence TTCCGGGAA (SEQ ID NO:5) and the complement of the sequence.

As used herein, the term "preferentially binds" as applied to a STAT-binding substituent (e.g. STAT1-, STAT2-, STAT3-, STAT4-, STAT5A-, STAT5B-, or STAT6-binding substituent) or STAT3-binding nucleic acid substituent (e.g. STAT3-binding DNA substituent) binding to a specific form of a STAT transcription factor (e.g. STAT1, STAT2, STAT3, STAT4, STAT5A, STAT5B, or STAT6) or STAT3 respectively, means binds more strongly to the specific form compared to the binding to another form of a STAT transcription factor (e.g. STAT1, STAT2, STAT3, STAT4, STAT5A, STAT5B, or STAT6). In embodiments, preferentially binds means binds more strongly to the specific form compared to the binding to other forms of a STAT transcription factor (e.g. STAT1, STAT2, STAT3, STAT4, STAT5A, STAT5B, or STAT6). In embodiments, preferential binding is measured as an IC50. In embodiments, preferential binding is measured as a dissociation constant. In embodiments, preferential binding is measured as an association constant. In embodiments, preferential binding is measured as an on rate. In embodiments, preferential binding is measured as an off rate. In embodiments, preferential binding is measured as a lowered concentration needed to bind to the preferred form to the same extent as binding to a non-preferred form at a greater concentration. In embodiments, preferentially binds means binds 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, or 1,000,000-fold greater to the preferred form compared to another form. In embodiments, preferentially binds means binds 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, or 1,000,000-fold greater to the preferred form compared to other forms.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

Compounds

In an aspect is provided a compound including a TLR-binding (e.g. endosome-associated TLR- (endosomal TLR-), TLR3-, TLR7-, TLR8-, or TLR9-binding) nucleic acid substituent conjugated to a STAT-binding substituent (e.g. STAT1-, STAT2-, STAT3-, STAT4-, STAT5A-, STAT5B-, or STAT6-binding substituent). In embodiments the compound includes a TLR9-binding DNA substituent conjugated to a STAT-binding substituent (e.g. STAT1-, STAT2-, STAT3-, STAT4-, STAT5A-, STAT5B-, or STAT6-binding substituent). In embodiments, the compound includes a TLR9-binding DNA substituent conjugated to a STAT3-binding substituent. In embodiments, the STAT-binding substituent is a STAT1-binding substituent. In embodiments, the STAT-binding substituent is a STAT2-binding substituent. In embodiments, the STAT-binding substituent is a STAT3-binding substituent. In embodiments, the STAT-binding substituent is a STAT4-binding substituent. In embodiments, the STAT-binding substituent is a STAT5A-binding substituent. In embodiments, the STAT-binding substituent is a STAT5B-binding substituent. In embodiments, the STAT-binding substituent is a STAT6-binding substituent. In embodiments, the TLR-binding nucleic acid substituent is an endosome-associated TLR-binding nucleic acid substituent. In embodiments, the TLR-binding nucleic acid substituent is a TLR3-binding nucleic acid substituent. In embodiments, the TLR-binding nucleic acid substituent is a TLR7-binding nucleic acid substituent. In embodiments, the TLR-binding nucleic acid substituent is a TLR8-binding nucleic acid substituent. In embodiments, the TLR-binding nucleic acid substituent is a TLR9-binding nucleic acid substituent. In embodiments, the TLR-binding nucleic acid substituent is a TLR9-binding DNA substituent. In embodiments, the STAT-binding substituent is a STAT-binding nucleic acid substituent. In embodiments, the STAT-binding substituent is a STAT3-binding nucleic acid substituent (e.g. STAT3-binding DNA substituent). In embodiments, the STAT-binding substituent is a STAT3-binding DNA substituent.

In embodiments, the compound includes a CpG motif. In embodiments, the compound includes an unmethylated CpG motif. In embodiments, the compound includes a CpG motif wherein the CpG is not methylated. In embodiments, the compound includes a nucleic acid sequence capable of forming a G-quadruplex. In embodiments, the compound includes a DNA sequence capable of forming a G-quadruplex. In embodiments, the compound includes a Class A CpG DNA sequence. In embodiments, the compound includes a Class B CpG DNA sequence. In embodiments, the compound includes a C-type CpG DNA sequence. In embodiments, the compound binds an endosomal TLR. In embodiments, the compound preferentially binds an endosomal TLR over other TLR. In embodiments, the compound specifically binds an endosomal TLR. In embodiments, the compound binds TLR3. In embodiments, the compound preferentially binds TLR3 over other TLR. In embodiments, the compound specifically binds TLR3. In embodiments, the compound binds TLR7. In embodiments, the compound preferentially binds TLR7 over other TLR. In embodiments, the compound specifically binds TLR7. In embodiments, the compound binds TLR8. In embodiments, the compound preferentially binds TLR8 over other TLR. In embodiments, the compound specifically binds TLR8. In embodiments, the compound binds TLR9. In embodiments, the compound preferentially binds TLR9 over other TLR. In embodiments, the compound specifically binds TLR9. In embodiments, the compound includes CpG, wherein C and G are nucleotides connected by a phosphodiester internucleotide linkage or phosphodiester derivative internucleotide linkage. In embodiments, the compound includes CpG, wherein C and G are nucleotides connected by a phosphodiester internucleotide linkage. In embodiments, the compound includes CpG, wherein C and G are nucleotides connected by a phosphodiester derivative internucleotide linkage. In embodiments, the CpG is unmethylated. In embodiments, the compound preferentially binds phosphorylated STAT (e.g. STAT1, STAT2, STAT3, STAT4, STAT5A, STAT5B, or STAT6) over unphosphorylated STAT (e.g. STAT1, STAT2, STAT3, STAT4, STAT5A, STAT5B, or STAT6). In embodiments, the compound binds phosphorylated STAT (e.g. STAT1, STAT2, STAT3, STAT4, STAT5A, STAT5B, or STAT6). In embodiments, the compound binds STAT3 phosphorylated on tyrosine 705. In embodiments, the compound binds a STAT transcription factor (e.g. STAT1, STAT2, STAT3, STAT4, STAT5A, STAT5B, or STAT6) phosphorylated on STAT1 Y701, STAT2, Y690, STAT3 Y705, STAT4 Y693, STAT5A Y694, STAT5B Y694, STAT6 Y641, or a residue corresponding to one of those residues. In embodiments, the compound binds human STAT (e.g. STAT1, STAT2, STAT3, STAT4, STAT5A, STAT5B, or STAT6). In embodiments, the compound binds STAT (e.g. STAT1, STAT2, STAT3, STAT4, STAT5A, STAT5B, STAT6, or combinations thereof) dimers. In embodiments, the compound binds dimers of phorphorylated STAT (e.g. STAT1, STAT2, STAT3, STAT4, STAT5A, STAT5B, STAT6, or combinations thereof) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues). In embodiments, the compound binds activated STAT (e.g. STAT1, STAT2, STAT3, STAT4, STAT5A, STAT5B, or STAT6). In embodiments, the compound binds a scavenger receptor.

In embodiments, the compound enters a cell following administration (e.g. to a patient, to the blood stream of a patient, or to the extracellular milieu of the cell) in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the compound enters a cell following administration (e.g. to a patient, to the blood stream of a patient, or to the extracellular milieu of the cell) in less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the compound enters a cell following administration (e.g. to a patient, to the blood stream of a patient, or to the extracellular milieu of the cell) without co-administration of an agent to facilitate transfection (e.g. an agent with the sole purpose of assisting the compound to enter a cell). In embodiments, the cell is a plasmacytoid dendritic cell, myeloid dendritic cell, myeloid-derived suppressor cell, granulocytic myeloid-derived suppressor cell, macrophage, B cell, activated NK cell, or activated neutrophil. In embodiments, the cell is in the brain, an organ, bone, or bone marrow of a subject.

In embodiments, the compound is not degraded (e.g. in a patient, in the blood stream, at the site of administration, or in the extracellular milieu) for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the compound is not degraded (e.g. in a patient, in the blood stream, at the site of administration, or in the extracellular milieu) for an average of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the compound is not degraded (e.g. in a patient, in the blood stream, at the site of administration, or in the extracellular milieu) for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours.

In embodiments, the STAT3-binding nucleic acid substituent (e.g. STAT3-binding DNA substituent) includes a first STAT3-binding nucleic acid sequence (e.g. STAT3-binding DNA sequence) bound to a second STAT3-binding nucleic acid sequence (e.g. STAT3-binding DNA sequence) by a spacer. In embodiments, the STAT3-binding nucleic acid substituent (e.g. STAT3-binding DNA substituent) includes a first STAT3-binding nucleic acid sequence (e.g. STAT3-binding DNA sequence) covalently bound to a second STAT3-binding nucleic acid sequence (e.g. STAT3-binding DNA sequence) by a spacer. In embodiments, the STAT-binding nucleic acid substituent (e.g. STAT1-, STAT2-, STAT3-, STAT4-, STAT5A-, STAT5B-, or STAT6-binding nucleic acid substituent) includes a first STAT-binding nucleic acid sequence (e.g. STAT1-, STAT2-, STAT3-, STAT4-, STAT5A-, STAT5B-, or STAT6-binding nucleic acid sequence) bound to a second STAT-binding nucleic acid sequence (e.g. STAT1-, STAT2-, STAT3-, STAT4-, STAT5A-, STAT5B-, or STAT6-binding nucleic acid sequence) by a spacer. In embodiments, the STAT-binding nucleic acid substituent (e.g. STAT1-, STAT2-, STAT3-, STAT4-, STAT5A-, STAT5B-, or STAT6-binding nucleic acid substituent) includes a first STAT-binding nucleic acid sequence (e.g. STAT1-, STAT2-, STAT3-, STAT4-, STAT5A-, STAT5B-, or STAT6-binding nucleic acid sequence) covalently bound to a second STAT-binding nucleic acid sequence (e.g. STAT1-, STAT2-, STAT3-, STAT4-, STAT5A-, STAT5B-, or STAT6-binding nucleic acid sequence) by a spacer.

In embodiments, the STAT3-binding DNA substituent includes a first STAT3-binding DNA sequence bound to a second STAT3-binding DNA sequence by a spacer. In embodiments, the STAT3-binding DNA substituent includes a first STAT3-binding DNA sequence covalently bound to a second STAT3-binding DNA sequence by a spacer. In embodiments, the STAT-binding DNA substituent (e.g. STAT1-, STAT2-, STAT3-, STAT4-, STAT5A-, STAT5B-, or STAT6-binding DNA substituent) includes a first STAT-binding DNA sequence (e.g. STAT1-, STAT2-, STAT3-, STAT4-, STAT5A-, STAT5B-, or STAT6-binding DNA sequence) bound to a second STAT-binding DNA sequence (e.g. STAT1-, STAT2-, STAT3-, STAT4-, STAT5A-, STAT5B-, or STAT6-binding DNA sequence) by a spacer. In embodiments, the STAT-binding DNA substituent (e.g. STAT1-, STAT2-, STAT3-, STAT4-, STAT5A-, STAT5B-, or STAT6-binding DNA substituent) includes a first STAT-binding DNA sequence (e.g. STAT1-, STAT2-, STAT3-, STAT4-, STAT5A-, STAT5B-, or STAT6-binding DNA sequence) covalently bound to a second STAT-binding DNA sequence (e.g. STAT1-, STAT2-, STAT3-, STAT4-, STAT5A-, STAT5B-, or STAT6-binding DNA sequence) by a spacer.

In embodiments, the TLR9-binding DNA substituent includes a CpG motif. In embodiments, the TLR9-binding DNA substituent includes an unmethylated CpG motif. In embodiments, the TLR9-binding DNA substituent includes a CpG motif wherein the CpG is not methylated. In embodiments, the TLR9-binding DNA substituent includes a DNA sequence capable of forming a G-quadruplex. In embodiments, the TLR9-binding DNA substituent includes a Class A CpG DNA sequence. In embodiments, the TLR9-binding DNA substituent includes a Class B CpG DNA sequence. In embodiments, the TLR9-binding DNA substituent includes a C-type CpG DNA sequence.

In embodiments, the TLR-binding DNA substituent binds TLR9. In embodiments, the TLR-binding DNA substituent preferentially binds TLR9 over other TLR. In embodiments, the TLR-binding DNA substituent specifically binds TLR9. In embodiments, the TLR-binding DNA substituent includes CpG, wherein C and G are nucleotides connected by a phosphodiester internucleotide linkage or phosphodiester derivative internucleotide linkage. In embodiments, the compound includes CpG, wherein C and G are nucleotides connected by a phosphodiester internucleotide linkage. In embodiments, the compound includes CpG, wherein C and G are nucleotides connected by a phosphodiester derivative internucleotide linkage. In embodiments, the CpG is unmethylated. In embodiments, the TLR-binding DNA substituent is a Class A CpG oligodeoxynucleotide (ODN). In embodiments, the TLR-binding DNA substituent is a Class B CpG oligodeoxynucleotide (ODN). In embodiments, the TLR-binding DNA substituent is a Class C CpG oligodeoxynucleotide (ODN). In embodiments, the TLR-binding DNA substituent is ODN 1585, ODN 2216, ODN D19, or ODN 2336. In embodiments, the TLR-binding DNA substituent is ODN 1668, ODN 1826, ODN 2006, or ODN 2007. In embodiments, the TLR-binding DNA substituent is ODN 2395 or ODN M362. In embodiments, the TLR-binding DNA substituent is a derivative of ODN 1585, ODN 2216, ODN D19, ODN 2336, ODN 1668, ODN 1826, ODN 2006, ODN 2007, ODN 2395 or ODN M362. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide substitutions (e.g. A, C, G, or T substituted with a different nucleotide). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) internucleotide linkage replacements (e.g. phosphodiester replaced with a phosphodiester derivative or a phosphodiester derivative replaced with a phosphodiester). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide deletions. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide additions.

A spacer is a bond, nucleic acid sequence, two nucleic acid sequences, DNA sequence, two DNA sequences, nucleic acid analog sequence, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the spacer is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the spacer is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the spacer is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the spacer is an unsubstituted $C_1$-$C_{20}$ alkylene. In embodiments, the spacer is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the spacer is a substituted or unsubstituted $C_1$-$C_{40}$ alkylene. In embodiments, the spacer is a substituted or unsubstituted 2 to 40 membered heteroalkylene. In embodiments, the spacer is a substituted 2 to 40 membered heteroalkylene. In embodiments, the spacer includes alkyl phosphates (e.g., propyl phosphates). In embodiments, the spacer consists of alkyl phosphates (e.g., propyl phosphates) bonded to the reminder of the compound by phosphates at both ends. In embodiments, the spacer consists of 1-5 alkyl phosphates (e.g., propyl phosphates) bonded to the reminder of the compound by phosphates at both ends. In embodiments, the spacer consists of 1-4 alkyl phosphates (e.g., propyl phosphates) bonded to the reminder of the compound by phosphates at both ends. In embodiments, the spacer consists of 4 alkyl phosphates (e.g., propyl phosphates) bonded to the reminder of the compound by phosphates at both ends. A person having ordinary skill in the art will recognize that a spacer consisting of alkyl phosphates that is bonded to the remainder of the compound by phosphates on both ends will have one more phosphate than alkylene groups (e.g., a spacer consisting of 4 alkyl phosphates that is bonded to the reminder of the compound by phosphates at both ends will have five phosphates and four alkyl groups with alternating phosphate groups and alkyl groups).

In embodiments, the spacer includes a first single nucleic acid strand connected to the first STAT3-binding nucleic acid sequence (e.g. STAT3-binding DNA sequence) and a second single nucleic acid strand connected to the second STAT3-binding nucleic acid sequence (e.g. STAT3-binding DNA sequence), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In embodiments, the spacer includes a first single nucleic acid strand connected to the first STAT-binding nucleic acid sequence (e.g. STAT1-, STAT2-, STAT3-, STAT4-, STAT5A-, STAT5B-, or STAT6-binding nucleic acid sequence) and a second single nucleic acid strand connected to the STAT-binding nucleic acid sequence (e.g. STAT1-, STAT2-, STAT3-, STAT4-, STAT5A-, STAT5B-, or STAT6-binding nucleic acid sequence), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In embodiments, the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary nucleic acid sequence in the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the first and second single nucleic acid strands in the hybridized nucleic acid overhang are complementary throughout their entire lengths. In embodiments, the spacer is an unsubstituted $C_1$-$C_{20}$ alkylene. In embodiments, the spacer is an unsubstituted linear $C_1$-$C_{20}$ alkylene. In embodiments, the spacer is an unsubstituted $C_3$-$C_{21}$ alkylene. In embodiments, the spacer is an unsubstituted $C_3$-$C_{18}$ alkylene. In embodiments, the spacer is an unsubstituted linear $C_3$-$C_{15}$ alkylene. In embodiments, the spacer is an unsubstituted linear $C_6$-$C_{21}$ alkylene. In embodiments, the spacer is an unsubstituted linear $C_9$-$C_{21}$ alkylene. In embodiments, the spacer is an unsubstituted linear $C_9$-$C_{18}$ alkylene. In embodiments, the spacer is an unsubstituted linear $C_9$-$C_{15}$ alkylene. In embodiments, the spacer is an unsubstituted linear $C_{12}$-$C_{15}$ alkylene. In embodiments, the spacer is an unsubstituted linear $C_{12}$ alkylene. In embodiments, the spacer is an unsubstituted linear $C_{13}$ alkylene. In embodiments, the spacer is an unsubstituted linear $C_{14}$ alkylene. In embodiments, the spacer is an unsubstituted linear $C_{15}$ alkylene. A STAT3-binding nucleic acid (e.g. DNA) sequence or STAT-binding nucleic acid (e.g. DNA) sequence is a nucleic acid (e.g. DNA) including phosphodiester linkages, phosphodiester derivative linkages, and/or nucleic acid analogs, capable of binding STAT3 or a STAT transcription factor respectively. In embodiments, the spacer is a substituted 2 to 40 membered heteroalkylene. In embodiments, the spacer is a substituted 10 to 50 membered heteroalkylene. In embodiments, the spacer is a substituted 20 to 40 membered heteroalkylene. In embodiments, the spacer is a substituted 25 to 40 membered heteroalkylene. In embodiments, the spacer is a substituted 30 to 40 membered heteroalkylene. In embodiments, the spacer is a substituted liner 2 to 40 membered heteroalkylene. In embodiments, the spacer is a substituted liner 10 to 50 membered heteroalkylene. In embodiments, the spacer is a substituted liner 20 to 40 membered heteroalkylene. In embodiments, the spacer is a substituted liner 25 to 40 membered heteroalkylene. In embodiments, the spacer is a substituted liner 30 to 40 membered heteroalkylene.

In embodiments, the STAT-binding nucleic acid substituent (e.g. STAT1-, STAT2-, STAT3-, STAT4-, STAT5A-, STAT5B-, or STAT6-binding nucleic acid substituent) preferentially binds phosphorylated STAT (e.g. STAT1, STAT2, STAT3, STAT4, STAT5A, STAT5B, or STAT6) over unphosphorylated STAT (e.g. STAT1, STAT2, STAT3, STAT4, STAT5A, STAT5B, or STAT6). In embodiments, the first STAT-binding nucleic acid sequence (e.g. STAT1-, STAT2-, STAT3-, STAT4-, STAT5A-, STAT5B-, or STAT6-binding nucleic acid sequence) and second STAT-binding nucleic acid sequence (e.g. STAT1-, STAT2-, STAT3-, STAT4-, STAT5A-, STAT5B-, or STAT6-binding nucleic acid sequence) form a double-stranded STAT-binding nucleic acid sequence (e.g. STAT1-, STAT2-, STAT3-, STAT4-, STAT5A-, STAT5B-, or STAT6-binding nucleic acid sequence). In embodiments, the STAT-binding nucleic acid substituent (e.g. STAT1-, STAT2-, STAT3-, STAT4-, STAT5A-, STAT5B-, or STAT6-binding nucleic acid substituent) includes a STAT-binding nucleic acid sequence (e.g. STAT1-, STAT2-, STAT3-, STAT4-, STAT5A-, STAT5B-, or STAT6-binding nucleic acid sequence) covalently bonded to a terminal moiety. In embodiments, the STAT-binding nucleic acid substituent (e.g. STAT1-, STAT2-, STAT3-, STAT4-, STAT5A-, STAT5B-, or STAT6-binding nucleic acid substituent) binds phosphorylated STAT (e.g. STAT1, STAT2, STAT3, STAT4, STAT5A, STAT5B, or STAT6). In embodiments, the STAT3-binding nucleic acid substituent binds STAT3 phosphorylated on tyrosine 705. In embodiments, the STAT-binding nucleic acid substituent (e.g. STAT1-, STAT2-, STAT3-, STAT4-, STAT5A-, STAT5B-, or STAT6-binding nucleic acid substituent) binds a STAT transcription factor (e.g. STAT1, STAT2, STAT3, STAT4, STAT5A, STAT5B, or STAT6) phosphorylated on STAT1 Y701, STAT2, Y690, STAT3 Y705, STAT4 Y693, STAT5A Y694, STAT5B Y694, STAT6 Y641, or a residue corresponding to one of those residues. In embodiments, the STAT-binding nucleic acid substituent (e.g. STAT1-, STAT2-, STAT3-, STAT4-, STAT5A-, STAT5B-, or STAT6-binding nucleic acid substituent) binds human STAT (e.g. STAT1, STAT2, STAT3, STAT4, STAT5A, STAT5B, or STAT6). In embodiments, the STAT-binding nucleic acid substituent (e.g. STAT1-, STAT2-, STAT3-, STAT4-, STAT5A-, STAT5B-, or STAT6-binding nucleic acid substituent) binds STAT (e.g. STAT1, STAT2, STAT3, STAT4, STAT5A, STAT5B, STAT6, or combinations thereof) dimers. In embodiments, the STAT-binding nucleic acid substituent (e.g. STAT1-, STAT2-, STAT3-, STAT4-, STAT5A-, STAT5B-, or STAT6-binding nucleic acid substituent) binds dimers of phorphorylated STAT (e.g.

STAT1, STAT2, STAT3, STAT4, STAT5A, STAT5B, STAT6, or combinations thereof) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues). In embodiments, the STAT-binding nucleic acid substituent (e.g. STAT1-, STAT2-, STAT3-, STAT4-, STAT5A-, STAT5B-, or STAT6-binding nucleic acid substituent) binds activated STAT (e.g. STAT1, STAT2, STAT3, STAT4, STAT5A, STAT5B, or STAT6). In embodiments, the STAT-binding nucleic acid substituent (e.g. STAT1-, STAT2-, STAT3-, STAT4-, STAT5A-, STAT5B-, or STAT6-binding nucleic acid substituent) includes the nucleic acid sequence recognized by a STAT transcription factor (e.g. apo-STAT (e.g. STAT1, STAT2, STAT3, STAT4, STAT5A, STAT5B, or STAT6), activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In embodiments, the STAT-binding nucleic acid substituent (e.g. STAT1-, STAT2-, STAT3-, STAT4-, STAT5A-, STAT5B-, or STAT6-binding nucleic acid substituent) includes the nucleic acid sequence contacted by a STAT transcription factor (e.g. STAT1, STAT2, STAT3, STAT4, STAT5A, STAT5B, or STAT6) that is associated with STAT (e.g. STAT1, STAT2, STAT3, STAT4, STAT5A, STAT5B, or STAT6) transcriptional activation activity). In embodiments, the STAT-binding nucleic acid substituent (e.g. STAT1-, STAT2-, STAT3-, STAT4-, STAT5A-, STAT5B-, or STAT6-binding nucleic acid substituent) includes a STAT-binding derivative of the nucleic acid sequence recognized by a STAT transcription factor (e.g. apo-STAT3, activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In embodiments, the STAT-binding nucleic acid substituent (e.g. STAT1-, STAT2-, STAT3-, STAT4-, STAT5A-, STAT5B-, or STAT6-binding nucleic acid substituent) includes a STAT-binding derivative of the nucleic acid sequence contacted by a STAT transcription factor and associated with STAT (e.g. STAT1, STAT2, STAT3, STAT4, STAT5A, STAT5B, or STAT6) transcriptional activation activity). In embodiments, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide substitutions (e.g. A, C, G, or T substituted with a different nucleotide). In embodiments, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) internucleotide linkage replacements (e.g. phosphodiester replaced with a phosphodiester derivative or a phosphodiester derivative replaced with a phosphodiester). In embodiments, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) nucleotide deletions. In embodiments, the STAT-binding derivative of the nucleic acid sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide additions.

In embodiments, the spacer includes a first single DNA strand connected to the first STAT3-binding DNA sequence and a second single DNA strand connected to the second STAT3-binding DNA sequence, wherein the first DNA strand includes a DNA sequence that is complementary to a DNA sequence included in the second single DNA strand (both single DNA strands including their respective complementary sequences being collectively a "hybridized DNA overhang". In embodiments, the spacer includes a first single DNA strand connected to the first STAT-binding DNA sequence (e.g. STAT1-, STAT2-, STAT3-, STAT4-, STAT5A-, STAT5B-, or STAT6-binding DNA sequence) and a second single DNA strand connected to the STAT-binding DNA sequence (e.g. STAT1-, STAT2-, STAT3-, STAT4-, STAT5A-, STAT5B-, or STAT6-binding DNA sequence), wherein the first DNA strand includes a DNA sequence that is complementary to a DNA sequence included in the second single DNA strand (both single DNA strands including their respective complementary sequences being collectively a "hybridized DNA overhang". In embodiments, the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary DNA sequence in the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. A STAT3-binding DNA sequence or STAT-binding DNA sequence is a DNA including phosphodiester linkages, phosphodiester derivative linkages, and/or nucleic acid analogs, capable of binding STAT3 or a STAT transcription factor respectively.

In embodiments, the STAT-binding DNA substituent (e.g. STAT1-, STAT2-, STAT3-, STAT4-, STAT5A-, STAT5B-, or STAT6-binding DNA substituent) preferentially binds phosphorylated STAT (e.g. STAT1, STAT2, STAT3, STAT4, STAT5A, STAT5B, or STAT6) over unphosphorylated STAT (e.g. STAT1, STAT2, STAT3, STAT4, STAT5A, STAT5B, or STAT6). In embodiments, the first STAT-binding DNA sequence (e.g. STAT1-, STAT2-, STAT3-, STAT4-, STAT5A-, STAT5B-, or STAT6-binding DNA sequence) and second STAT-binding DNA sequence (e.g. STAT1-, STAT2-, STAT3-, STAT4-, STAT5A-, STAT5B-, or STAT6-binding DNA sequence) form a double-stranded STAT-binding DNA sequence (e.g. STAT1-, STAT2-, STAT3-, STAT4-, STAT5A-, STAT5B-, or STAT6-binding DNA sequence). In embodiments, the STAT-binding DNA substituent (e.g. STAT1-, STAT2-, STAT3-, STAT4-, STAT5A-, STAT5B-, or STAT6-binding DNA substituent) includes a STAT-binding DNA sequence (e.g. STAT1-, STAT2-, STAT3-, STAT4-, STAT5A-, STAT5B-, or STAT6-binding DNA sequence) covalently bonded to a terminal moiety. In embodiments, the STAT-binding DNA substituent (e.g. STAT1-, STAT2-, STAT3-, STAT4-, STAT5A-, STAT5B-, or STAT6-binding DNA substituent) binds phosphorylated STAT (e.g. STAT1, STAT2, STAT3, STAT4, STAT5A, STAT5B, or STAT6). In embodiments, the STAT3-binding DNA substituent binds STAT3 phosphorylated on tyrosine 705. In embodiments, the STAT-binding DNA substituent (e.g. STAT1-, STAT2-, STAT3-, STAT4-, STAT5A-, STAT5B-, or STAT6-binding DNA substituent) binds a STAT transcription factor (e.g. STAT1, STAT2, STAT3, STAT4, STAT5A, STAT5B, or STAT6) phosphorylated on STAT1 Y701, STAT2, Y690, STAT3 Y705, STAT4 Y693, STAT5A Y694, STAT5B Y694, STAT6 Y641, or a residue corresponding to one of those residues. In embodiments, the STAT-binding DNA substituent (e.g. STAT1-, STAT2-, STAT3-, STAT4-, STAT5A-, STAT5B-, or STAT6-binding DNA substituent) binds human STAT (e.g. STAT1, STAT2, STAT3, STAT4, STAT5A, STAT5B, or STAT6). In embodiments, the STAT-binding DNA substituent (e.g. STAT1-, STAT2-, STAT3-, STAT4-, STAT5A-, STAT5B-, or STAT6-binding DNA substituent) binds STAT (e.g. STAT1, STAT2, STAT3, STAT4, STAT5A, STAT5B, STAT6, or combinations thereof) dimers. In embodiments, the STAT-binding DNA substituent (e.g. STAT1-, STAT2-, STAT3-, STAT4-, STAT5A-, STAT5B-, or STAT6-binding DNA substituent) binds dimers of phorphorylated STAT (e.g. STAT1, STAT2, STAT3, STAT4, STAT5A, STAT5B, STAT6, or combinations thereof) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues). In embodiments, the STAT-binding DNA substituent (e.g. STAT1-, STAT2-, STAT3-, STAT4-, STAT5A-, STAT5B-, or STAT6-binding DNA substituent) binds activated STAT (e.g. STAT1, STAT2, STAT3, STAT4, STAT5A, STAT5B or STAT6). In embodiments, the STAT-binding DNA substituent (e.g. STAT1-, STAT2-, STAT3-, STAT4-, STAT5A-, STAT5B-, or STAT6-binding DNA substituent) includes the DNA sequence recognized by a STAT transcription factor (e.g. apo-STAT (e.g. STAT1, STAT2, STAT3, STAT4, STAT5A, STAT5B, or STAT6), activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In embodiments, the STAT-binding DNA substituent (e.g. STAT1-, STAT2-, STAT3-, STAT4-, STAT5A-, STAT5B-, or STAT6-binding DNA substituent) includes the DNA sequence contacted by a STAT transcription factor associated with STAT (e.g. STAT1, STAT2, STAT3, STAT4, STAT5A, STAT5B, or STAT6) transcriptional activation activity). In embodiments, the STAT-binding DNA substituent (e.g. STAT1-, STAT2-, STAT3-, STAT4-, STAT5A-, STAT5B-, or STAT6-binding DNA substituent) includes a STAT-binding derivative of the DNA sequence recognized by a STAT transcription factor (e.g. apo-STAT (e.g. STAT1, STAT2, STAT3, STAT4, STAT5A, STAT5B, or STAT6), activated STAT (e.g. STAT1, STAT2, STAT3, STAT4, STAT5A, STAT5B, or STAT6), phosphorylated STAT (e.g. STAT1, STAT2, STAT3, STAT4, STAT5A, STAT5B, or STAT6) (e.g. phosphorylated on STAT1 Y701, STAT2, Y690, STAT3 Y705, STAT4 Y693, STAT5A Y694, STAT5B Y694, STAT6 Y641, or a residue corresponding to one of those residues), or STAT (e.g. STAT1, STAT2, STAT3, STAT4, STAT5A, STAT5B, STAT6, or combinations thereof) dimers). In embodiments, the STAT-binding DNA substituent (e.g. STAT1-, STAT2-, STAT3-, STAT4-, STAT5A-, STAT5B-, or STAT6-binding DNA substituent) includes a STAT-binding derivative of the DNA sequence contacted by a STAT transcription factor (e.g. STAT1, STAT2, STAT3, STAT4, STAT5A, STAT5B, or STAT6) associated with STAT (e.g. STAT1, STAT2, STAT3, STAT4, STAT5A, STAT5B, or STAT6) transcriptional activation activity). In embodiments, the STAT-binding derivative (e.g. STAT1-, STAT2-, STAT3-, STAT4-, STAT5A-, STAT5B-, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide substitutions (e.g. A, C, G, or T substituted with a different nucleotide). In embodiments, the STAT-binding derivative (e.g. STAT1-, STAT2-, STAT3-, STAT4-, STAT5A-, STAT5B-, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) internucleotide linkage replacements (e.g. phosphodiester replaced with a phosphodiester derivative or a phosphodiester derivative replaced with a phosphodiester). In embodiments, the STAT-binding derivative (e.g. STAT1-, STAT2-, STAT3-, STAT4-, STAT5A-, STAT5B-, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) nucleotide deletions. In embodiments, the STAT-binding derivative (e.g. STAT1-, STAT2-, STAT3-, STAT4-, STAT5A-, STAT5B-, or STAT6-binding derivative) of the DNA sequence recognized by a STAT transcription factor (e.g. STAT1, STAT2, STAT3, STAT4, STAT5A, STAT5B, or STAT6) includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide additions.

A terminal moiety is a chemically reactive moiety, detectable moiety, therapeutic moiety (e.g. anti-cancer agent or anti-viral agent), nucleic acid sequence, DNA sequence, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, a terminal moiety is a chemically reactive moiety, detectable moiety, therapeutic moiety (e.g. anti-cancer agent or anti-viral agent), nucleic acid sequence, DNA sequence, nucleic acid analogs, $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, or $R^1$-substituted or unsubstituted heteroaryl. In embodiments, a terminal moiety is a detectable moiety. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, a terminal moiety is a therapeutic moiety (e.g. anti-cancer agent or anti-viral agent).

In embodiments, the terminal moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the terminal moiety is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, the terminal moiety is a substituted $C_1$-$C_{40}$ alkyl, substituted 2 to 40 membered heteroalkyl, substituted $C_3$-$C_8$ cycloalkyl, substituted 3 to 8 membered heterocycloalkyl, substituted $C_6$-$C_{10}$ aryl, or substituted 5 to 10 membered heteroaryl. In embodiments, the terminal moiety is an $R^1$-substituted $C_1$-$C_{40}$ alkyl, $R^1$-substituted 2 to 40 membered heteroalkyl, $R^1$-substituted $C_3$-$C_8$ cycloalkyl, $R^1$-substituted 3 to 8 membered heterocycloalkyl, $R^1$-substituted $C_6$-$C_{10}$ aryl, or $R^1$-substituted 5 to 10 membered heteroaryl. In embodiments, the terminal moiety is an $R^1$-substituted $C_1$-$C_{40}$ alkyl. In embodiments, the terminal moiety is an -(unsubstituted $C_1$-$C_{40}$ alkylene)-$R^1$. In embodiments, the terminal moiety is an -(unsubstituted linear $C_1$-$C_{40}$ alkylene)-$R^1$. In embodiments, the terminal moiety is an -(unsubstituted $C_3$-$C_{21}$ alkylene)-$R^1$. In embodiments, the terminal moiety is an -(unsubstituted $C_3$-$C_{18}$ alkylene)-$R^1$. In embodiments, the terminal moiety is an -(unsubstituted linear $C_3$-$C_{15}$ alkylene)-$R^1$. In embodiments, the terminal moiety is an -(unsubstituted linear $C_6$-$C_{21}$ alkylene)-$R^1$. In embodiments, the terminal moiety is an -(unsubstituted linear $C_9$-$C_{21}$ alkylene)-$R^1$. In embodiments, the terminal moiety is an -(unsubstituted linear $C_9$-$C_{18}$ alkylene)-$R^1$. In embodiments, the terminal moiety is an -(unsubstituted linear $C_9$-$C_{15}$ alkylene)-$R^1$. In embodiments, the terminal moiety is an -(unsubstituted linear $C_{12}$-$C_{15}$ alkylene)-$R^1$. In embodiments, the terminal moiety is an -(unsubstituted linear $C_{12}$ alkylene)-$R^1$. In embodiments, the terminal moiety is an -(unsubstituted linear $C_{13}$ alkylene)-$R^1$. In embodiments, the terminal moiety is an -(unsubstituted linear $C_{14}$ alkylene)-$R^1$. In embodiments, the terminal moiety is an -(unsubstituted linear $C_{15}$ alkylene)-$R^1$. In embodiments, the terminal moiety is an $R^1$-substituted 2 to 40 membered heteroalkyl. In embodiments, the terminal moiety is an -(unsubstituted 2 to 40 membered heteroalkylene)-$R^1$. In embodiments, the terminal moiety is a -(substituted linear 2 to 40 membered heteroalkylene)-$R^1$. In embodiments, the terminal moiety is a -(substituted 5 to 40 membered heteroalkylene)-$R^1$. In embodiments, the terminal moiety is a -(substituted 10 to 40 membered heteroalkylene)-$R^1$. In embodiments, the terminal moiety is a -(substituted 15 to 40 membered heteroalkylene)-$R^1$. In embodiments, the terminal moiety is a -(substituted 20 to 40 membered heteroalkylene)-$R^1$. In embodiments, the terminal moiety is a -(substituted 30 to 40 membered heteroalkylene)-$R^1$. In embodiments, the terminal moiety is a -(substituted 2 to 35 membered heteroalkylene)-$R^1$. In embodiments, the terminal moiety is a -(substituted 2 to 30 membered heteroalkylene)-$R^1$. In embodiments, the terminal moiety is a -(substituted 2 to 25 membered heteroalkylene)-$R^1$. In embodiments, the terminal moiety is a -(substituted 2 to 20 membered heteroalkylene)-$R^1$. In embodiments, the terminal moiety is a -(substituted 2 to 10 membered heteroalkylene)-$R^1$. In embodiments, the terminal moiety is a -(substituted 2 to 50 membered heteroalkylene)-$R^1$. In embodiments, the terminal moiety is a -(substituted 2 to 60 membered heteroalkylene)-$R^1$. In embodiments, the terminal moiety is a substituted 2 to 40 membered heteroalkyl. In embodiments, the terminal moiety is a substituted 10 to 50 membered heteroalkyl. In embodiments, the terminal moiety is a substituted 20 to 40 membered heteroalkyl. In embodiments, the terminal moiety is a substituted 25 to 40 membered heteroalkyl. In embodiments, the terminal moiety is a substituted 30 to 40 membered heteroalkyl.

In embodiments, $R^1$ is a detectable moiety or a therapeutic moiety. In embodiments, $R^1$ is a detectable moiety. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, $R^1$ is a therapeutic moiety (e.g. anti-cancer agent or anti-viral agent). In embodiments, $R^1$ is H. In embodiments, $R^1$ is oxo. In embodiments, $R^1$ is oxygen. In embodiments, $R^1$ is sulfur. In embodiments, $R^1$ is =S.

In embodiments, the compound includes a linker between the TLR-binding nucleic acid (e.g. endosomal TLR-, TLR3-, TLR7-, TLR8-, or TLR9-binding nucleic acid) substituent and the STAT-binding nucleic acid substituent (e.g. STAT1-, STAT2-, STAT3-, STAT4-, STAT5A-, STAT5B-, or STAT6-binding nucleic acid substituent). In embodiments, the compound includes a linker between the TLR9-binding DNA substituent and the STAT3-binding nucleic acid substituent. In embodiments, the compound includes a linker between the TLR9-binding nucleic acid substituent and the STAT-binding DNA substituent (e.g. STAT1-, STAT2-, STAT3-, STAT4-, STAT5A-, STAT5B-, or STAT6-binding DNA substituent). In embodiments, the STAT-binding nucleic acid substituent is a STAT1-binding nucleic acid substituent. In embodiments, the STAT-binding nucleic acid substituent is a STAT2-binding nucleic acid substituent. In embodiments, the STAT-binding nucleic acid substituent is a STAT3-binding nucleic acid substituent. In embodiments, the STAT-binding nucleic acid substituent is a STAT4-binding nucleic acid substituent. In embodiments, the STAT-binding nucleic acid substituent is a STAT5A-binding nucleic acid substituent. In embodiments, the STAT-binding nucleic acid substituent is a STAT5B-binding nucleic acid substituent. In embodiments, the STAT-binding nucleic acid substituent is a STAT6-binding nucleic acid substituent.

In embodiments, the compound includes a linker between the TLR-binding nucleic acid (e.g. endosomal TLR-, TLR3-, TLR7-, TLR8-, or TLR9-binding nucleic acid) substituent and the STAT-binding DNA substituent (e.g. STAT1-, STAT2-, STAT3-, STAT4-, STAT5A-, STAT5B-, or STAT6-binding DNA substituent). In embodiments, the compound includes a linker between the TLR9-binding DNA substituent and the STAT3-binding DNA substituent. In embodiments, the compound includes a linker between the TLR9-binding DNA substituent and the STAT-binding DNA substituent (e.g. STAT1-, STAT2-, STAT3-, STAT4-, STAT5A-, STAT5B-, or STAT6-binding DNA substituent). In embodiments, the STAT-binding DNA substituent is a STAT1-binding DNA substituent. In embodiments, the STAT-binding DNA substituent is a STAT2-binding DNA substituent. In embodiments, the STAT-binding DNA substituent is a STAT3-binding DNA substituent. In embodiments, the STAT-binding DNA substituent is a STAT4-binding DNA substituent. In embodiments, the STAT-binding DNA substituent is a STAT5A-binding DNA substituent. In embodiments, the STAT-binding DNA substituent is a STAT5B-binding DNA substituent. In embodiments, the STAT-binding DNA substituent is a STAT6-binding DNA substituent.

A linker is a bond, nucleic acid sequence, two nucleic acid sequences, DNA sequence, two DNA sequences, nucleic acid analog sequence, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the linker is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker is an unsubstituted $C_1$-$C_{20}$ alkylene. In embodiments, the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker is a substituted or unsubstituted $C_1$-$C_{40}$ alkylene. In embodiments, the linker is a substituted or unsubstituted 2 to 40 membered heteroalkylene. In embodiments, the linker is a substituted 2 to 40 membered heteroalkylene. In embodiments, the linker includes alkyl phosphates (e.g., propyl phosphates). In embodiments, the linker consists of alkyl phosphates (e.g., propyl phosphates) bonded to the reminder of the compound by phosphates at both ends. In embodiments, the linker consists of 1-6 alkyl phosphates (e.g., propyl phosphates) bonded to the reminder of the compound by phosphates on both ends. In embodiments, the linker consists of 4-6 alkyl phosphates (e.g., propyl phosphates) bonded to the remainder of the compound by phosphates on both ends. In embodiments, the linker consists of 5 alkyl phosphates (e.g., propyl phosphates) bonded to the remainder of the compound by phosphates on both ends. A person having ordinary skill in the art will recognize that a linker consisting of alkyl phosphates that is bonded to the remainder of the compound by phosphates on both ends will have one more phosphate than alkylene groups (e.g., a linker consisting of 4 alkyl phosphates that is bonded to the reminder of the compound by phosphates at both ends will have five phosphates and four alkyl groups with alternating phosphate groups and alkyl groups).

In embodiments, the linker includes a first single nucleic acid strand connected to the TLR9-binding nucleic acid substituent and a second single nucleic acid strand connected to the STAT-binding nucleic acid substituent (e.g. STAT1-, STAT2-, STAT3-, STAT4-, STAT5A-, STAT5B-, or STAT6-binding nucleic acid substituent), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In embodiments, the linker includes a first single nucleic acid strand connected to the TLR-binding nucleic acid (e.g. endosomal TLR-, TLR3-, TLR7-, TLR8-, or TLR9-binding nucleic acid) substituent and a second single nucleic acid strand connected to the STAT-binding nucleic acid substituent (e.g. STAT1-, STAT2-, STAT3-, STAT4-, STAT5A-, STAT5B-, or STAT6-binding nucleic acid substituent), wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In embodiments, the linker includes a first single nucleic acid strand connected to the TLR9-binding nucleic acid substituent and a second single nucleic acid strand connected to the STAT3-binding nucleic acid substituent, wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang". In embodiments, the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary nucleic acid sequence in the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the first and second single nucleic acid strands in the hybridized nucleic acid overhang are complementary throughout their entire lengths. In embodiments, the linker is an unsubstituted $C_1$-$C_{20}$ alkylene. In embodiments, the linker is an unsubstituted linear $C_1$-$C_{20}$ alkylene. In embodiments, the linker is an unsubstituted $C_3$-$C_{21}$ alkylene. In embodiments, the linker is an unsubstituted $C_3$-$C_{18}$ alkylene. In embodiments, the linker is an unsubstituted linear $C_3$-$C_{15}$ alkylene. In embodiments, the linker is an unsubstituted linear $C_6$-$C_{21}$ alkylene. In embodiments, the linker is an unsubstituted linear $C_9$-$C_{21}$ alkylene. In embodiments, the linker is an unsubstituted linear $C_9$-$C_{18}$ alkylene. In embodiments, the linker is an unsubstituted linear $C_9$-$C_{15}$ alkylene. In embodiments, the linker is an unsubstituted linear $C_{12}$-$C_{15}$ alkylene. In embodiments, the linker is an unsubstituted linear $C_{12}$ alkylene. In embodiments, the linker is an unsubstituted linear $C_{13}$ alkylene. In embodiments, the linker is an unsubstituted linear $C_{14}$ alkylene. In embodiments, the linker is an unsubstituted linear $C_{15}$ alkylene. In embodiments, the linker is a substituted 2 to 40 membered heteroalkylene. In embodiments, the linker is a substituted 10 to 50 membered heteroalkylene. In embodiments, the linker is a substituted 20 to 40 membered heteroalkylene. In embodiments, the linker is a substituted 25 to 40 membered heteroalkylene. In embodiments, the linker is a substituted 30 to 40 membered heteroalkylene. In embodiments, the linker is a substituted liner 2 to 40 membered heteroalkylene. In embodiments, the linker is a substituted liner 10 to 50 membered heteroalkylene. In embodiments, the linker is a substituted liner 20 to 40 membered heteroalkylene. In embodiments, the linker is a substituted liner 25 to 40 membered heteroalkylene. In embodiments, the linker is a substituted liner 30 to 40 membered heteroalkylene.

In embodiments, the linker includes a first single DNA strand connected to the TLR9-binding DNA substituent and a second single DNA strand connected to the STAT-binding DNA substituent (e.g. STAT1-, STAT2-, STAT3-, STAT4-, STAT5A-, STAT5B-, or STAT6-binding DNA substituent), wherein the first DNA strand includes a DNA sequence that is complementary to a DNA sequence included in the second single DNA strand (both single DNA strands including their respective complementary sequences being collectively a "hybridized DNA overhang". In embodiments, the linker includes a first single DNA strand connected to the TLR-binding nucleic acid (e.g. endosomal TLR-, TLR3-, TLR7-, TLR8-, or TLR9-binding nucleic acid) substituent and a second single DNA strand connected to the STAT-binding DNA substituent (e.g. STAT1-, STAT2-, STAT3-, STAT4-, STAT5A-, STAT5B-, or STAT6-binding DNA substituent), wherein the first DNA strand includes a DNA sequence that is complementary to a DNA sequence included in the second single DNA strand (both single DNA strands including their respective complementary sequences being collectively a "hybridized DNA overhang". In embodiments, the linker includes a first single DNA strand connected to the TLR9-binding DNA substituent and a second single DNA strand connected to the STAT3-binding DNA substituent, wherein the first DNA strand includes a DNA sequence that is complementary to a DNA sequence included in the second single DNA strand (both single DNA strands including their respective complementary sequences being collectively a "hybridized DNA overhang". In embodiments, the hybridized DNA overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary DNA sequence in the hybridized DNA sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the first and second single DNA strands in the hybridized DNA overhang are complementary throughout their entire lengths.

In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, the compound includes a plurality of phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR9-binding DNA substituent. In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR-binding nucleic acid (e.g. endosomal TLR-, TLR3-, TLR7-, TLR8-, or TLR9-binding nucleic acid) substituent. In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT3-binding nucleic acid substituent. In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)). In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT3-binding DNA substituent. In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

In embodiments, the compound includes a phosphorothioate linkage. In embodiments, the compound includes a plurality of phosphorothioate linkages. In embodiments, the compound includes a phosphorothioate linkage in the TLR9-binding DNA substituent. In embodiments, the compound includes a phosphorothioate linkage in the TLR-binding nucleic acid (e.g. endosomal TLR-, TLR3-, TLR7-, TLR8-, or TLR9-binding nucleic acid) substituent. In embodiments, the compound includes a phosphorothioate linkage in the STAT3-binding nucleic acid substituent. In embodiments, the compound includes a phosphorothioate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphorothioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorothioate linkages). In embodiments, the compound includes a phosphorothioate linkage in the STAT3-binding DNA substituent. In embodiments, the compound includes a phosphorothioate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphorothioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorothioate linkages).

In embodiments, the compound includes a phosphoramidate linkage. In embodiments, the compound includes a plurality of phosphoramidate linkages. In embodiments, the compound includes a phosphoramidate linkage in the TLR9-binding DNA substituent. In embodiments, the compound includes a phosphoramidate linkage in the TLR-binding nucleic acid (e.g. endosomal TLR-, TLR3-, TLR7-, TLR8-, or TLR9-binding nucleic acid) substituent. In embodiments, the compound includes a phosphoramidate linkage in the STAT3-binding nucleic acid substituent. In embodiments, the compound includes a phosphoramidate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphoramidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphoramidate linkages). In embodiments, the compound includes a phosphoramidate linkage in the STAT3-binding DNA substituent. In embodiments, the compound includes a phosphoramidate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphoramidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphoramidate linkages).

In embodiments, the compound includes a phosphorodiamidate linkage. In embodiments, the compound includes a plurality of phosphorodiamidate linkages. In embodiments, the compound includes a phosphorodiamidate linkage in the TLR9-binding DNA substituent. In embodiments, the compound includes a phosphorodiamidate linkage in the TLR-binding nucleic acid (e.g. endosomal TLR-, TLR3-, TLR7-, TLR8-, or TLR9-binding nucleic acid) substituent. In embodiments, the compound includes a phosphorodiamidate linkage in the STAT3-binding nucleic acid substituent. In embodiments, the compound includes a phosphorodiamidate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphorodiamidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodiamidate linkages). In embodiments, the compound includes a phosphorodiamidate linkage in the STAT3-binding DNA substituent. In embodiments, the compound includes a phosphorodiamidate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphorodiamidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodiamidate linkages).

In embodiments, the compound includes a phosphorodithioate linkage. In embodiments, the compound includes a plurality of phosphorodithioate linkages. In embodiments, the compound includes a phosphorodithioate linkage in the TLR9-binding DNA substituent. In embodiments, the compound includes a phosphorodithioate linkage in the TLR-binding nucleic acid (e.g. endosomal TLR-, TLR3-, TLR7-, TLR8-, or TLR9-binding nucleic acid) substituent. In embodiments, the compound includes a phosphorodithioate linkage in the STAT3-binding nucleic acid substituent. In embodiments, the compound includes a phosphorodithioate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphorodithioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodithioate linkages). In embodiments, the compound includes a phosphorodithioate linkage in the STAT3-binding DNA substituent. In embodiments, the compound includes a phosphorodithioate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphorodithioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodithioate linkages).

In embodiments, the compound includes a phosphonocarboxylic acid linkage. In embodiments, the compound includes a plurality of phosphonocarboxylic acid linkages. In embodiments, the compound includes a phosphonocarboxylic acid linkage in the TLR9-binding DNA substituent. In embodiments, the compound includes a phosphonocarboxylic acid linkage in the TLR-binding nucleic acid (e.g. endosomal TLR-, TLR3-, TLR7-, TLR8-, or TLR9-binding nucleic acid) substituent. In embodiments, the compound includes a phosphonocarboxylic acid linkage in the STAT3-binding nucleic acid substituent. In embodiments, the compound includes a phosphonocarboxylic acid linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonocarboxylic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylic acid linkages). In embodiments, the compound includes a phosphonocarboxylic acid linkage in the STAT3-binding DNA substituent. In embodiments, the compound includes a phosphonocarboxylic acid linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonocarboxylic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylic acid linkages).

In embodiments, the compound includes a phosphonocarboxylate linkage. In embodiments, the compound includes a plurality of phosphonocarboxylate linkages. In embodiments, the compound includes a phosphonocarboxylate linkage in the TLR9-binding DNA substituent. In embodiments, the compound includes a phosphonocarboxylate linkage in the TLR-binding nucleic acid (e.g. endosomal TLR-, TLR3-, TLR7-, TLR8-, or TLR9-binding nucleic acid) substituent. In embodiments, the compound includes a phosphonocarboxylate linkage in the STAT3-binding nucleic acid substituent. In embodiments, the compound includes a phosphonocarboxylate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonocarboxylate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylate linkages). In embodiments, the compound includes a phosphonocarboxylate linkage in the STAT3-binding DNA substituent. In embodiments, the compound includes a phosphonocarboxylate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonocarboxylate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylate linkages).

In embodiments, the compound includes a phosphonoacetic acid linkage. In embodiments, the compound includes a plurality of phosphonoacetic acid linkages. In embodiments, the compound includes a phosphonoacetic acid linkage in the TLR9-binding DNA substituent. In embodiments, the compound includes a phosphonoacetic acid linkage in the TLR-binding nucleic acid (e.g. endosomal TLR-, TLR3-, TLR7-, TLR8-, or TLR9-binding nucleic acid) substituent. In embodiments, the compound includes a phosphonoacetic acid linkage in the STAT3-binding nucleic acid substituent. In embodiments, the compound includes a phosphonoacetic acid linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonoacetic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoacetic acid linkages). In embodiments, the compound includes a phosphonoacetic acid linkage in the STAT3-binding DNA substituent. In embodiments, the compound includes a phosphonoacetic acid linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonoacetic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoacetic acid linkages).

In embodiments, the compound includes a phosphonoformic acid linkage. In embodiments, the compound includes a plurality of phosphonoformic acid linkages. In embodiments, the compound includes a phosphonoformic acid linkage in the TLR9-binding DNA substituent. In embodiments, the compound includes a phosphonoformic acid linkage in the TLR-binding nucleic acid (e.g. endosomal TLR-, TLR3-, TLR7-, TLR8-, or TLR9-binding nucleic acid) substituent. In embodiments, the compound includes a phosphonoformic acid linkage in the STAT3-binding nucleic acid substituent. In embodiments, the compound includes a phosphonoformic acid linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonoformic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoformic acid linkages). In embodiments, the compound includes a phosphonoformic acid linkage in the STAT3-binding DNA substituent. In embodiments, the compound includes a phosphonoformic acid linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonoformic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoformic acid linkages).

In embodiments, the compound includes a methyl phosphonate linkage. In embodiments, the compound includes a plurality of methyl phosphonate linkages. In embodiments, the compound includes a methyl phosphonate linkage in the TLR9-binding DNA substituent. In embodiments, the compound includes a methyl phosphonate linkage in the TLR-binding nucleic acid (e.g. endosomal TLR-, TLR3-, TLR7-, TLR8-, or TLR9-binding nucleic acid) substituent. In embodiments, the compound includes a methyl phosphonate linkage in the STAT3-binding nucleic acid substituent. In embodiments, the compound includes a methyl phosphonate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a methyl phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are methyl phosphonate linkages). In embodiments, the compound includes a methyl phosphonate linkage in the STAT3-binding DNA substituent. In embodiments, the compound includes a methyl phosphonate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a methyl phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are methyl phosphonate linkages).

In embodiments, the compound includes a boron phosphonate linkage. In embodiments, the compound includes a plurality of boron phosphonate linkages. In embodiments, the compound includes a boron phosphonate linkage in the TLR9-binding DNA substituent. In embodiments, the compound includes a boron phosphonate linkage in the TLR-binding nucleic acid (e.g. endosomal TLR-, TLR3-, TLR7-, TLR8-, or TLR9-binding nucleic acid) substituent. In embodiments, the compound includes a boron phosphonate linkage in the STAT3-binding nucleic acid substituent. In embodiments, the compound includes a boron phosphonate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a boron phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are boron phosphonate linkages). In embodiments, the compound includes a boron phosphonate linkage in the STAT3-binding DNA substituent. In embodiments, the compound includes a boron phosphonate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a boron phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are boron phosphonate linkages).

In embodiments, the compound includes an O-methylphosphoroamidite linkage. In embodiments, the compound includes a plurality of O-methylphosphoroamidite linkages. In embodiments, the compound includes an O-methylphosphoroamidite linkage in the TLR9-binding DNA substituent. In embodiments, the compound includes an O-methylphosphoroamidite linkage in the TLR-binding nucleic acid (e.g. endosomal TLR-, TLR3-, TLR7-, TLR8-, or TLR9-binding nucleic acid) substituent. In embodiments, the compound includes an O-methylphosphoroamidite linkage in the STAT3-binding nucleic acid substituent. In embodiments, the compound includes an O-methylphosphoroamidite linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a O-methylphosphoroamidite linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are O-methylphosphoroamidite linkages). In embodiments, the compound includes an O-methylphosphoroamidite linkage in the STAT3-binding DNA substituent. In embodiments, the compound includes an O-methylphosphoroamidite linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a O-methylphosphoroamidite linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are O-methylphosphoroamidite linkages).

In embodiments, the compound includes a nucleic acid analog (e.g. LNA). In embodiments, the compound includes a plurality of nucleic acid analogs (e.g. LNA). In embodiments, the compound includes a nucleic acid analog (e.g. LNA) in the TLR9-binding DNA substituent. In embodiments, the compound includes a nucleic acid analog (e.g. LNA) in the TLR-binding nucleic acid (e.g. endosomal TLR-, TLR3-, TLR7-, TLR8-, or TLR9-binding nucleic acid) substituent. In embodiments, the compound includes a nucleic acid analog (e.g. LNA) in the STAT3-binding nucleic acid substituent. In embodiments, the compound includes a nucleic acid analog (e.g. LNA) in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acids in the compound is a nucleic acid analog (e.g. LNA) (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all nucleic acids in the compound are nucleic acid analogs (e.g. LNA)). In embodiments, the compound includes a nucleic acid analog (e.g. LNA) in the STAT3-binding DNA substituent. In embodiments, the compound includes a nucleic acid analog (e.g. LNA) in the STAT-binding DNA substituent (e.g. STAT1-, STAT2-, STAT3-, STAT4-, STAT5A-, STAT5B-, or STAT6-binding DNA substituent). In embodiments, one or more of the DNA nucleic acids in the compound is a nucleic acid analog (e.g. LNA) (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all nucleic acids in the compound are nucleic acid analogs (e.g. LNA)).

TABLE 1

| STAT-binding nucleic acid substituent | TLR-binding nucleic acid substituent | | | | | |
|---|---|---|---|---|---|---|
| | TLR | Endosomal TLR | TLR3 | TLR7 | TLR8 | TLR9 |
| STAT | 1 | 2 | 3 | 4 | 5 | 6 |
| STAT1 | 7 | 8 | 9 | 10 | 11 | 12 |
| STAT2 | 13 | 14 | 15 | 16 | 17 | 18 |
| STAT3 | 19 | 20 | 21 | 22 | 23 | 24 |
| STAT4 | 25 | 26 | 27 | 28 | 29 | 30 |
| STAT5A | 31 | 32 | 33 | 34 | 35 | 36 |
| STAT5B | 37 | 38 | 39 | 40 | 41 | 42 |
| STAT6 | 43 | 44 | 45 | 46 | 47 | 48 |

In embodiments, the compound includes a combination of a STAT-binding nucleic acid substituent and TLR-binding nucleic acid substituent, selected from the combinations in Table 1 immediately above. In embodiments the STAT-binding nucleic acid substituent and TLR-binding nucleic acid substituent are as described herein. In embodiments the STAT-binding nucleic acid substituent and TLR-binding nucleic acid substituent are human. In embodiments the STAT-binding nucleic acid substituent is a STAT-binding DNA substituent. In embodiments the TLR-binding nucleic acid substituent is a TLR-binding DNA substituent.

In embodiments, the spacer is a substituted or unsubstituted alkylphosphate spacer having the structure -$L^1$-($PO_4H$-$L^2$)$_{n-}$, wherein $L^1$ and $L^2$ are independently a substituted or unsubstituted alkylene (e.g. substituted or unsubstituted $C_1$-$C_{10}$ alkylene). In embodiments, wherein $L^1$ and $L^2$ are independently a unsubstituted alkylene (e.g. unsubstituted $C_1$-$C_{10}$ alkylene). In embodiments, wherein $L^1$ and $L^2$ are unsubstituted $C_3$ alkylene. In embodiments, $L^1$ and $L^2$ are the same. The symbol n is an integer from 1 to 500. In embodiments, n is an integer from 1 to 400. In embodiments, n is an integer from 1 to 300. In embodiments, n is an integer from 1 to 200. In embodiments, n is an integer from 1 to 100. In embodiments, n is an integer from 1 to 50. In embodiments, n is an integer from 1 to 25. In embodiments, n is an integer from 1 to 10. In embodiments, n is an integer from 1 to 5. In embodiments, n is an integer from 1 to 4. A person having ordinary skill in the art will recognize that the substituted or unsubstituted alkylphosphate spacer may exist in its salt form, e.g. $L^1$-($PO_4^-$-$L^2$)$_{n-}$. The substituted or unsubstituted alkylphosphate spacer may connect the 3' phosphate of a first nucleic acid to a 5' phosphate of a second nucleic acid as described herein. In embodiments, the spacer may be a —($CH_2CH_2CH_2$–$PO_4H$)$_{n-}$, wherein n is an integer between 1 and 20 (e.g., 1, 2, 3, 4, 5, 6, 7, 8, 9, 10, 11, 12, 13, 14, 15, 16, 17, 18, 19, or 20). In embodiments, the spacer may be a —($CH_2CH_2CH_2$—$PO_4H$)$_{n-}$, wherein n is an integer between 1 and 20 (e.g., 1, 2, 3, 4, 5, 6, 7, 8, 9, 10, 11, 12, 13, 14, 15, 16, 17, 18, 19, or 20) wherein the terminal spacer propyl moiety is bonded directly to a 3' phosphate moiety and the terminal spacer phosphate moiety is bonded directly to a 5' carbon of a deoxyribose. In embodiments, the spacer includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the spacer includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

In embodiments, the linker is a substituted or unsubstituted alkylphosphate linker having the structure -$L^{1a}$-($PO_4H$-$L^{2a}$)$_{n1-}$, wherein $L^{1a}$ and $L^{2a}$ are independently a substituted or unsubstituted alkylene (e.g. substituted or unsubstituted $C_1$-$C_{10}$ alkylene). In embodiments, wherein $L^{1a}$ and $L^{2a}$ are independently a unsubstituted alkylene (e.g. unsubstituted $C_1$-$C_{10}$ alkylene). In embodiments, wherein $L^{1a}$ and $L^{2a}$ are unsubstituted $C_3$ alkylene. In embodiments, $L^{1a}$ and $L^{2a}$ are the same. The symbol n1 is an integer from 1 to 500. In embodiments, n1 is an integer from 1 to 400. In embodiments, n1 is an integer from 1 to 300. In embodiments, n1 is an integer from 1 to 200. In embodiments, n1 is an integer from 1 to 100. In embodiments, n1 is an integer from 1 to 50. In embodiments, n1 is an integer from 1 to 25. In embodiments, n1 is an integer from 1 to 10. In embodiments, n1 is an integer from 1 to 5. In embodiments, n1 is an integer from 1 to 4. A person having ordinary skill in the art will recognize that the substituted or unsubstituted alkylphosphate linker may exist in its salt form, e.g. $L^{1a}$-($PO_4^-$-$L^{2a}$)$_{n1-}$. The substituted or unsubstituted alkylphosphate linker may connect the 3' phosphate of a first nucleic acid to a 5' phosphate of a second nucleic acid as described herein. In embodiments, the linker is a —($CH_2CH_2CH_2$—$PO_4H$)$_{n1-}$, wherein n1 is an integer between 1 and 20 (e.g., 1, 2, 3, 4, 5, 6, 7, 8, 9, 10, 11, 12, 13, 14, 15, 16, 17, 18, 19, or 20). In embodiments, the linker is a -($CH_2CH_2CH_2$–$PO_4H$)$_{n1-}$, wherein n1 is an integer between 1 and 20 (e.g., 1, 2, 3, 4, 5, 6, 7, 8, 9, 10, 11, 12, 13, 14, 15, 16, 17, 18, 19, or 20) wherein the terminal linker propyl moiety is bonded directly to a 3' phosphate moiety and the terminal linker phosphate moiety is bonded directly to a 5' carbon of a deoxyribose. In embodiments, the linker includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the linker includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

In embodiments, the terminal moiety is a substituted or unsubstituted alkylphosphate terminal moiety having the structure -$L^{1b}$-($PO_4H$-$L^{2b}$)$_{n2}$-H, wherein $L^{1b}$ and $L^{2b}$ are independently a substituted or unsubstituted alkylene (e.g. substituted or unsubstituted $C_1$-$C_{10}$ alkylene). In embodiments, wherein $L^{1b}$ and $L^{2b}$ are independently a unsubstituted alkylene (e.g. unsubstituted $C_1$-$C_{10}$ alkylene). In embodiments, wherein $L^{1b}$ and $L^{2b}$ are unsubstituted $C_3$ alkylene. In embodiments, $L^{1b}$ and $L^{2b}$ are the same. The symbol n2 is an integer from 1 to 500. In embodiments, n2 is an integer from 1 to 400. In embodiments, n2 is an integer from 1 to 300. In embodiments, n2 is an integer from 1 to 200. In embodiments, n2 is an integer from 1 to 100. In embodiments, n2 is an integer from 1 to 50. In embodiments, n2 is an integer from 1 to 25. In embodiments, n2 is an integer from 1 to 10. In embodiments, n2 is an integer from 1 to 5. In embodiments, n2 is an integer from 1 to 4. A person having ordinary skill in the art will recognize that the substituted or unsubstituted alkylphosphate terminal moiety may exist in its salt form, e.g. $L^{1b}$-($PO_4^-$-$L^{2b}$)$_{n2}$-H. The substituted or unsubstituted alkylphosphate terminal moiety may connect to the 3' phosphate of a nucleic acid as described herein. In embodiments, the terminal moiety is a substituted or unsubstituted alkylphosphate terminal moiety having the structure -$L^{1b}$-($PO_4H$-$L^{2b}$)$_{n2}$-$PO_4H_2$. A person having ordinary skill in the art will recognize that the substituted or unsubstituted alkylphosphate terminal moiety may exist in any of its salt forms, e.g. $L^{1b}$-($PO_4^-$-$L^{2b}$)$_{n2}$-$PO_4H_2$. In embodiments, the terminal moiety is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, the terminal moiety is a substituted or unsubstituted $C_1$-$C_{40}$ alkyl. In embodiments, the terminal moiety is a substituted or unsubstituted 2 to 40 membered heteroalkyl. In embodiments, the terminal moiety is a substituted 2 to 40 membered heteroalkyl. In embodiments, the terminal moiety includes alkyl phosphates (e.g., propyl phosphates). In embodiments, the terminal moiety consists of alkyl phosphates (e.g., propyl phosphates) bonded to the reminder of the compound by phosphates at both ends. In embodiments, the linkER terminal moiety consists of 1-6 alkyl phosphates (e.g., propyl phosphates). In embodiments, the terminal moiety consists of 4-6 alkyl phosphates (e.g., propyl phosphates). In embodiments, the terminal moiety consists of 5 alkyl phosphates (e.g., propyl phosphates). In embodiments, the terminal moiety includes a terminal phosphate. In embodiments, the terminal moiety is a —(CH$_2$CH$_2$CH$_2$—PO$_4$H)$_{n2}$—CH$_2$CH$_2$CH$_2$CH$_2$CH$_2$CH$_2$NH$_2$, wherein n2 is an integer between 1 and 20 (e.g., 1, 2, 3, 4, 5, 6, 7, 8, 9, 10, 11, 12, 13, 14, 15, 16, 17, 18, 19, or 20). In embodiments, the terminal moiety is a —(CH$_2$CH$_2$CH$_2$—PO$_4$H)$_{n2}$—CH$_2$CH$_2$CH$_2$CH$_2$CH$_2$CH$_2$NH$_2$, wherein n2 is an integer between 1 and 20 (e.g., 1, 2, 3, 4, 5, 6, 7, 8, 9, 10, 11, 12, 13, 14, 15, 16, 17, 18, 19, or 20) wherein the terminal moiety propyl moiety at the terminus is bonded directly to a 3' phosphate moiety. In embodiments, the terminal moiety includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the terminal moiety includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

An example of a linker or spacer is shown below.

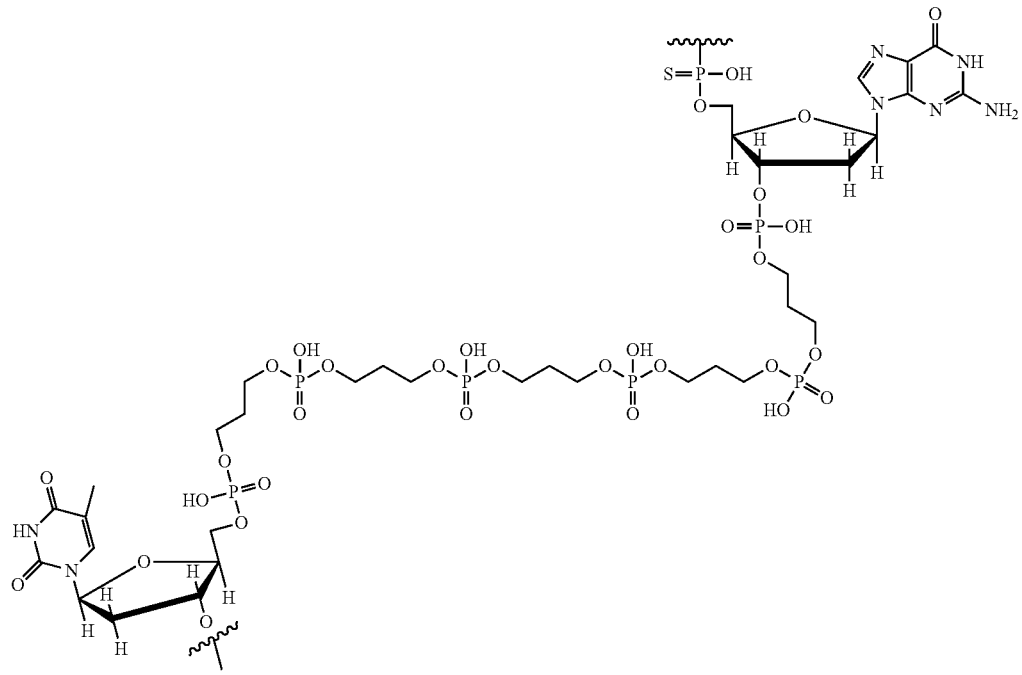

In embodiments, the compound is
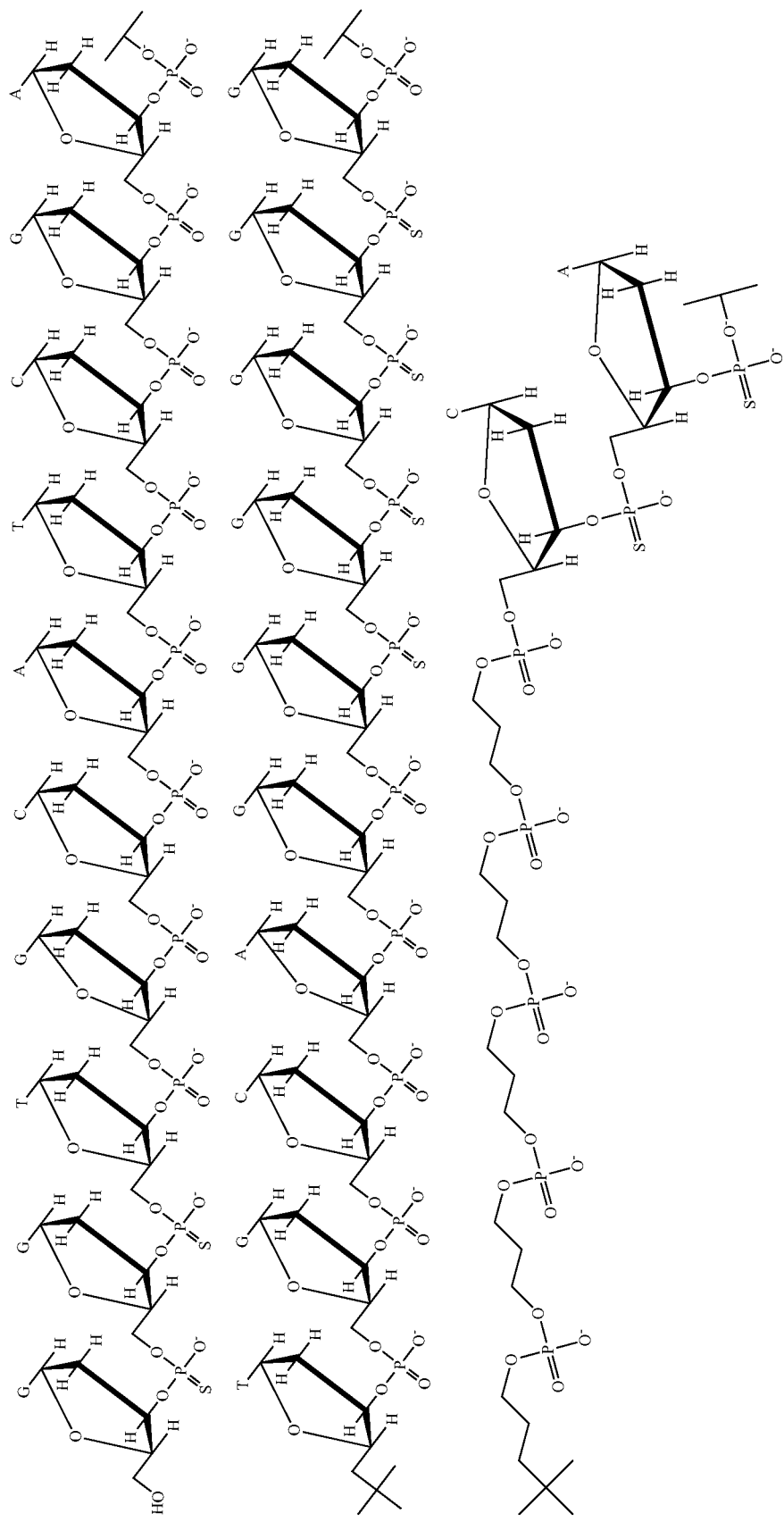

-continued
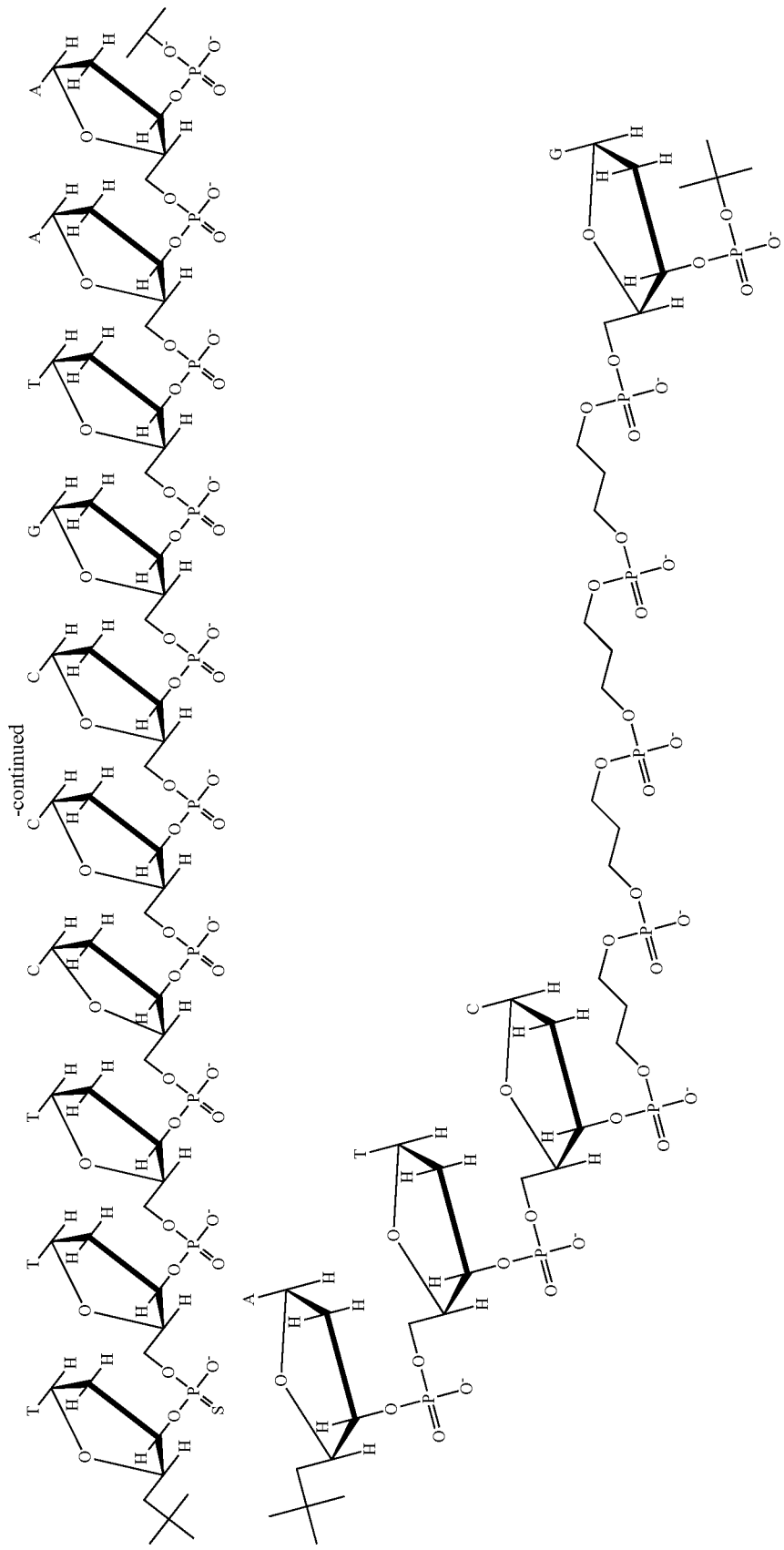

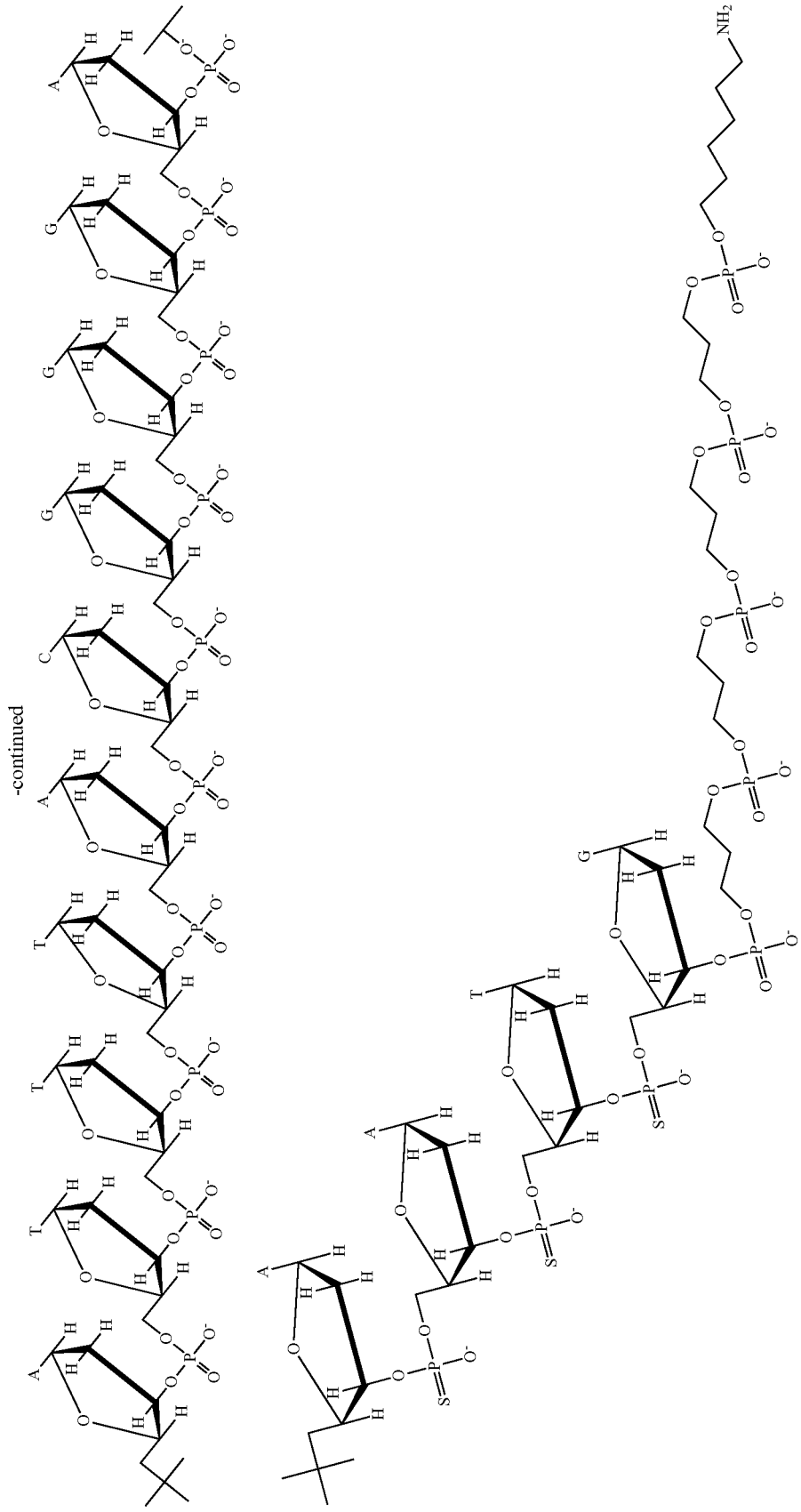

(5'     G*G*TGCATCGATGCAGG*G*G*G*G-xxxxx-C*A*T*TTCCCGTAAATC-xxxx-GATTTACGGGAA*A*T*G-xxxxx 3' (SEQ ID NO:6), * is a phosphothioate linking group, x is an alkyl phosphate, except for 3' terminal x, which is an alkyl-amino following the final phosphate group). In embodiments, the phosphodiester linkage of the compound is replaced with a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, a plurality of phosphodiester linkage of the compound are replaced with, phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In embodiments, a phosphorothioate linkage of the compound is replaced with a phosphodiester linkage or a different phosphodiester derivative linkage. In embodiments, a plurality of phosphorothioate linkages of the compound are replaced with phosphodiester linkages or different phosphodiester derivative linkages. In embodiments, a nucleobase (i.e., cytosine, guanine, adenine, or thymine) of the compound is replaced with a different nucleobase (i.e., cytosine, guanine, adenine, or thymine). In embodiments, a plurality of nucleobases (i.e., cytosine, guanine, adenine, or thymine) of the compound are replaced with different nucleobases (i.e., cytosine, guanine, adenine, or thymine). In embodiments, the compound is covalently bound to a detectable moiety or therapeutic moiety at the 3' end of the terminal moiety. In embodiments, a propylene is replaced with a nucleoside (C, G, A, or T bound to deoxy ribose).

In embodiments, $R^1$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl.

$R^4$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^5$-substituted or unsubstituted alkyl, $R^5$-substituted or unsubstituted heteroalkyl, $R^5$-substituted or unsubstituted cycloalkyl, $R^5$-substituted or unsubstituted heterocycloalkyl, $R^5$-substituted or unsubstituted aryl, or $R^5$-substituted or unsubstituted heteroaryl.

$R^5$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl.

In embodiments, a spacer is a bond, nucleic acid sequence, DNA sequence, nucleic acid analog sequence, $R^2$-substituted or unsubstituted alkylene, $R^2$-substituted or unsubstituted heteroalkylene, $R^2$-substituted or unsubstituted cycloalkylene, $R^2$-substituted or unsubstituted heterocycloalkylene, $R^2$-substituted or unsubstituted arylene, or $R^2$-substituted or unsubstituted heteroarylene.

In embodiments, $R^2$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl.

$R^7$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl.

$R^7$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl.

In embodiments, a linker is a bond, nucleic acid sequence, DNA sequence, nucleic acid analog sequence, $R^3$-substituted or unsubstituted alkylene, $R^3$-substituted or unsubstituted heteroalkylene, $R^3$-substituted or unsubstituted cycloalkylene, $R^3$-substituted or unsubstituted heterocycloalkylene, $R^3$-substituted or unsubstituted arylene, or $R^3$-substituted or unsubstituted heteroarylene.

In embodiments, $R^3$ is independently, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl.

$R^{10}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

$R^{11}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl, or R$^{12}$-substituted or unsubstituted heteroaryl.

R$^6$, R$^9$, and R$^{12}$ are independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, a compound as described herein may include multiple instances of R$^1$, R$^2$, R$^3$, R$^4$, R$^5$, R$^6$, R$^7$, R$^8$, R$^9$, R$^{10}$, R$^{12}$, and/or other variables. In such embodiments, each variable may optional be different and be appropriately labeled to distinguish each group for greater clarity. For example, where each R$^1$, R$^2$, R$^3$, R$^4$, R$^5$, R$^6$, R$^7$, R$^8$, R$^9$, R$^{10}$, R$^{11}$ and/or R$^{12}$ is different, they may be referred to, for example, as R$^{1a}$, R$^{1b}$, R$^{1c}$, R$^{1d}$, R$^{1e}$, R$^{1f}$, R$^{1g}$, R$^{1h}$, R$^{1i}$, R$^{1j}$, R$^{1k}$, R$^{1l}$, R$^{1m}$, R$^{1n}$, R$^{1o}$, R$^{1p}$, R$^{1q}$, R$^{1r}$, R$^{1s}$, R$^{1t}$, R$^{1u}$, R$^{1v}$, R$^{1w}$, R$^{2a}$, R$^{2b}$, R$^{2c}$, R$^{2d}$, R$^{2e}$, R$^{2f}$, R$^{2g}$, R$^{2h}$, R$^{2i}$, R$^{2j}$, R$^{2k}$, R$^{2l}$, R$^{2m}$, R$^{2n}$, R$^{2o}$, R$^{2p}$, R$^{2q}$, R$^{2r}$, R$^{2s}$, R$^{2t}$, R$^{2u}$, R$^{2v}$, R$^{2w}$, R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{3k}$, R$^{3l}$, R$^{3m}$, R$^{3n}$, R$^{3o}$, R$^{3p}$, R$^{3q}$, R$^{3r}$, R$^{3s}$, R$^{3t}$, R$^{3u}$, R$^{3v}$, R$^{3w}$, R$^{4a}$, R$^{4b}$, R$^{4c}$, R$^{4d}$, R$^{4e}$, R$^{4f}$, R$^{4g}$, R$^{4h}$, R$^{4i}$, R$^{4j}$, R$^{4k}$, R$^{4l}$, R$^{4m}$, R$^{4n}$, R$^{4o}$, R$^{4p}$, R$^{4q}$, R$^{4r}$, R$^{4s}$, R$^{4t}$, R$^{4u}$, R$^{4v}$, R$^{4w}$, R$^{5a}$, R$^{5b}$, R$^{5c}$, R$^{5d}$, R$^{5e}$, R$^{5f}$, R$^{5g}$, R$^{5h}$, R$^{5i}$, R$^{5j}$, R$^{5k}$, R$^{5l}$, R$^{5m}$, R$^{5n}$, R$^{5o}$, R$^{5p}$, R$^{5q}$, R$^{5r}$, R$^{5s}$, R$^{5t}$, R$^{5u}$, R$^{5v}$, R$^{5w}$, R$^{6a}$, R$^{6b}$, R$^{6c}$, R$^{6d}$, R$^{6e}$, R$^{6f}$, R$^{6g}$, R$^{6h}$, R$^{6i}$, R$^{6j}$, R$^{6k}$, R$^{6l}$, R$^{6m}$, R$^{6n}$, R$^{6o}$, R$^{6p}$, R$^{6q}$, R$^{6r}$, R$^{6s}$, R$^{6t}$, R$^{6u}$, R$^{6v}$, R$^{6w}$, R$^{7a}$, R$^{7b}$, R$^{7c}$, R$^{7d}$, R$^{7e}$, R$^{7f}$, R$^{7g}$, R$^{7h}$, R$^{7i}$, R$^{7j}$, R$^{7k}$, R$^{7l}$, R$^{7m}$, R$^{7n}$, R$^{7o}$, R$^{7p}$, R$^{7q}$, R$^{7r}$, R$^{7s}$, R$^{7t}$, R$^{7u}$, R$^{7v}$, R$^{7w}$, R$^{8a}$, R$^{8b}$, R$^{8c}$, R$^{8d}$, R$^{8e}$, R$^{8f}$, R$^{8g}$, R$^{8h}$, R$^{8i}$, R$^{8j}$, R$^{8k}$, R$^{8l}$, R$^{8m}$, R$^{8n}$, R$^{8o}$, R$^{8p}$, R$^{8q}$, R$^{8r}$, R$^{8s}$, R$^{8t}$, R$^{8u}$, R$^{8v}$, R$^{8w}$, R$^{9a}$, R$^{9b}$, R$^{9c}$, R$^{9d}$, R$^{9e}$, R$^{9f}$, R$^{9g}$, R$^{9h}$, R$^{9i}$, R$^{9j}$, R$^{9k}$, R$^{9l}$, R$^{9m}$, R$^{9n}$, R$^{9o}$, R$^{9p}$, R$^{9q}$, R$^{9r}$, R$^{9s}$, R$^{9t}$, R$^{9u}$, R$^{9v}$, R$^{9w}$, R$^{10a}$, R$^{10b}$, R$^{10c}$, R$^{10d}$, R$^{10e}$, R$^{10f}$, R$^{10g}$, R$^{10h}$, R$^{10i}$, R$^{10j}$, R$^{10k}$, R$^{10l}$, R$^{10m}$, R$^{10n}$, R$^{10o}$, R$^{10p}$, R$^{10q}$, R$^{10r}$, R$^{10s}$, R$^{10t}$, R$^{10u}$, R$^{10v}$, R$^{10w}$, R$^{11a}$, R$^{11b}$, R$^{11c}$, R$^{11d}$, R$^{11e}$, R$^{11f}$, R$^{11g}$, R$^{11h}$, R$^{11i}$, R$^{11j}$, R$^{11k}$, R$^{11l}$, R$^{11m}$, R$^{11n}$, R$^{11o}$, R$^{11p}$, R$^{11q}$, R$^{11r}$, R$^{11s}$, R$^{11t}$, R$^{11u}$, R$^{11v}$, R$^{11w}$, R$^{12a}$, R$^{12b}$, R$^{12c}$, R$^{12d}$, R$^{12e}$, R$^{12f}$, R$^{12g}$, R$^{12h}$, R$^{12i}$, R$^{12j}$, R$^{12k}$, R$^{12l}$, R$^{12m}$, R$^{12n}$, R$^{12o}$, R$^{12p}$, R$^{12q}$, R$^{12r}$, R$^{12s}$, R$^{12t}$, R$^{12u}$, R$^{12v}$, or R$^{12w}$, respectively, wherein the definition of R$^1$ is assumed by R$^{1a}$, R$^{1b}$, R$^{1c}$, R$^{1d}$, R$^{1e}$, R$^{1f}$, R$^{1g}$, R$^{1h}$, R$^{1i}$, R$^{1j}$, R$^{1k}$, R$^{1l}$, R$^{1m}$, R$^{1n}$, R$^{1o}$, R$^{1p}$, R$^{1q}$, R$^{1r}$, R$^{1s}$, R$^{1t}$, R$^{1u}$, R$^{1v}$, R$^{1w}$, the definition of R$^2$ is assumed by R$^{2a}$, R$^{2b}$, R$^{2c}$, R$^{2d}$, R$^{2e}$, R$^{2f}$, R$^{2g}$, R$^{2h}$, R$^{2i}$, R$^{2j}$, R$^{2k}$, R$^{2l}$, R$^{2m}$, R$^{2n}$, R$^{2o}$, R$^{2p}$, R$^{2q}$, R$^{2r}$, R$^{2s}$, R$^{2t}$, R$^{2u}$, R$^{2v}$, or R$^{2w}$, the definition of R$^3$ is assumed by R$^{3a}$, R$^{3b}$, R$^{3c}$, R$^{3d}$, R$^{3e}$, R$^{3f}$, R$^{3g}$, R$^{3h}$, R$^{3i}$, R$^{3k}$, R$^{3l}$, R$^{3m}$, R$^{3n}$, R$^{3o}$, R$^{3p}$, R$^{3q}$, R$^{3r}$, R$^{3s}$, R$^{3t}$, R$^{3u}$, R$^{3v}$, R$^{3w}$, the definition of R$^4$ is assumed by R$^{4a}$, R$^{4b}$, R$^{4c}$, R$^{4d}$, R$^{4e}$, R$^{4f}$, R$^{4g}$, R$^{4h}$, R$^{4i}$, R$^{4j}$, R$^{4k}$, R$^{4l}$, R$^{4m}$, R$^{4n}$, R$^{4o}$, R$^{4p}$, R$^{4q}$, R$^{4r}$, R$^{4s}$, R$^{4t}$, R$^{4u}$, R$^{4v}$, R$^{4w}$, the definition of R$^5$ is assumed by R$^{5a}$, R$^{5b}$, R$^{5c}$, R$^{5d}$, R$^{5e}$, R$^{5f}$, R$^{5g}$, R$^{5h}$, R$^{5i}$, R$^{5j}$, R$^{5k}$, R$^{5l}$, R$^{5m}$, R$^{5n}$, R$^{5o}$, R$^{5p}$, R$^{5q}$, R$^{5r}$, R$^{5s}$, R$^{5t}$, R$^{5u}$, R$^{5v}$, R$^{5w}$, the definition of R$^6$ is assumed by R$^{6a}$, R$^{6b}$, R$^{6c}$, R$^{6d}$, R$^{6e}$, R$^{6f}$, R$^{6g}$, R$^{6h}$, R$^{6i}$, R$^{6j}$, R$^{6k}$, R$^{6l}$, R$^{6m}$, R$^{6n}$, R$^{6o}$, R$^{6p}$, R$^{6q}$, R$^{6r}$, R$^{6s}$, R$^{6t}$, R$^{6u}$, R$^{6v}$, R$^{6w}$, the definition of R$^7$ is assumed by R$^{7a}$, R$^{7b}$, R$^{7c}$, R$^{7d}$, R$^{7e}$, R$^{7f}$, R$^{7g}$, R$^{7h}$, R$^{7i}$, R$^{7k}$, R$^{7l}$, R$^{7m}$, R$^{7n}$, R$^{7o}$, R$^{7p}$, R$^{7q}$, R$^{7r}$, R$^{7s}$, R$^{7t}$, R$^{7u}$, R$^{7v}$, R$^{7w}$, the definition of R$^8$ is assumed by R$^{8a}$, R$^{8b}$, R$^{8c}$, R$^{8d}$, R$^{8e}$, R$^{8f}$, R$^{8g}$, R$^{8h}$, R$^{8i}$, R$^{8j}$, R$^{8k}$, R$^{8l}$, R$^{8m}$, R$^{8n}$, R$^{8o}$, R$^{8p}$, R$^{8q}$, R$^{8r}$, R$^{8s}$, R$^{8t}$, R$^{8u}$, R$^{8v}$, R$^{8w}$, the definition of R$^9$ is assumed by R$^{9a}$, R$^{9b}$, R$^{9c}$, R$^{9d}$, R$^{9e}$, R$^{9f}$, R$^{9g}$, R$^{9h}$, R$^{9i}$, R$^{9j}$, R$^{9k}$, R$^{9l}$, R$^{9m}$, R$^{9n}$, R$^{9o}$, R$^{9p}$, R$^{9q}$, R$^{9r}$, R$^{9s}$, R$^{9t}$, R$^{9u}$, R$^{9v}$, R$^{9w}$, the definition of R$^{10}$ is assumed by R$^{10a}$, R$^{10b}$, R$^{10c}$, R$^{10d}$, R$^{10e}$, R$^{10f}$, R$^{10g}$, R$^{10h}$, R$^{10i}$, R$^{10j}$, R$^{10k}$, R$^{10l}$, R$^{10m}$, R$^{10n}$, R$^{10o}$, R$^{10p}$, R$^{10q}$, R$^{10r}$, R$^{10s}$, R$^{10t}$, R$^{10u}$, R$^{10v}$, R$^{10w}$, the definition of R$^{11}$ is assumed by R$^{11a}$, R$^{11b}$, R$^{11c}$, R$^{11d}$, R$^{11e}$, R$^{11f}$, R$^{11g}$, R$^{11h}$, R$^{11i}$, R$^{11j}$, R$^{11k}$, R$^{11l}$, R$^{11m}$, R$^{11n}$, R$^{11o}$, R$^{11p}$, R$^{11q}$, R$^{11r}$, R$^{11s}$, R$^{11t}$, R$^{11u}$, R$^{11v}$, R$^{11w}$, the definition of R$^{12}$ is assumed by R$^{12a}$, R$^{12b}$, R$^{12c}$, R$^{12d}$, R$^{12e}$, R$^{12f}$, R$^{12g}$, R$^{12h}$, R$^{12i}$, R$^{12j}$, R$^{12k}$, R$^{12l}$, R$^{12m}$, R$^{12n}$, R$^{12o}$, R$^{12p}$, R$^{12q}$, R$^{12r}$, R$^{12s}$, R$^{12t}$, R$^{12u}$, R$^{12v}$, and/or R$^{12w}$.

The variables used within a definition of R$^1$, R$^2$, R$^3$, R$^4$, R$^5$, R$^6$, R$^7$, R$^8$, R$^9$, R$^{10}$, R$^{11}$, R$^{12}$, and/or other variables that appear at multiple instances and are different may similarly be appropriately labeled to distinguish each group for greater clarity. In embodiments, the TLR-binding nucleic acid substituent is a TLR-binding nucleic acid substituent described herein, including in an aspect, embodiment, example, table, figure, or claim. In embodiments, the TLR-binding DNA substituent is a TLR-binding DNA substituent described herein, including in an aspect, embodiment, example, table, figure, or claim. In embodiments, the STAT-binding nucleic acid substituent is a STAT-binding nucleic acid substituent described herein, including in an aspect, embodiment, example, table, figure, or claim. In embodiments, the STAT3-binding nucleic acid substituent is a STAT3-binding nucleic acid substituent described herein, including in an aspect, embodiment, example, table, figure, or claim. In embodiments, the STAT-binding DNA substituent is a STAT-binding DNA substituent described herein, including in an aspect, embodiment, example, table, figure, or claim. In embodiments, the STAT3-binding DNA substituent is a STAT3-binding DNA substituent described herein, including in an aspect, embodiment, example, table, figure, or claim. In embodiments, the Linker is a Linker described herein, including in an aspect, embodiment, example, table, figure, or claim. In embodiments, the Spacer is a Spacer described herein, including in an aspect, embodiment, example, table, figure, or claim. In embodiments, the Terminal moiety is a Terminal moiety described herein, including in an aspect, embodiment, example, table, figure, or claim. In embodiments, the compound is a compound described herein, including in an aspect, embodiment, example, table, figure, or claim.

Pharmaceutical Compositions

In an aspect is provided a pharmaceutical composition including a pharmaceutically acceptable excipient and a compound, or pharmaceutically acceptable salt thereof, described herein (including in an aspect, embodiment, table, figure, claim, sequence listing, or example). In embodiments of the pharmaceutical compositions, the compound, or pharmaceutically acceptable salt thereof, as described herein (including in an aspect, embodiment, table, figure, claim, sequence listing, or example), is included in a therapeutically effective amount.

In embodiments, the pharmaceutical composition further includes a second agent (e.g. therapeutic agent). In embodiments, the second agent is an anti-cancer agent. In embodiments, the second agent is an anti-viral agent. In embodiments of the pharmaceutical compositions, the pharmaceutical composition includes a second agent (e.g. therapeutic agent) in a therapeutically effective amount. In embodiments, the pharmaceutical composition is a vaccine formulation including a compound described herein, a vaccine excipient, and an antigenic component. In embodiments, the antigenic component is a cancer antigenic component. In embodiments, the antigenic component is a tumor-associated antigen. In embodiments, the pharmaceutical composition is a vaccine including a compound described herein, a vaccine excipient, and an antigenic component.

Methods

In an aspect is provided a method of treating cancer in a patient in need of the treatment, the method including administering a compound, or pharmaceutically acceptable salt thereof, described herein (including in an aspect, embodiment, table, figure, claim, sequence listing, or example).

In an aspect is provided a method of treating a viral disease (e.g. herpesvirus infection associated disease or hepatitis virus infection associated disease or HIV infection associated disease) associated with STAT3-dependent immunosuppression in a patient in need of the treatment, the method including administering a compound, or pharmaceutically acceptable salt thereof, described herein (including in an aspect, embodiment, table, figure, claim, sequence listing, or example).

In an aspect is provided a compound as described herein for use in the manufacture of a medicament for treatment of a disease (e.g., cancer, infectious disease, virus associated disease). The use includes administering to the subject a compound described herein. The use may include administering to the subject a therapeutically effective amount of a compound described herein.

In an aspect is provided a compound as described herein for use in the treatment of a cancer in a subject in need of such treatment. The use includes administering to the subject a compound described herein. The use may include administering to the subject a therapeutically effective amount of a compound described herein.

In an aspect is provided a compound as described herein for use in the treatment of a viral disease associated with STAT3-dependent immunosuppression in a subject in need of such treatment. The use includes administering to the subject a compound described herein. The use may include administering to the subject a therapeutically effective amount of a compound described herein.

In embodiments, the method or use includes administering a therapeutically effective amount of a compound described herein (including in an aspect, embodiment, table, figure, claim, sequence listing, or example).

In embodiments, the method or use includes systemic administration of the compound. In embodiments, the method or use includes parenteral administration of the compound. In embodiments, the method or use includes intravenous administration of the compound. In embodiments, the method or use includes administration directly to a tumor. In embodiments, the method or use includes local administration to the site of infection or cancer.

In embodiments, the cancer is a hematopoietic cell cancer. In embodiments, the cancer is not a hematopoietic cell cancer. In embodiments, the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma. In embodiments, the cancer is prostate cancer (e.g. castration-resistant). In embodiments, the cancer is breast cancer (e.g. triple negative). In embodiments, the cancer is glioblastoma. In embodiments, the cancer is ovarian cancer. In embodiments, the cancer is lung cancer. In embodiments, the cancer is head and neck cancer. In embodiments, the cancer is esophageal cancer. In embodiments, the cancer is skin cancer. In embodiments, the cancer is melanoma. In embodiments, the cancer is brain cancer. In embodiments, the cancer is colorectal cancer. In embodiments, the cancer is leukemia (e.g. AML, ALL, or CML). In embodiments, the cancer is lymphoma. In embodiments, the cancer is myeloma (e.g. multiple myeloma). In embodiments, the cancer is squamous cell carcinoma (e.g. head and neck cancer or esophageal cancer). In embodiments, the cancer is metastatic cancer. In embodiments, the cancer is acute myeloid leukemia. In embodiments, the cancer is B cell lymphoma. In embodiments, the cancer is multiple myeloma. In embodiments, the cancer is prostate cancer. In embodiments, the cancer is glioblastoma. In embodiments, the cancer has an increased level of STAT3 (e.g. activity, mRNA, or protein) relative to a control (e.g. non-cancerous cell of the same type as the cancer cell). In embodiments, the cancer has an increased level of TLR9 relative to a control (e.g. non-cancerous cell of the same type as the cancer cell). In embodiments, the cancer has an increased level of TLR (e.g. endosomal TLR, TLR3, TLR7, TLR8, or TLR9) relative to a control (e.g. non-cancerous cell of the same type as the cancer cell). In embodiments, the cancer has an increased level of phosphorylated STAT3 relative to a control (e.g. non-cancerous cell of the same type as the cancer cell). In embodiments, the cancer has an increased level of a STAT transcription factor (e.g. STAT1, STAT2, STAT3, STAT4, STAT5A, STAT5B, or STAT6) (e.g. activity, mRNA, or protein) relative to a control (e.g. non-cancerous cell of the same type as the cancer cell). In embodiments, the cancer has an increased level of phosphorylated STAT (e.g. STAT1, STAT2, STAT3, STAT4, STAT5A, STAT5B, or STAT6) relative to a control (e.g. non-cancerous cell of the same type as the cancer cell). In embodiments, the STAT is STAT1. In embodiments, the STAT is STAT2. In embodiments, the STAT is STAT3. In embodiments, the STAT is STAT4. In embodiments, the STAT is STAT5A. In embodiments, the STAT is STAT5B. In embodiments, the STAT is STAT6. In embodiments, the STAT is human.

In embodiments, the viral disease associated with STAT3-dependent immunosuppression is HHV-1 infection. In embodiments, the viral disease associated with STAT3-dependent immunosuppression is HHV-2 infection. In embodiments, the viral disease associated with STAT3-dependent immunosuppression is HHV-3 infection. In embodiments, the viral disease associated with STAT3-dependent immunosuppression is HHV-4 infection. In embodiments, the viral disease associated with STAT3-dependent immunosuppression is HHV-5 infection. In embodiments, the viral disease associated with STAT3-dependent immunosuppression is HHV-6A infection. In embodiments, the viral disease associated with STAT3-dependent immunosuppression is HHV-6B infection. In embodiments, the viral disease associated with STAT3-dependent immunosuppression is HHV-7 infection. In embodiments, the viral disease associated with STAT3-dependent immunosuppression is HHV-8 infection. In embodiments, the viral disease associated with STAT3-dependent immunosuppression is hepatitis A virus infection. In embodiments, the viral disease associated with STAT3-dependent immunosuppression is hepatitis B virus infection. In embodiments, the viral disease associated with STAT3-dependent immunosuppression is hepatitis C virus infection. In embodiments, the viral disease associated with STAT3-dependent immunosuppression is hepatitis D virus infection. In embodiments, the viral disease associated with STAT3-dependent immunosuppression is hepatitis E virus infection. In embodiments, the viral disease associated with STAT3-dependent immunosuppression is HIV infection.

In an aspect is provided a method of inhibiting the growth of a cancer cell including contacting the cancer cell with a compound described herein (including in an aspect, embodiment, table, figure, claim, sequence listing, or example).

In an aspect is provided a compound as described herein for use in inhibiting the growth of a cancer cell. The use includes contacting the cancer cell with a compound described herein. The use may include contacting the cancer cell with an effective amount of a compound described herein.

In an aspect is provided a compound as described herein for use in the manufacture of a medicament for inhibiting the growth of a cancer cell.

In embodiments, the cancer cell includes a level of TLR (e.g. endosomal TLR, TLR3, TLR7, TLR8, or TLR9) greater than a non-cancerous cell control. In embodiments, the cancer cell includes a level of TLR9 greater than a non-cancerous cell control. In embodiments, the cancer cell includes a level of a STAT transcription factor (e.g. STAT1, STAT2, STAT3, STAT4, STAT5A, STAT5B, or STAT6) greater than a non-cancerous cell control. In embodiments, the STAT is STAT1. In embodiments, the STAT is STAT2. In embodiments, the STAT is STAT3. In embodiments, the STAT is STAT4. In embodiments, the STAT is STAT5A. In embodiments, the STAT is STAT5B. In embodiments, the STAT is STAT6. In embodiments, the TLR is an endosomal TLR. In embodiments, the TLR is TLR3. In embodiments, the TLR is TLR7. In embodiments, the TLR is TLR8. In embodiments, the TLR is TLR9. In embodiments, the cancer cell includes a level of STAT3 greater than a non-cancerous cell control. In embodiments, the method or use includes inducing apoptosis of the cancer cell. In embodiments, the method or use includes inducing apoptosis in a cancer cell but not a non-cancer cell. In embodiments, the method or use includes inducing apoptosis in a cancer cell in a patient but not a non-cancer cell in the same patient. In embodiments, the method or use includes inducing apoptosis in a cancer cell but not a non-cancer cell of the same cell type as the cancer cell (e.g. lung cell, breast cell, pancreatic cell, colorectal cell, prostate cell, hematopoietic cell). In embodiments, the cancer cell is in the brain. In embodiments, the cancer cell is in an organ. In embodiments, the cancer cell is in a bone. In embodiments, the cancer cell is in bone marrow.

In an aspect is provided a method of stimulating the immune system of a patient in need thereof including administering an effective amount of a compound, or pharmaceutically acceptable salt thereof, described herein (including in an aspect, embodiment, table, figure, claim, sequence listing, or example).

In an aspect is provided a compound as described herein for use in the manufacture of a medicament for stimulating the immune system of a patient in need thereof.

In an aspect is provided a compound as described herein for use in stimulating the immune system of a patient in need thereof. The use includes administering to the subject a compound described herein. The use may include administering to the subject a therapeutically effective amount of a compound described herein.

In embodiments, the stimulating includes maturation, differentiation, or proliferation of natural killer cells, T cells, monocytes, or macrophages. In embodiments, the stimulating includes an increase in a $T_H1$-type immune response. In embodiments, the stimulating includes increases in $T_H1$-type immune responses. In embodiments, the method or use includes contacting a plasmacytoid dendritic cell, myeloid dendritic cell, myeloid-derived suppressor cell, granulocytic myeloid-derived suppressor cell, macrophage, B cell, activated NK cell, or activated neutrophil. In embodiments, the method or use includes stimulating a plasmacytoid dendritic cell, myeloid dendritic cell, myeloid-derived suppressor cell, granulocytic myeloid-derived suppressor cell, macrophage, B cell, activated NK cell, or activated neutrophil.

In an aspect is provided a method of reducing the activity of STAT3 in a cell including contacting the cell with a compound described herein (including in an aspect, embodiment, table, figure, claim, sequence listing, or example). In embodiments, the activity of STAT3 is transcriptional activity (e.g. transcriptional activation, increasing transcription of a gene, or decreasing the transcription of a gene). In embodiments, the activity of STAT3 is binding to a genomic DNA (e.g. at a STAT3 recognition site or STAT3 binding site).

In an aspect is provided a method of reducing the activity of a STAT transcription factor (e.g. STAT1, STAT2, STAT3, STAT4, STAT5A, STAT5B, or STAT6) in a cell including contacting the cell with a compound described herein (including in an aspect, embodiment, table, figure, claim, sequence listing, or example). In embodiments, the activity of a STAT transcription factor (e.g. STAT1, STAT2, STAT3, STAT4, STAT5A, STAT5B, or STAT6) is transcriptional activity (e.g. transcriptional activation, increasing transcription of a gene, or decreasing the transcription of a gene). In embodiments, the activity of a STAT transcription factor (e.g. STAT1, STAT2, STAT3, STAT4, STAT5A, STAT5B, or STAT6) is binding to a genomic DNA (e.g. at a STAT (e.g. STAT1, STAT2, STAT3, STAT4, STAT5A, STAT5B, or STAT6) recognition site or STAT (e.g. STAT1, STAT2, STAT3, STAT4, STAT5A, STAT5B, or STAT6) binding site). In embodiments, the STAT is STAT1. In embodiments, the STAT is STAT2. In embodiments, the STAT is STAT3. In embodiments, the STAT is STAT4. In embodiments, the STAT is STAT5A. In embodiments, the STAT is STAT5B. In embodiments, the STAT is STAT6. In embodiments, the method or use includes contacting a plasmacytoid dendritic cell, myeloid dendritic cell, myeloid-derived suppressor cell, granulocytic myeloid-derived suppressor cell, macrophage, B cell, activated NK cell, or activated neutrophil. In embodiments, the method or use includes reducing the activity of a STAT transcription factor (e.g. STAT1, STAT2, STAT3, STAT4, STAT5A, STAT5B, or STAT6) in a plasmacytoid dendritic cell, myeloid dendritic cell, myeloid-derived suppressor cell, granulocytic myeloid-derived suppressor cell, macrophage, B cell, activated NK cell, or activated neutrophil.

In an aspect is provided a compound as described herein for use in reducing the activity of a STAT transcription factor (e.g. STAT1, STAT2, STAT3, STAT4, STAT5A, STAT5B, or STAT6) in a cell. The use includes contacting the cell with a compound described herein. The use may include contacting the cell with an effective amount of a compound described herein.

In embodiments, the method or use includes allowing the compound to bind the STAT transcription factor (e.g. STAT1, STAT2, STAT3, STAT4, STAT5A, STAT5B, or STAT6). In embodiments, the method or use includes allowing the compound to bind the phosphorylated STAT transcription factor (e.g. STAT1, STAT2, STAT3, STAT4, STAT5A, STAT5B, or STAT6). In embodiments, the method or use includes allowing the compound to bind the phosphorylated STAT transcription factor (e.g. STAT1, STAT2, STAT3, STAT4, STAT5A, STAT5B, or STAT6) in the cytosol. In embodiments, the method or use includes allowing the compound to bind the phosphorylated STAT transcription factor (e.g. STAT1, STAT2, STAT3, STAT4, STAT5A, STAT5B, or STAT6) and preventing the STAT transcription factor from entering the nucleus. In embodiments, the method or use includes allowing the compound to bind the phosphorylated STAT transcription factor (e.g. STAT1, STAT2, STAT3, STAT4, STAT5A, STAT5B, or STAT6) and preventing the STAT transcription factor from becoming dephosphorylated. In embodiments, the method or use includes allowing the compound to bind the phosphorylated STAT transcription factor (e.g. STAT1, STAT2, STAT3, STAT4, STAT5A, STAT5B, or STAT6) and prevent binding of the STAT transcription factor to genomic DNA. In embodiments, the method or use includes reducing the levels of a STAT transcription factor (e.g. STAT1, STAT2, STAT3, STAT4, STAT5A, STAT5B, or STAT6). In embodiments, the method or use includes reducing the levels of activity of a STAT transcription factor (e.g. STAT1, STAT2, STAT3, STAT4, STAT5A, STAT5B, or STAT6). In embodiments, the method or use includes reducing the levels of transcription of a STAT transcription factor (e.g. STAT1, STAT2, STAT3, STAT4, STAT5A, STAT5B, or STAT6). In embodiments, the method or use includes reducing the levels of translation of a STAT transcription factor (e.g. STAT1, STAT2, STAT3, STAT4, STAT5A, STAT5B, or STAT6). In embodiments, the method or use includes reducing the levels of phosphorylated STAT transcription factor (e.g. STAT1, STAT2, STAT3, STAT4, STAT5A, STAT5B, or STAT6).

In embodiments, the method or use includes contacting a cancer cell with a compound described herein. In embodiments, the method or use includes reducing the level of STAT transcription factor (e.g. STAT1, STAT2, STAT3, STAT4, STAT5A, STAT5B, or STAT6) activity in a disease associated cell. In embodiments, the method or use includes reducing the level of STAT transcription factor (e.g. STAT1, STAT2, STAT3, STAT4, STAT5A, STAT5B, or STAT6) activity in a cancer cell (e.g., leukemia cell, lymphoma cell, myeloma cell, solid tumor cell, acute myeloid leukemia (AML) cell, B cell lymphoma cell, multiple myeloma cell, prostate cancer cell, or glioblastoma cell). In embodiments, the method or use includes reducing the level of STAT transcription factor (e.g. STAT1, STAT2, STAT3, STAT4, STAT5A, STAT5B, or STAT6) activity in a leukemia cell. In embodiments, the method or use includes reducing the level of STAT transcription factor (e.g. STAT1, STAT2, STAT3, STAT4, STAT5A, STAT5B, or STAT6) activity in a cancer stem cell. In embodiments, the method or use includes reducing the level of STAT transcription factor (e.g. STAT1, STAT2, STAT3, STAT4, STAT5A, STAT5B, or STAT6) activity in a stem cell. In embodiments, the method or use includes reducing the level of STAT transcription factor (e.g. STAT1, STAT2, STAT3, STAT4, STAT5A, STAT5B, or STAT6) activity in a solid tumor cell. In embodiments, the method or use includes reducing the level of STAT transcription factor (e.g. STAT1, STAT2, STAT3, STAT4, STAT5A, STAT5B, or STAT6) activity in a prostate cancer cell. In embodiments, the method or use includes reducing the level of STAT transcription factor (e.g. STAT1, STAT2, STAT3, STAT4, STAT5A, STAT5B, or STAT6) activity in a cell. In embodiments, the method or use includes reducing the level of STAT transcription factor (e.g. STAT1, STAT2, STAT3, STAT4, STAT5A, STAT5B, or STAT6) activity in an immune cell. In embodiments, the method or use includes reducing the level of STAT transcription factor (e.g. STAT1, STAT2, STAT3, STAT4, STAT5A, STAT5B, or STAT6) activity in a leukocyte. In embodiments, the method or use includes reducing the level of STAT transcription factor (e.g. STAT1, STAT2, STAT3, STAT4, STAT5A, STAT5B, or STAT6) activity in a lymphocyte. In embodiments, the method or use includes reducing the level of STAT transcription factor (e.g. STAT1, STAT2, STAT3, STAT4, STAT5A, STAT5B, or STAT6) activity in a dendritic cell. In embodiments, the method or use includes reducing the level of STAT transcription factor (e.g. STAT1, STAT2, STAT3, STAT4, STAT5A, STAT5B, or STAT6) activity in a plasmacytoid dendritic cell. In embodiments, the method or use includes reducing the level of STAT transcription factor (e.g. STAT1, STAT2, STAT3, STAT4, STAT5A, STAT5B, or STAT6) activity in a myeloid dendritic cell. In embodiments, the method or use includes reducing the level of STAT transcription factor (e.g. STAT1, STAT2, STAT3, STAT4, STAT5A, STAT5B, or STAT6) activity in a macrophage cell. In embodiments, the method or use includes reducing the level of STAT transcription factor (e.g. STAT1, STAT2, STAT3, STAT4, STAT5A, STAT5B, or STAT6) activity in a suppressor cell. In embodiments, the method or use includes reducing the level of STAT transcription factor (e.g. STAT1, STAT2, STAT3, STAT4, STAT5A, STAT5B, or STAT6) activity in a myeloid-derived suppressor cell (MDSC). In embodiments, the method or use includes reducing the level of STAT transcription factor (e.g. STAT1, STAT2, STAT3, STAT4, STAT5A, STAT5B, or STAT6) activity in a B cell. In embodiments, the method or use includes reducing the level of STAT transcription factor (e.g. STAT1, STAT2, STAT3, STAT4, STAT5A, STAT5B, or STAT6) activity in a T cell. In embodiments, the method or use includes reducing the level of STAT transcription factor (e.g. STAT1, STAT2, STAT3, STAT4, STAT5A, STAT5B, or STAT6) activity in a granulocytic myeloid-derived suppressor cells (gMDSC). In embodiments, the method or use includes reducing the level suppression of the immune system. In embodiments, the method or use includes increasing the level of TLR9 in a disease associated cell. In embodiments, the method or use includes increasing the level of TLR9 activity in a disease associated cell. In embodiments, the method or use includes increasing the level of TLR9 activity in an immune cell. In embodiments, the method or use includes increasing the level of TLR9 activity in a cancer cell (e.g., leukemia cell, lymphoma cell, myeloma cell, solid tumor cell, acute myeloid leukemia (AML) cell, B cell lymphoma cell, multiple myeloma cell, prostate cancer cell, or glioblastoma cell).

In embodiments, the method or use includes increasing the level of CD8+ cells. In embodiments, the method or use includes increasing the level of immune effector cells. In embodiments, the method or use includes increasing the level of T cells. In embodiments, the method or use includes increasing the level of effector T cells. In embodiments, the method or use includes decreasing the level of CD4+ cells. In embodiments, the method or use includes decreasing the level of CD4+/Fox3P+ cells. In embodiments, the method or use includes decreasing the level of regulatory cells. In embodiments, the method or use includes decreasing the level of regulatory T cells. In embodiments, the method or use includes decreasing the level of suppressor cells. In embodiments, the method or use includes decreasing the level of suppressor T cells. In embodiments, the method or use includes decreasing the level of myeloid suppressor cells. In embodiments, the method or use includes decreasing the level of immune system suppression. In embodiments, the method or use includes inducing the immune system to recognize disease associated cells (e.g., cancer cells, infected cells). In embodiments, the method or use includes reducing the level of Arginase-1 in a cell (e.g., disease associated cell, cancer cell, infected cell, immune cell). In embodiments, the method or use includes increasing proliferation of T cells. In embodiments, the method or use includes reducing the level of CD80 in a cell. In embodiments, the method or use includes reducing the level of CD86 in a cell. In embodiments, the method or use includes reducing the level of CD48 in a cell. In embodiments, the method or use includes reducing the level of PDL-1. In embodiments, the method or use includes reducing the level of T regulatory cells. In embodiments, the method or use includes reducing the level of CD25+ cells. In embodiments, the method or use includes reducing the level of CTLA4+ cells. In embodiments, the method or use includes increasing the level of CD28 in a cell. In embodiments, the method or use includes reducing the level of CD15+ cells. In embodiments, the method or use includes reducing the level of CD15 in a cell. In embodiments, the method or use includes reducing the level of CD15+ granulocytes.

In embodiments, the method or use includes systemic administration of the compound. In embodiments, the method or use includes parenteral administration of the compound. In embodiments, the method or use includes intravenous administration of the compound. In embodiments, the method or use includes administration directly to a tumor. In embodiments, the method or use includes local administration to the site of infection or cancer.

Additional Embodiments

1. A compound comprising a TLR-binding nucleic acid substituent conjugated to a STAT-binding DNA substituent.

2. The compound of embodiment 1, wherein the STAT is human STAT1, STAT2, STAT3, STAT4, STAT5A, STAT5B, or STAT6.

3. The compound of embodiment 1, wherein the STAT is human STAT1, STAT2, STAT3, STAT4, STAT5A, STAT5B, or STAT6.

4. The compound of embodiment 1, wherein the STAT is human STAT1.

5. The compound of embodiment 1, wherein the STAT is human STAT2.

6. The compound of embodiment 1, wherein the STAT is human STAT3.

7. The compound of embodiment 1, wherein the STAT is human STAT4.

8. The compound of embodiment 1, wherein the STAT is human STAT5A.

9. The compound of embodiment 1, wherein the STAT is human STAT5B.

10. The compound of embodiment 1, wherein the STAT is human STAT6.

11. The compound of one of embodiments 1 to 10, wherein the TLR is an endosomal TLR.

12. The compound of one of embodiments 1 to 10, wherein the TLR is human TLR3, TLR7, TLR8, or TLR9.

13. The compound of one of embodiments 1 to 10, wherein the TLR is human TLR3.

14. The compound of one of embodiments 1 to 10, wherein the TLR is human TLR7.

15. The compound of one of embodiments 1 to 10, wherein the TLR is human TLR8.

16. The compound of one of embodiments 1 to 10, wherein the TLR is human TLR9.

17. A compound comprising a TLR9-binding DNA substituent conjugated to a STAT3-binding DNA substituent.

18. The compound of embodiment 17, wherein the TLR9-binding DNA substituent comprises a CpG motif.

19. The compound of any one of embodiments 17 to 18, wherein the TLR9-binding DNA substituent comprises an unmethylated CpG motif.

20. The compound of any one of embodiments 17 to 19, wherein the TLR9-binding DNA substituent comprises a DNA sequence capable of forming a G-quadruplex.

21. The compound of any one of embodiments 17 to 20, wherein the TLR9-binding DNA substituent comprises a Class A CpG DNA sequence.

22. The compound of any one of embodiments 17 to 20, wherein the TLR9-binding DNA substituent comprises a Class B CpG DNA sequence.

23. The compound of any one of embodiments 17 to 20, wherein the TLR9-binding DNA substituent comprises a C-type CpG DNA sequence.

24. The compound of one of embodiments 17 to 23, wherein the STAT3-binding DNA substituent comprises a first STAT3-binding DNA sequence covalently bound to a second STAT3-binding DNA sequence by a spacer; and the spacer is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

25. The compound of embodiment 24, wherein the spacer is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

26. The compound of embodiment 24, wherein the spacer is an unsubstituted $C_1$-$C_{40}$ alkylene, unsubstituted 2 to 40 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene.

27. The compound of embodiment 24, wherein the spacer is a substituted 2 to 40 membered heteroalkylene.

28. The compound of embodiment 24, wherein the spacer comprises one or more substituted or unsubstituted alkyl phosphates.

29. The compound of embodiment 24, wherein the spacer is -L1-(PO4H-L2)n-, wherein L1 and L2 are independently a substituted or unsubstituted alkylene (e.g., n-propylene) and L1 is bonded to the first STAT3-binding DNA sequence by a 3' phosphate moiety; n is an integer between 1 and 10 (e.g., 4); and the spacer is bonded to the second first STAT3-binding DNA sequence by a 5' phosphate moiety.

30. The compound of one of embodiments 17 to 29, wherein the STAT3-binding DNA substituent binds phosphorylated STAT3.

31. The compound of one of embodiments 17 to 29, wherein the STAT3-binding DNA substituent binds to a STAT3 dimer.

32. The compound of one of embodiments 17 to 29, wherein the STAT3-binding DNA substituent binds a phosphorylated STAT3 dimer.

33. The compound of one of embodiments 17 to 29, wherein the STAT3-binding DNA substituent preferentially binds phosphorylated STAT3 dimer over unphosphorylated STAT3 monomer.

34. The compound of one of embodiments 17 to 29, wherein the STAT3-binding DNA substituent preferentially binds phosphorylated STAT3 over unphosphorylated STAT3.

35. The compound of one of embodiments 24 to 34, wherein the first STAT3-binding DNA sequence comprises a first nucleic acid sequence and the second STAT3-binding DNA sequence comprises a second nucleic acid sequence, wherein the first and second nucleic acid sequences are complementary.

36. The compound of one of embodiments 24 to 34, wherein the first STAT3-binding DNA sequence and second STAT3-binding DNA sequence form a double-stranded STAT3-binding DNA sequence.

37. The compound of any one of embodiments 17 to 36, wherein the STAT3-binding DNA substituent comprises a STAT3-binding DNA sequence covalently bonded to a terminal moiety; and the terminal moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

38. The compound of embodiment 37, wherein the terminal moiety is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

39. The compound of embodiment 37, wherein the terminal moiety is a substituted C1-C20 alkyl, substituted 2 to 20 membered heteroalkyl, substituted C3-C8 cycloalkyl, substituted 3 to 8 membered heterocycloalkyl, substituted C6-C10 aryl, or substituted 5 to 10 membered heteroaryl.

40. The compound of embodiment 37, wherein the terminal moiety is an unsubstituted C1-C40 alkyl, unsubstituted 2 to 40 membered heteroalkyl, unsubstituted C3-C8 cycloalkyl, unsubstituted 3 to 8 membered heterocycloalkyl, unsubstituted C6-C10 aryl, or unsubstituted 5 to 10 membered heteroaryl.

41. The compound of embodiment 37, wherein the terminal moiety is a substituted 2 to 40 membered heteroalkyl.

42. The compound of embodiment 37, wherein the terminal moiety comprises one or more substituted or unsubstituted alkyl phosphates.

43. The compound of embodiment 37, wherein the terminal moiety is -L1b-(PO4H-L2b)n2-H, wherein L1b and L2b are independently a substituted or unsubstituted alkylene (e.g., n-propylene) and L1b is bonded to the STAT3-binding DNA sequence by a 3' phosphate moiety; n is an integer between 1 and 10 (e.g., 3 or 4); and the terminal moiety is optionally bonded to a terminal phosphate moiety or a terminal phospho-alkyl amino moiety (e.g., PO4H C6-NH2).

44. The compound of embodiment 37, wherein the terminal moiety is an R1 substituted C1-C40 alkyl, R1 substituted 2 to 40 membered heteroalkyl, R1 substituted C3-C8 cycloalkyl, R1 substituted 3 to 8 membered heterocycloalkyl, R1 substituted C6-C10 aryl, or R1 substituted 5 to 10 membered heteroaryl; and R1 is a detectable moiety or a therapeutic moiety.

45. The compound of embodiment 44, wherein the terminal moiety is an R1 substituted 2 to 40 membered heteroalkyl.

46. The compound of one of embodiments 44 to 45, wherein R1 is an oxygen, oxo, amino, or detectable moiety.

47. The compound of embodiment 46, wherein the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety.

48. The compound of one of embodiments 17 to 47, further comprising a linker between the TLR9-binding DNA substituent and the STAT3-binding DNA substituent.

49. The compound of embodiment 48, wherein the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

50. The compound of embodiment 48, wherein the linker is a substituted or unsubstituted C1-C40 alkylene, substituted or unsubstituted 2 to 40 membered heteroalkylene, substituted or unsubstituted C3-C8 cycloalkylene, substituted or unsubstituted 3 to 8 membered heterocycloalkylene, substituted or unsubstituted C6-C10 arylene, or substituted or unsubstituted 5 to 10 membered heteroarylene.

51. The compound of embodiment 48, wherein the linker is an unsubstituted C1-C40 alkylene, unsubstituted 2 to 40 membered heteroalkylene, unsubstituted C3-C8 cycloalkylene, unsubstituted 3 to 8 membered heterocycloalkylene, unsubstituted C6-C10 arylene, or unsubstituted 5 to 10 membered heteroarylene.

52. The compound of embodiment 48, wherein the linker is a substituted 2 to 40 membered heteroalkylene.

53. The compound of embodiment 48 to 52, wherein the linker comprises one or more substituted or unsubstituted alkyl phosphates.

54. The compound of embodiment 48, wherein the linker is -L1a-(PO4H-L2a)n1-, wherein L1a and L2a are independently a substituted or unsubstituted alkylene (e.g., n-propylene) and L1 is bonded to the TLR9-binding DNA substituent by a 3' phosphate moiety; n is an integer between 1 and 10 (e.g., 3 or 4); and the linker is bonded to the STAT3-binding DNA substituent by a 5' phosphate moiety.

55. The compound of any one of embodiments 1 to 54, further comprising a phosphodiester derivative linkage.

56. The compound of any one of embodiments 1 to 54, further comprising a phosphodiester derivative linkage selected from a phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, and O-methylphosphoroamidite linkage.

57. The compound of any one of embodiments 1 to 54, further comprising a plurality of phosphodiester derivative linkages.

58. The compound of any one of embodiments 1 to 54, further comprising a plurality of phosphodiester derivative linkages selected from the group consisting of phosphoramidate linkages, phosphorodiamidate linkages, phosphorothioate linkages, phosphorodithioate linkages, phosphonocarboxylic acid linkages, phosphonocarboxylate linkages, phosphonoacetic acid linkages, phosphonoformic acid linkages, methyl phosphonate linkages, boron phosphonate linkages, and O-methylphosphoroamidite linkages.

59. The compound of any one of embodiments 1 to 58, comprising a phosphodiester derivative linkage in the TLR9-binding DNA substituent.

60. The compound of any one of embodiments 1 to 58, comprising a phosphodiester derivative linkage in the TLR9-binding DNA substituent, wherein the phosphodiester derivative linkage is selected from a phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, and O-methylphosphoroamidite linkage.

61. The compound of any one of embodiments 1 to 60, comprising a phosphodiester derivative linkage in the STAT3-binding DNA substituent.

62. The compound of any one of embodiments 1 to 60, comprising a phosphodiester derivative linkage in the STAT3-binding DNA substituent, wherein the phosphodiester derivative linkage is selected from a phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, and O-methylphosphoroamidite linkage 63. The compound of any one of embodiments 1 to 54, further comprising a phosphorothioate linkage.

64. The compound of any one of embodiments 1 to 54, further comprising a plurality of phosphorothioate linkages.

65. The compound of any one of embodiments 17 to 64, comprising a phosphorothioate linkage in the TLR9-binding DNA substituent.

66. The compound of any one of embodiments 17 to 65, comprising a phosphorothioate linkage in the STAT3-binding DNA substituent.

67. The compound of any one of embodiments 1 to 66, wherein the nucleotide sugars are deoxyribose.

68. A pharmaceutical composition comprising a pharmaceutically acceptable excipient and the compound of one of embodiments 1 to 67.

69. The pharmaceutical composition of embodiment 68, further comprising a second therapeutic agent.

70. The pharmaceutical composition of embodiment 69, wherein the second therapeutic agent is an anti-cancer agent.

71. A method of treating cancer in a patient in need of such treatment, the method comprising administering a therapeutically effective amount of a compound of one of embodiments 1 to 67.

72. The method of embodiment 71, wherein the cancer is a hematopoietic cell cancer.

73. The method of embodiment 71, wherein the cancer is not a hematopoietic cell cancer.

74. The method of embodiment 71, wherein the cancer is leukemia.

75. The method of embodiment 71, wherein the cancer is acute myeloid leukemia.

76. The method of embodiment 71, wherein the cancer is a solid cancer.

77. The method of embodiment 71, wherein the cancer is a carcinoma.

78. The method of embodiment 71, wherein the cancer is prostate cancer.

79. The method of embodiment 71, wherein the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

80. A method of treating an infectious disease in a patient in need of such treatment, the method comprising administering a therapeutically effective amount of a compound of one of embodiments 1 to 67.

81. The method of embodiment 80, wherein the infectious disease is viral disease.

82. The method of embodiment 80, wherein the infectious disease a herpesvirus associated disease.

83. The method of embodiment 80, wherein the infectious disease a herpesvirus associated disease, wherein the herpesvirus is HHV-1, HHV-2, HHV-3, HHV-4, HHV-5, HHV-6A, HHV-6B, HHV-7, or HHV-8.

84. The method of embodiment 80, wherein the infectious disease is an HIV associated disease.

85. The method of embodiment 80, wherein the infectious disease is HIV infection.

86. The method of embodiment 80, wherein the infectious disease is a hepatitis virus associated disease.

87. The method of embodiment 80, wherein the infectious disease is a hepatitis virus associated disease, wherein the hepatitis virus is hepatitis A virus, hepatitis B virus, hepatitis C virus, hepatitis D virus, or hepatitis E virus.

88. A method of inhibiting the growth of a cancer cell comprising contacting the cancer cell with a composition of one of embodiments 1 to 67.

89. The method of embodiment 88, wherein the cancer cell comprises a level of TLR9 greater than a non-cancerous cell control.

90. The method of embodiment 88, wherein the cancer cell comprises a level of STAT3 greater than a non-cancerous cell control.

91. A method of stimulating the immune system of a patient in need thereof comprising administering an effective amount of a composition of one of embodiments 1 to 67 to the patient.

92. The method of embodiment 91, wherein the stimulating comprises maturation, differentiation, or proliferation of natural killer cells, T cells, monocytes, or macrophages.

93. The method of embodiment 91, wherein the stimulating comprises an increase in TH1-type immune responses.

94. The method of embodiment 91, wherein the stimulating comprises an increase in CD8+ cells.

95. The method of embodiment 91, wherein the stimulating comprises a decrease in regulatory cells.

96. The method of embodiment 91, wherein the stimulating comprises a decrease in suppressor cells.

97. The method of embodiment 91, wherein the stimulating comprises a decrease in myeloid suppressor cells.

98. The method of embodiment 91, wherein the stimulating comprises an increase in CD8+ cells.

99. The method of embodiment 91, wherein the stimulating comprises a decrease in CD4+/FoxP3+ cells.

100. A method of stimulating the immune system of a patient in need thereof to recognize disease associated cells, comprising administering an effective amount of a composition of one of embodiments 1 to 67 to the patient.

101. A method of stimulating the immune system of a patient in need thereof to recognize disease associated cells, comprising administering an effective amount of a composition of one of embodiments 1 to 67 to the patient, wherein the disease associated cell is a cancer cell, cancer stem cell, or infected cell.

102. A method of reducing the activity of a STAT transcription factor in a cell comprising contacting the cell with a compound of one of embodiments 1 to 67.

103. The method of embodiment 102, wherein the STAT transcription factor is STAT3.

104. A method of increasing apoptosis of a cell comprising contacting the cell with a compound of one of embodiments 1 to 67.

105. A method of inducing apoptosis of a cell comprising contacting the cell with a compound of one of embodiments 1 to 67.

106. The method of one of embodiments 71 to 105, further comprising contacting a plasmacytoid dendritic cell, myeloid dendritic cell, myeloid-derived suppressor cell, granulocytic myeloid-derived suppressor cell, macrophage, T Cell, B cell, activated NK cell, or activated neutrophil with the compound.

107. The method of one of embodiments 71 to 105, further comprising contacting a plasmacytoid with the compound.

108. The method of one of embodiments 71 to 105, further comprising contacting a dendritic cell with the compound.

109. The method of one of embodiments 71 to 105, further comprising contacting a myeloid dendritic cell with the compound.

110. The method of one of embodiments 71 to 105, further comprising contacting a myeloid-derived suppressor cell with the compound.

111. The method of one of embodiments 71 to 105, further comprising contacting a granulocytic myeloid-derived suppressor cell with the compound.

112. The method of one of embodiments 71 to 105, further comprising contacting a macrophage with the compound.

113. The method of one of embodiments 71 to 105, further comprising contacting a T Cell with the compound.

114. The method of one of embodiments 71 to 105, further comprising contacting a B cell with the compound.

115. The method of one of embodiments 71 to 105, further comprising contacting an activated NK cell with the compound.

116. The method of one of embodiments 71 to 105, further comprising contacting an activated neutrophil with the compound.

117. The method of one of embodiments 71 to 116, further comprising allowing the compound to contact a STAT transcription factor.

118. The method of one of embodiments 71 to 117, further comprising allowing the compound to contact a STAT transcription factor, wherein the STAT transcription factor is STAT1, STAT2, STAT3, STAT4, STAT5A, STAT5B, or STAT6.

119. The method of one of embodiments 71 to 117, further comprising allowing the compound to contact STAT1.

120. The method of one of embodiments 71 to 117, further comprising allowing the compound to contact STAT2.

121. The method of one of embodiments 71 to 117, further comprising allowing the compound to contact STAT3.

122. The method of one of embodiments 71 to 117, further comprising allowing the compound to contact STAT4.

123. The method of one of embodiments 71 to 117, further comprising allowing the compound to contact STAT5A.

124. The method of one of embodiments 71 to 117, further comprising allowing the compound to contact STAT5B.

125. The method of one of embodiments 71 to 117, further comprising allowing the compound to contact STAT6.

126. The method of one of embodiments 71 to 125, further comprising allowing the compound to contact a phosphorylated STAT transcription factor.

127. The method of one of embodiments 71 to 125, further comprising allowing the compound to contact a phosphorylated STAT3 transcription factor.

128. The method of one of embodiments 71 to 125, further comprising allowing the compound to contact a phosphorylated STAT transcription factor in the cytosol of a cell.

129. The method of one of embodiments 71 to 125, further comprising allowing the compound to contact a phosphorylated STAT3 transcription factor in the cytosol of a cell.

130. The method of one of embodiments 71 to 125, further comprising allowing the compound to contact a phosphorylated STAT transcription factor and preventing the STAT transcription factor from entering the nucleus.

131. The method of one of embodiments 71 to 125, further comprising allowing the compound to contact a phosphorylated STAT3 transcription factor and preventing the STAT3 transcription factor from entering the nucleus.

132. The method of one of embodiments 71 to 125, further comprising allowing the compound to contact a phosphorylated STAT transcription factor and preventing the STAT transcription factor from becoming dephosphorylated.

133. The method of one of embodiments 71 to 125, further comprising allowing the compound to contact a phosphorylated STAT3 transcription factor and preventing the STAT3 transcription factor from becoming dephosphorylated.

134. The method of one of embodiments 71 to 125, further comprising allowing the compound to contact a phosphorylated STAT transcription factor and preventing the STAT transcription factor from binding genomic DNA.

135. The method of one of embodiments 71 to 125, further comprising allowing the compound to contact a phosphorylated STAT3 transcription factor and preventing the STAT3 transcription factor from binding genomic DNA.

136. The method of one of embodiments 71 to 135, further comprising reducing the level of a STAT transcription factor in a cell.

137. The method of one of embodiments 71 to 135, further comprising reducing the level of a STAT3 transcription factor in a cell.

138. The method of one of embodiments 71 to 135, further comprising reducing the level of a phosphorylated STAT transcription factor in a cell.

139. The method of one of embodiments 71 to 135, further comprising reducing the level of a phosphorylated STAT3 transcription factor in a cell.

140. The method of one of embodiments 71 to 135, further comprising reducing the level of activity of a STAT transcription factor in a cell.

141. The method of one of embodiments 71 to 135, further comprising reducing the level of activity of a STAT3 transcription factor in a cell.

142. The method of one of embodiments 71 to 135, further comprising increasing the level of activity of TLR9 in a cell.

143. The method of one of embodiments 71 to 135, further comprising increasing the level of activity of TLR9 in a disease associated cell.

144. The method of one of embodiments 71 to 135, further comprising increasing the level of activity of TLR9 in a cancer cell.

145. The method of one of embodiments 71 to 135, further comprising increasing the level of activity of TLR9 in a cancer cell, wherein the cancer cell is a leukemia cell, lymphoma cell, myeloma cell, solid tumor cell, acute myeloid leukemia (AML) cell, B cell lymphoma cell, multiple myeloma cell, prostate cancer cell, or glioblastoma cell.

146. The method of one of embodiments 71 to 145, further comprising reducing the level of Arginase-1 in a cell.

147. The method of one of embodiments 71 to 145, further comprising increasing the proliferation of T cells.

148. The method of one of embodiments 71 to 145, further comprising reducing the level of CD80 in a cell.

149. The method of one of embodiments 71 to 145, further comprising reducing the level of CD86 in a cell.

150. The method of one of embodiments 71 to 145, further comprising reducing the level of CD48 in a cell.

151. The method of one of embodiments 71 to 145, further comprising reducing the level of PDL-1 in a cell.

152. The method of one of embodiments 71 to 145, further comprising reducing the level of CD25+ cells.

153. The method of one of embodiments 71 to 145, further comprising reducing the level of CTLA4+ cells.

154. The method of one of embodiments 71 to 145, further comprising increasing the level of CD28 in a cell.

155. The method of one of embodiments 71 to 145, further comprising reducing the level of CD15+ cells.

156. The method of one of embodiments 71 to 145, further comprising reducing the level of CD15+ granulocytes.

157. The method of one of embodiments 71 to 156, comprising systemic administration of the compound.

158. The method of one of embodiments 71 to 156, comprising parenteral administration of the compound.

159. The method of one of embodiments 71 to 156, comprising intravenous administration of the compound.

160. The method of one of embodiments 71 to 156, comprising local administration of the compound to the disease associated cells.

161. A compound of one of embodiments 1 to 67 for use in the treatment of a cancer in a subject in need of such treatment, the use comprising administering a therapeutically effective amount of the compound.

162. The use of embodiment 161, wherein the cancer is a hematopoietic cell cancer.

163. The use of embodiment 161, wherein the cancer is not a hematopoietic cell cancer.

164. The use of embodiment 161, wherein the cancer is leukemia.

165. The use of embodiment 161, wherein the cancer is acute myeloid leukemia.

166. The use of embodiment 161, wherein the cancer is a solid cancer.

167. The use of embodiment 161, wherein the cancer is a carcinoma.

168. The use of embodiment 161, wherein the cancer is prostate cancer.

169. The use of embodiment 161, wherein the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

170. A compound of one of embodiments 1 to 67 for use in the treatment of an infectious disease in a subject in need of such treatment, the use comprising administering a therapeutically effective amount of the compound.

171. The use of embodiment 170, wherein the infectious disease is viral disease.

172. The use of embodiment 170, wherein the infectious disease a herpesvirus associated disease.

173. The use of embodiment 170, wherein the infectious disease a herpesvirus associated disease, wherein the herpesvirus is HHV-1, HHV-2, HHV-3, HHV-4, HHV-5, HHV-6A, HHV-6B, HHV-7, or HHV-8.

174. The use of embodiment 170, wherein the infectious disease is an HIV associated disease.

175. The use of embodiment 170, wherein the infectious disease is HIV infection.

176. The use of embodiment 170, wherein the infectious disease is a hepatitis virus associated disease.

177. The use of embodiment 170, wherein the infectious disease is a hepatitis virus associated disease, wherein the hepatitis virus is hepatitis A virus, hepatitis B virus, hepatitis C virus, hepatitis D virus, or hepatitis E virus.

178. A compound of one of embodiments 1 to 67 for use in inhibiting the growth of a cancer cell comprising contacting the cancer cell with the compound.

179. The use of embodiment 178, wherein the cancer cell comprises a level of TLR9 greater than a non-cancerous cell control.

180. The use of embodiment 178, wherein the cancer cell comprises a level of STAT3 greater than a non-cancerous cell control.

181. A compound of one of embodiments 1 to 67 for use in stimulating the immune system of a patient in need thereof comprising administering an effective amount of the compound to the patient.

182. The use of embodiment 181, wherein the stimulating comprises maturation, differentiation, or proliferation of natural killer cells, T cells, monocytes, or macrophages.

183. The use of embodiment 181, wherein the stimulating comprises an increase in TH1-type immune responses.

184. The use of embodiment 181, wherein the stimulating comprises an increase in CD8+ cells.

185. The use of embodiment 181, wherein the stimulating comprises a decrease in regulatory cells.

186. The use of embodiment 181, wherein the stimulating comprises a decrease in suppressor cells.

187. The use of embodiment 181, wherein the stimulating comprises a decrease in myeloid suppressor cells.

188. The use of embodiment 181, wherein the stimulating comprises an increase in CD8+ cells.

189. The use of embodiment 181, wherein the stimulating comprises a decrease in CD4+/FoxP3+ cells.

190. A compound of one of embodiments 1 to 67 for use in stimulating the immune system of a patient in need thereof to recognize disease associated cells, comprising administering an effective amount of the composition to the patient.

191. A compound of one of embodiments 1 to 67 for use in stimulating the immune system of a patient in need thereof to recognize disease associated cells, comprising administering an effective amount of the compound to the patient, wherein the disease associated cell is a cancer cell, cancer stem cell, or infected cell.

192. A compound of one of embodiments 1 to 67 for use in reducing the activity of a STAT transcription factor in a cell comprising contacting the cell with the compound.

193. The use of embodiment 192, wherein the STAT transcription factor is STAT3.

194. A use of increasing apoptosis of a cell comprising contacting the cell with a compound of one of embodiments 1 to 67.

195. A use of inducing apoptosis of a cell comprising contacting the cell with a compound of one of embodiments 1 to 67.

196. The use of one of embodiments 161 to 195, further comprising contacting a plasmacytoid dendritic cell, myeloid dendritic cell, myeloid-derived suppressor cell, granulocytic myeloid-derived suppressor cell, macrophage, T Cell, B cell, activated NK cell, or activated neutrophil with the compound.

197. The use of one of embodiments 161 to 195, further comprising contacting a plasmacytoid with the compound.

198. The use of one of embodiments 161 to 195, further comprising contacting a dendritic cell with the compound.

199. The use of one of embodiments 161 to 195, further comprising contacting a myeloid dendritic cell with the compound.

200. The use of one of embodiments 161 to 195, further comprising contacting a myeloid-derived suppressor cell with the compound.

201. The use of one of embodiments 161 to 195, further comprising contacting a granulocytic myeloid-derived suppressor cell with the compound.

202. The use of one of embodiments 161 to 195, further comprising contacting a macrophage with the compound.

203. The use of one of embodiments 161 to 195, further comprising contacting a T Cell with the compound.

204. The use of one of embodiments 161 to 195, further comprising contacting a B cell with the compound.

205. The use of one of embodiments 161 to 195, further comprising contacting an activated NK cell with the compound.

206. The use of one of embodiments 161 to 195, further comprising contacting an activated neutrophil with the compound.

207. The use of one of embodiments 161 to 206, further comprising allowing the compound to contact a STAT transcription factor.

208. The use of one of embodiments 161 to 206, further comprising allowing the compound to contact a STAT transcription factor, wherein the STAT transcription factor is STAT1, STAT2, STAT3, STAT4, STAT5A, STAT5B, or STAT6.

209. The use of one of embodiments 161 to 206, further comprising allowing the compound to contact STAT1.

210. The use of one of embodiments 161 to 206, further comprising allowing the compound to contact STAT2.

211. The use of one of embodiments 161 to 206, further comprising allowing the compound to contact STAT3.

212. The use of one of embodiments 161 to 206, further comprising allowing the compound to contact STAT4.

213. The use of one of embodiments 161 to 206, further comprising allowing the compound to contact STAT5A.

214. The use of one of embodiments 161 to 206, further comprising allowing the compound to contact STAT5B.

215. The use of one of embodiments 161 to 206, further comprising allowing the compound to contact STAT6.

216. The use of one of embodiments 161 to 206, further comprising allowing the compound to contact a phosphorylated STAT transcription factor.

217. The use of one of embodiments 161 to 206, further comprising allowing the compound to contact a phosphorylated STAT3 transcription factor.

218. The use of one of embodiments 161 to 206, further comprising allowing the compound to contact a phosphorylated STAT transcription factor in the cytosol of a cell.

219. The use of one of embodiments 161 to 206, further comprising allowing the compound to contact a phosphorylated STAT3 transcription factor in the cytosol of a cell.

220. The use of one of embodiments 161 to 206, further comprising allowing the compound to contact a phosphorylated STAT transcription factor and preventing the STAT transcription factor from entering the nucleus.

221. The use of one of embodiments 161 to 206, further comprising allowing the compound to contact a phosphorylated STAT3 transcription factor and preventing the STAT3 transcription factor from entering the nucleus.

222. The use of one of embodiments 161 to 206, further comprising allowing the compound to contact a phosphorylated STAT transcription factor and preventing the STAT transcription factor from becoming dephosphorylated.

223. The use of one of embodiments 161 to 206, further comprising allowing the compound to contact a phosphorylated STAT3 transcription factor and preventing the STAT3 transcription factor from becoming dephosphorylated.

224. The use of one of embodiments 161 to 206, further comprising allowing the compound to contact a phosphorylated STAT transcription factor and preventing the STAT transcription factor from binding genomic DNA.

225. The use of one of embodiments 161 to 206, further comprising allowing the compound to contact a phosphorylated STAT3 transcription factor and preventing the STAT3 transcription factor from binding genomic DNA.

226. The use of one of embodiments 161 to 225, further comprising reducing the level of a STAT transcription factor in a cell.

227. The use of one of embodiments 161 to 225, further comprising reducing the level of a STAT3 transcription factor in a cell.

228. The use of one of embodiments 161 to 225, further comprising reducing the level of a phosphorylated STAT transcription factor in a cell.

229. The use of one of embodiments 161 to 225, further comprising reducing the level of a phosphorylated STAT3 transcription factor in a cell.

230. The use of one of embodiments 161 to 225, further comprising reducing the level of activity of a STAT transcription factor in a cell.

231. The use of one of embodiments 161 to 225, further comprising reducing the level of activity of a STAT3 transcription factor in a cell.

232. The use of one of embodiments 161 to 231, further comprising increasing the level of activity of TLR9 in a cell.

233. The use of one of embodiments 161 to 231, further comprising increasing the level of activity of TLR9 in a disease associated cell.

234. The use of one of embodiments 161 to 231, further comprising increasing the level of activity of TLR9 in a cancer cell.

235. The use of one of embodiments 161 to 231, further comprising increasing the level of activity of TLR9 in a cancer cell, wherein the cancer cell is a leukemia cell, lymphoma cell, myeloma cell, solid tumor cell, acute myeloid leukemia (AML) cell, B cell lymphoma cell, multiple myeloma cell, prostate cancer cell, or glioblastoma cell.

236. The use of one of embodiments 161 to 235, further comprising reducing the level of Arginase-1 in a cell.

237. The use of one of embodiments 161 to 235, further comprising increasing the proliferation of T cells.

238. The use of one of embodiments 161 to 235, further comprising reducing the level of CD80 in a cell.

239. The use of one of embodiments 161 to 235, further comprising reducing the level of CD86 in a cell.

240. The use of one of embodiments 161 to 235, further comprising reducing the level of CD48 in a cell.

241. The use of one of embodiments 161 to 235, further comprising reducing the level of PDL-1 in a cell.

242. The use of one of embodiments 161 to 235, further comprising reducing the level of CD25+ cells.

243. The use of one of embodiments 161 to 235, further comprising reducing the level of CTLA4+ cells.

244. The use of one of embodiments 161 to 235, further comprising increasing the level of CD28 in a cell.

245. The use of one of embodiments 161 to 235, further comprising reducing the level of CD15+ cells.

246. The use of one of embodiments 161 to 235, further comprising reducing the level of CD15+ granulocytes.

247. The use of one of embodiments 161 to 246, comprising systemic administration of the compound.

248. The use of one of embodiments 161 to 246, comprising parenteral administration of the compound.

249. The use of one of embodiments 161 to 246, comprising intravenous administration of the compound.

250. The use of one of embodiments 161 to 246, comprising local administration of the compound to the disease associated cells.

251. Use of a compound of one of embodiments 1 to 67 in the manufacture of a medicament for treatment of a cancer in a subject in need of such treatment, the use comprising administering a therapeutically effective amount of the compound.

252. The use of embodiment 251, wherein the cancer is a hematopoietic cell cancer.

253. The use of embodiment 251, wherein the cancer is not a hematopoietic cell cancer.

254. The use of embodiment 251, wherein the cancer is leukemia.

255. The use of embodiment 251, wherein the cancer is acute myeloid leukemia.

256. The use of embodiment 251, wherein the cancer is a solid cancer.

257. The use of embodiment 251, wherein the cancer is a carcinoma.

258. The use of embodiment 251, wherein the cancer is prostate cancer.

259. The use of embodiment 251, wherein the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

260. Use of a compound of one of embodiments 1 to 67 in the manufacture of a medicament for treatment of an infectious disease in a subject in need of such treatment, the use comprising administering a therapeutically effective amount of the compound.

261. The use of embodiment 260, wherein the infectious disease is viral disease.

262. The use of embodiment 260, wherein the infectious disease a herpesvirus associated disease.

263. The use of embodiment 260, wherein the infectious disease a herpesvirus associated disease, wherein the herpesvirus is HHV-1, HHV-2, HHV-3, HHV-4, HHV-5, HHV-6A, HHV-6B, HHV-7, or HHV-8.

264. The use of embodiment 260, wherein the infectious disease is an HIV associated disease.

265. The use of embodiment 260, wherein the infectious disease is HIV infection.

266. The use of embodiment 260, wherein the infectious disease is a hepatitis virus associated disease.

267. The use of embodiment 260, wherein the infectious disease is a hepatitis virus associated disease, wherein the hepatitis virus is hepatitis A virus, hepatitis B virus, hepatitis C virus, hepatitis D virus, or hepatitis E virus.

268. Use of a compound of one of embodiments 1 to 67 in the manufacture of a medicament for inhibiting the growth of a cancer cell comprising contacting the cancer cell with the compound.

269. The use of embodiment 268, wherein the cancer cell comprises a level of TLR9 greater than a non-cancerous cell control.

270. The use of embodiment 268, wherein the cancer cell comprises a level of STAT3 greater than a non-cancerous cell control.

271. Use of a compound of one of embodiments 1 to 67 in the manufacture of a medicament for stimulating the immune system of a patient in need thereof comprising administering an effective amount of the compound to the patient.

272. The use of embodiment 271, wherein the stimulating comprises maturation, differentiation, or proliferation of natural killer cells, T cells, monocytes, or macrophages.

273. The use of embodiment 271, wherein the stimulating comprises an increase in TH1-type immune responses.

274. The use of embodiment 271, wherein the stimulating comprises an increase in CD8+ cells.

275. The use of embodiment 271, wherein the stimulating comprises a decrease in regulatory cells.

276. The use of embodiment 271, wherein the stimulating comprises a decrease in suppressor cells.

277. The use of embodiment 271, wherein the stimulating comprises a decrease in myeloid suppressor cells.

278. The use of embodiment 271, wherein the stimulating comprises an increase in CD8+ cells.

279. The use of embodiment 271, wherein the stimulating comprises a decrease in CD4+/FoxP3+ cells.

280. Use of a compound of one of embodiments 1 to 67 in the manufacture of a medicament for stimulating the immune system of a patient in need thereof to recognize disease associated cells, comprising administering an effective amount of the composition to the patient.

281. Use of a compound of one of embodiments 1 to 67 in the manufacture of a medicament for stimulating the immune system of a patient in need thereof to recognize disease associated cells, comprising administering an effective amount of the compound to the patient, wherein the disease associated cell is a cancer cell, cancer stem cell, or infected cell.

282. Use of a compound of one of embodiments 1 to 67 in the manufacture of a medicament for reducing the activity of a STAT transcription factor in a cell comprising contacting the cell with the compound.

283. The use of embodiment 282, wherein the STAT transcription factor is STAT3.

284. Use of a compound of one of embodiments 1 to 67 in the manufacture of a medicament for increasing apoptosis of a cell comprising contacting the cell with the compound.

285. Use of a compound of one of embodiments 1 to 67 in the manufacture of a medicament for inducing apoptosis of a cell comprising contacting the cell with the compound.

EXAMPLES

Example A

Figure 1C:
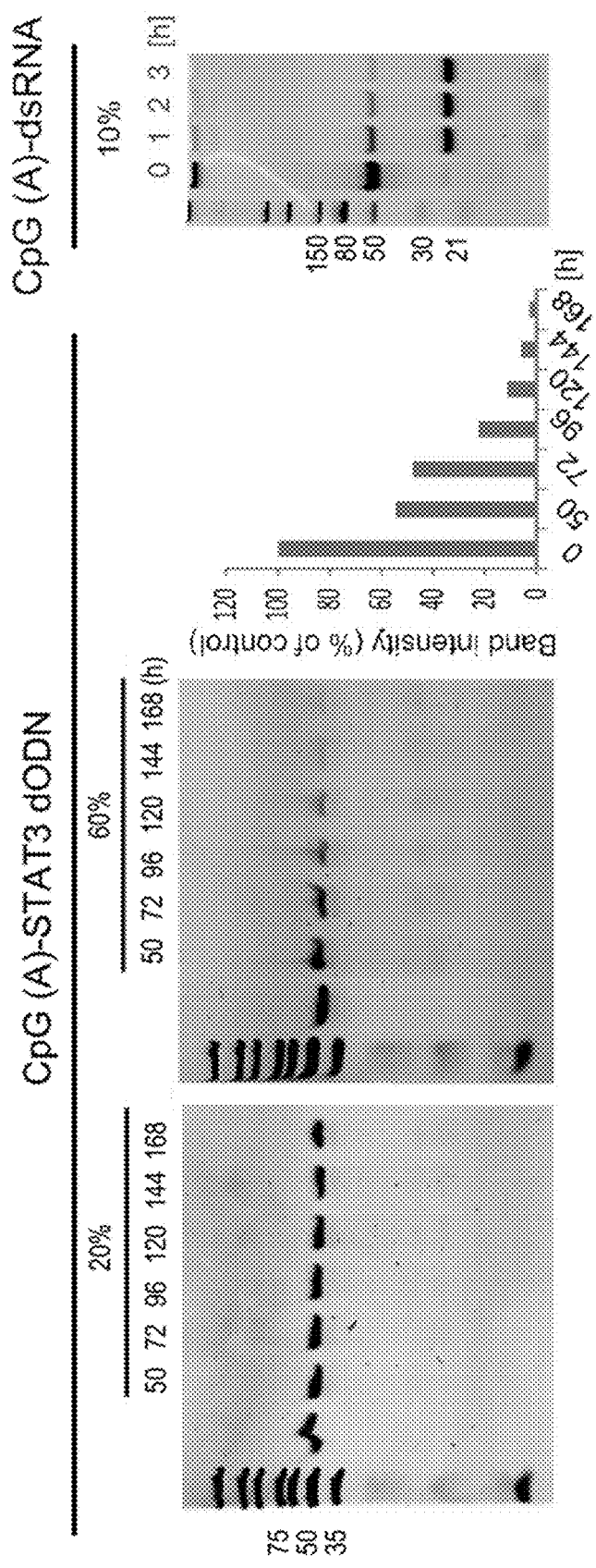

Design of CpG-STAT3 decoy oligodeoxynucleotide (dODN) and Chemical Modification for Enhanced Serum Stability Sequence of the single stranded CpG-STAT3 dODN conjugate (MW=17,757 g/mol) (FIG. 1A). Asterisks indicate phosphothioation sites in the conjugate backbone; x=single unit of the C3 carbon chain $(CH_2)_3$ (Glen Research) or combined x's equal an alkylphosphate (e.g. 5x is n=4 or 5x is n1=4, as n and n1 and n2 are used herein for alkylphosphates). Predicted hairpin structure of the folded CpG-STAT3 dODN with both parts of the conjugate indicated (FIG. 1B), wherein o=x (e.g. C3 carbon chain or alkylphosphate) as in FIG. 1A. Chemically-modified CpG-STAT3 dODN has improved resistance to degradation in human serum (FIG. 1C). Left two panels of FIG. 1C—CpG-STAT3 dODN was incubated in 20% (right panel) or 60% (middle panel) human serum for up to 168 h (1 week), then resolved on 7.5M Urea/15% PAGE gel and stained using ethidium bromide. Bar graph shows quantification of band intensities in the middle panel. The estimated half-life of CpG(A)-STAT3dODN in 60% human serum exceeds 2 days. Right panel of FIG. 1C—incubation of the control CpG-dsRNA in similar conditions results in conjugate cleavage already after 1 h. Shown are results from one of three independent experiments.

Example B

Figure 2:
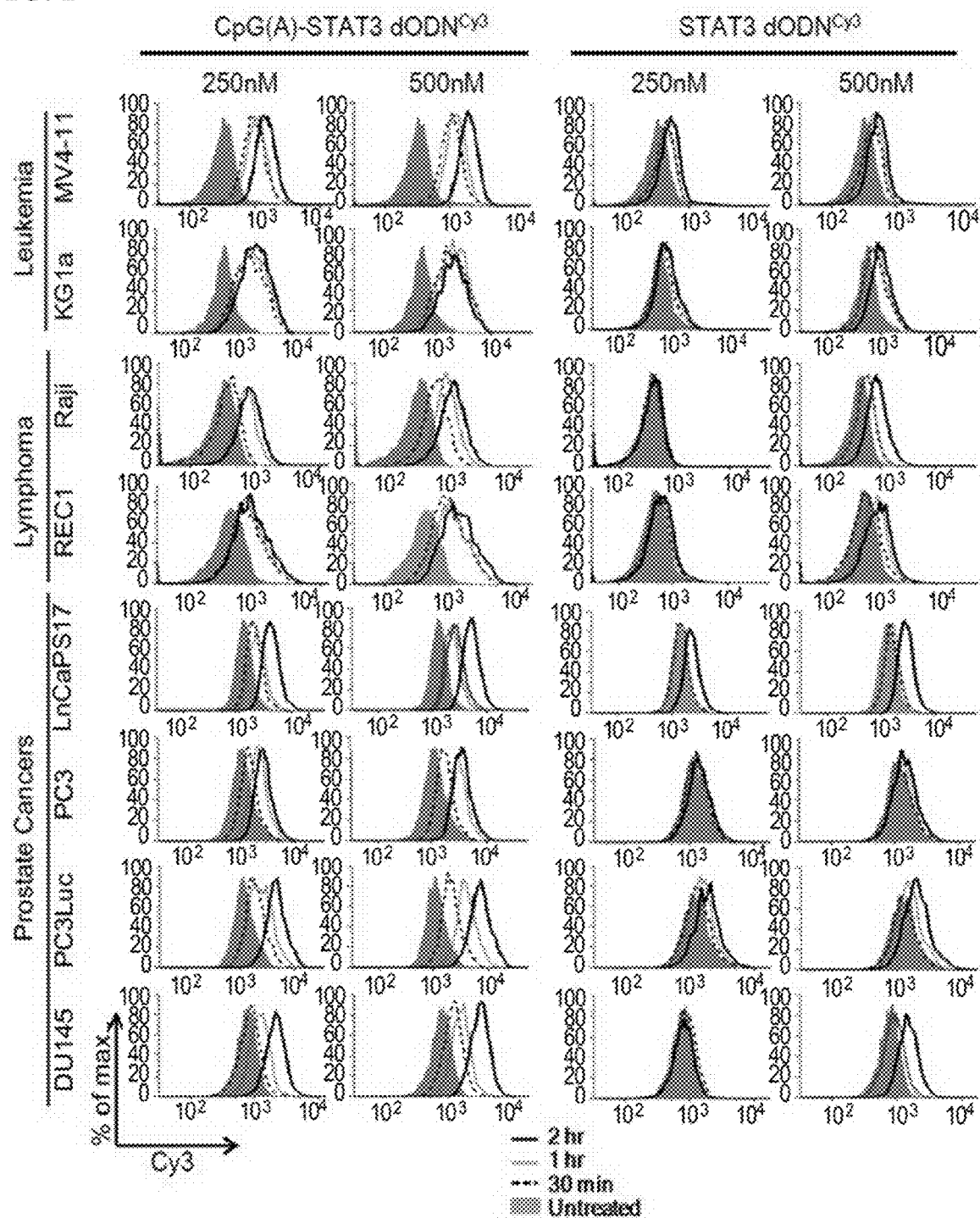
FIG. 2. CpG-STAT3 dODN conjugates but not unconjugated STAT3 dODN are quickly internalized by various target human cancer cells in vitro.

CpG-STAT3 dODN Conjugates but not Unconjugated STAT3 dODN are Quickly Internalized by Various Target Human Cancer Cells in vitro Human acute myeloid leukemia, B cell lymphoma and prostate cancer cells were incubated with two doses of fluorescently-labeled CpG-STAT3 dODN (left two columns of FIG. 2) or STAT3 dODN alone (right two columns of FIG. 2) for indicated times without any transfection reagents. Percentages of Cy3-positive cells were assessed using flow cytometry (FIG. 2).

Example C

Figure 3A:
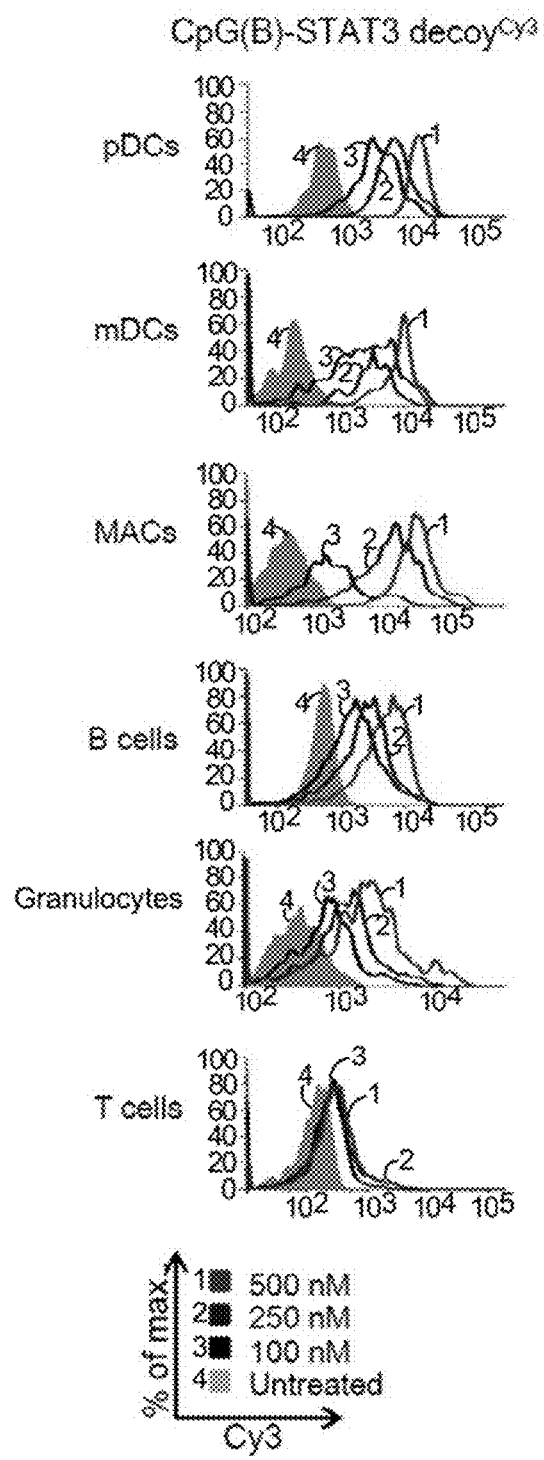
FIGS. 3A-3C. Targeted delivery of CpG-STAT3 dODN into mouse immune cells and cancer cells in vitro.
Figure 3B:
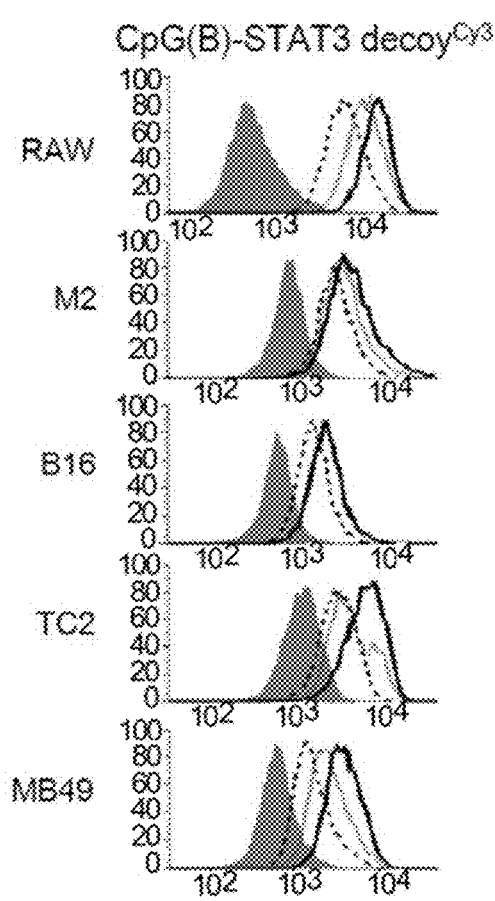
Figure 3C:
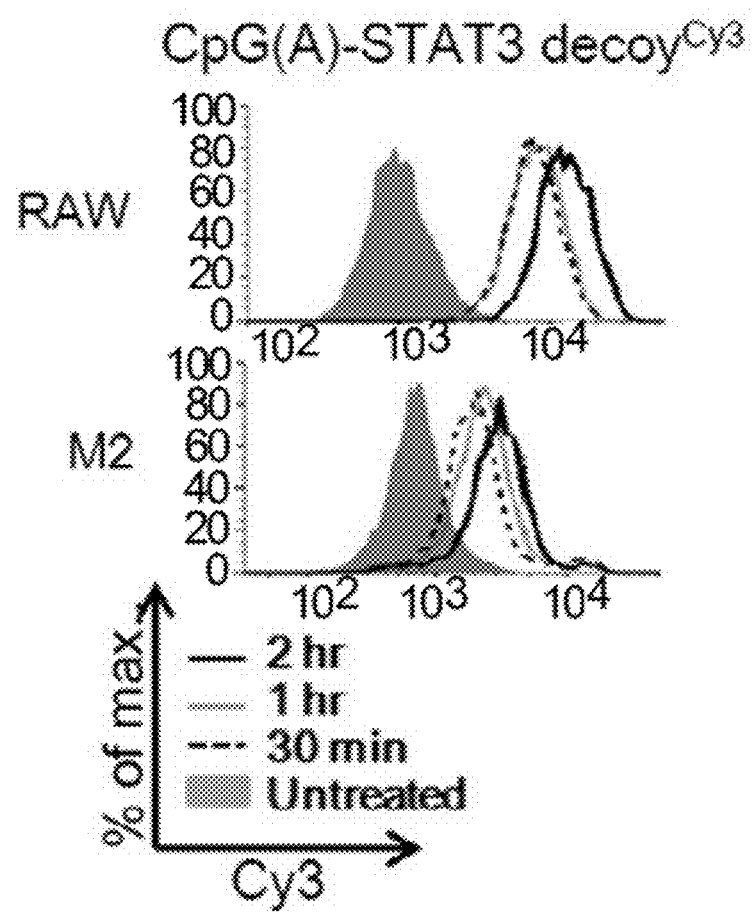

Targeted Delivery of CpG-STAT3 dODN into Mouse Immune Cells and Cancer Cells in vitro Mouse splenocytes were incubated with fluorescently-labeled CpG-STAT3 dODN in indicated concentrations for 2 h without any transfection reagents (FIG. 3A). Percentages of Cy3-positive cells pDCs (CD11c+B220+), mDCs (CD11c+B220−), macrophages (MAC; F4/80+Gr1−), B cells (B220+CD11c−), granulocytes (Gr1+F4/80−) and T cells (CD3+) were assessed using flow cytometry (FIG. 3A). Rapid internalization of CpG-STAT3 dODN by transformed mouse macrophages (RAW264.7) and various types of mouse cancer cells, such as M2 and B16 melanoma, TC2 neuroendocrine and MB49 bladder cancer cells (FIG. 3B). Cell were incubated in the presence of 500 nM of CpG(B)-STAT3 dODN conjugate, which uses B-type CpG sequence optimized for immunostimulation in mice. CpG(A)-STAT3 dODN, with A-type CpG sequence optimized for immunostimulation of human cells is internalized with similar efficiency as CpG(B)-STAT3 dODN by mouse macrophages and cancer cells (FIG. 3C).

Example D

Figure 4B:
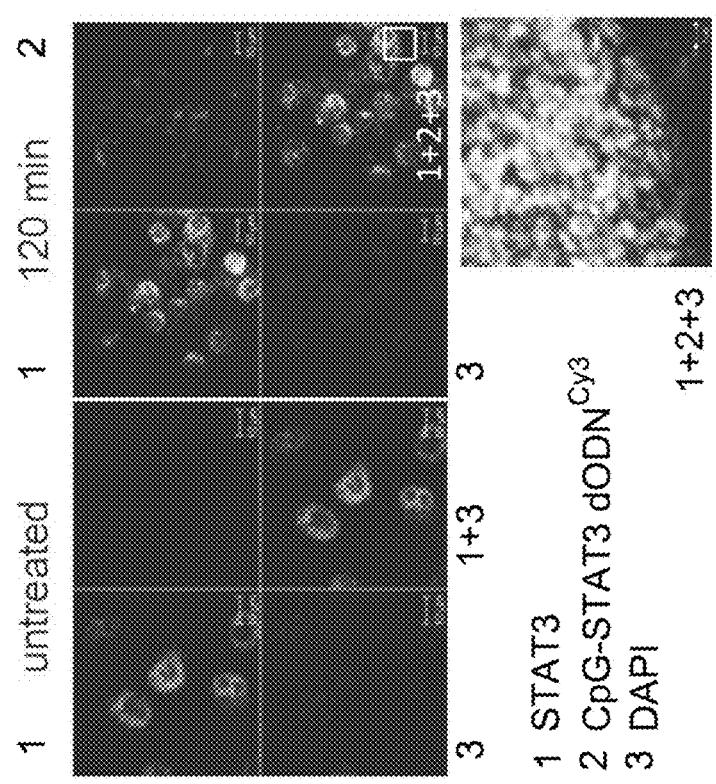
FIGS. 4A-4B. CpG-STAT3 dODN colocalized with STAT3 protein shortly after intracellular uptake into early endosomes. Mouse RAW264.7 macrophages were incubated with fluorescently-labeled CpG-STAT3 dODNCy3 at 500 nM concentration for 30 min (FIG. 4A) and 120 min (FIG. B) then fixed and permeabilized for immunostaining using antibodies specific to early endosome marker EEA1 (FIG. 4A) or to STAT3 (FIG. 4B) and counterstained using DAPi to visualize nuclei. The intracellular localization of CpG-STAT3 dODN was analyzed using confocal microscopy.
Figure 4A:
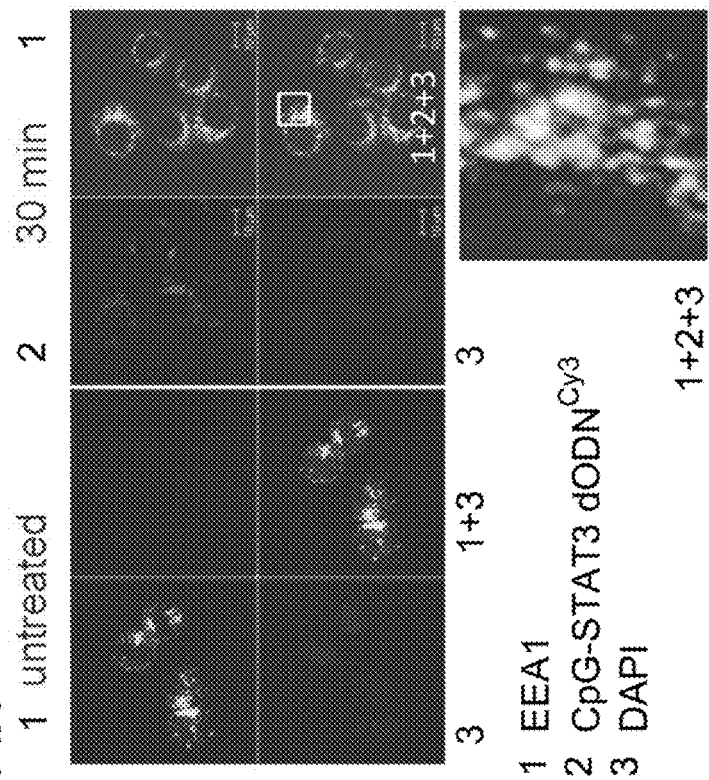

CpG-STAT3 dODN Colocalized with STAT3 Protein Shortly After Intracellular Uptake into Early Endosomes Mouse RAW264.7 macrophages were incubated with fluorescently-labeled CpG-STAT3 dODNCy3 at 500 nM concentration for 30 min (A) and 120 min (B) then fixed and permeabilized for immunostaining using antibodies specific to early endosome marker EEA1 (FIG. 4A) or to STAT3 (FIG. 4B) and counterstained using DAPi to visualize nuclei. The intracellular localization of CpG-STAT3 dODN was analyzed using confocal microscopy. Shown in FIGS. 4A-4B are representative images from one of two independent experiments.

Example E

Figure 5:
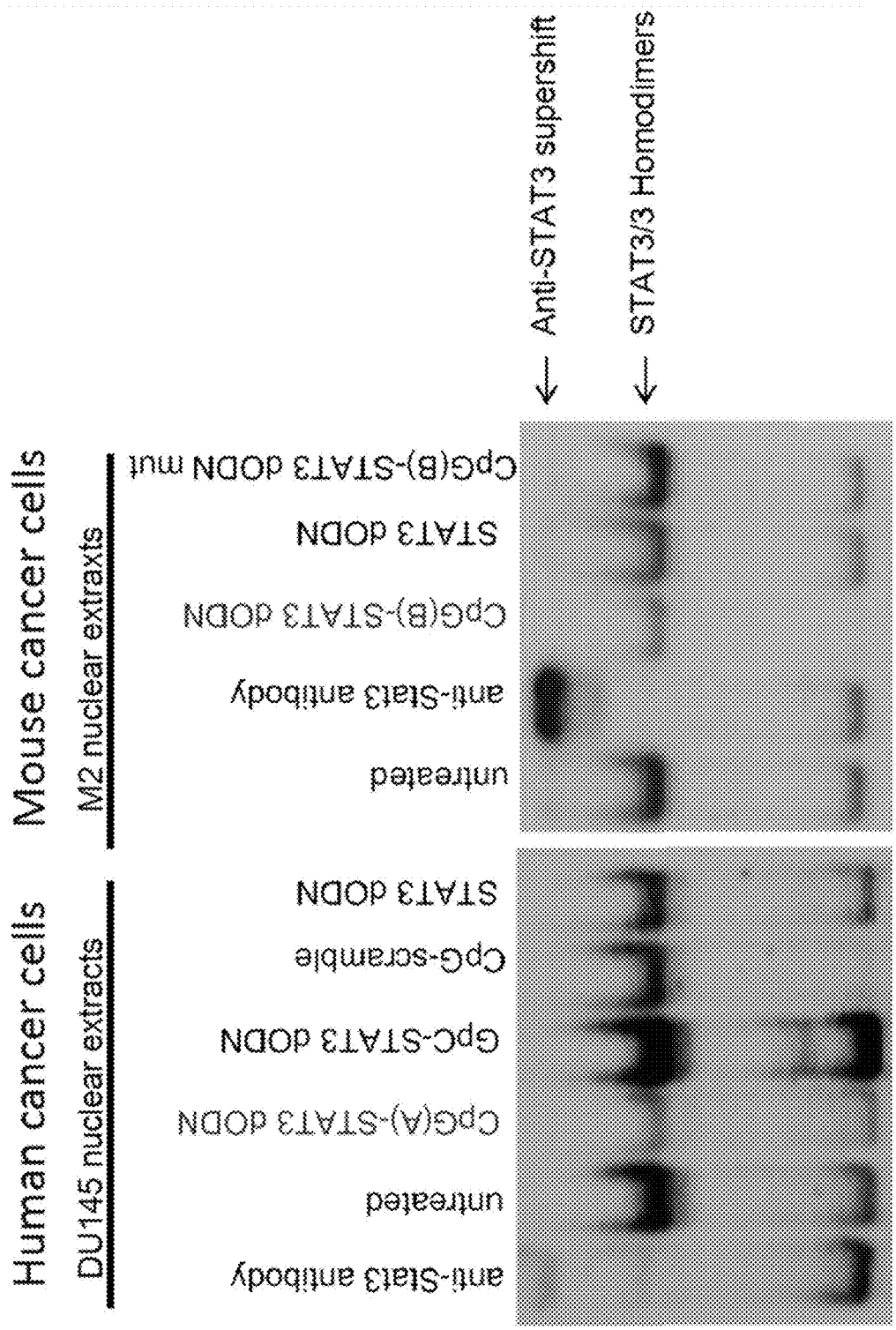
FIG. 5. CpG-STAT3 dODN conjugates inhibit DNA binding of STAT3 in target human and mouse cancer cells.

CpG-STAT3 dODN Conjugates Inhibit DNA Binding of STAT3 in Target Human and Mouse Cancer Cells Human DU145 prostate cancer cells and mouse M2 melanoma cells were incubated in the presence of 500 nM of various CpG-dODN conjugates or unconjugated dODN (FIG. 5). Cells were then lysed to isolate nuclear extracts and the DNA binding of STAT3 was assessed using electromobility shift assay (EMSA). The identity of the band representing STAT3 homodimer was verified using antibodies specific to STAT3 as indicated (FIG. 5). Positions of inhibitory CpG-STAT3 dODNs are indicated in gray (CpG(A)-STAT3 dODN, CpG(B)-STAT3 dODN), (FIG. 5).

Example F

Figure 6A:
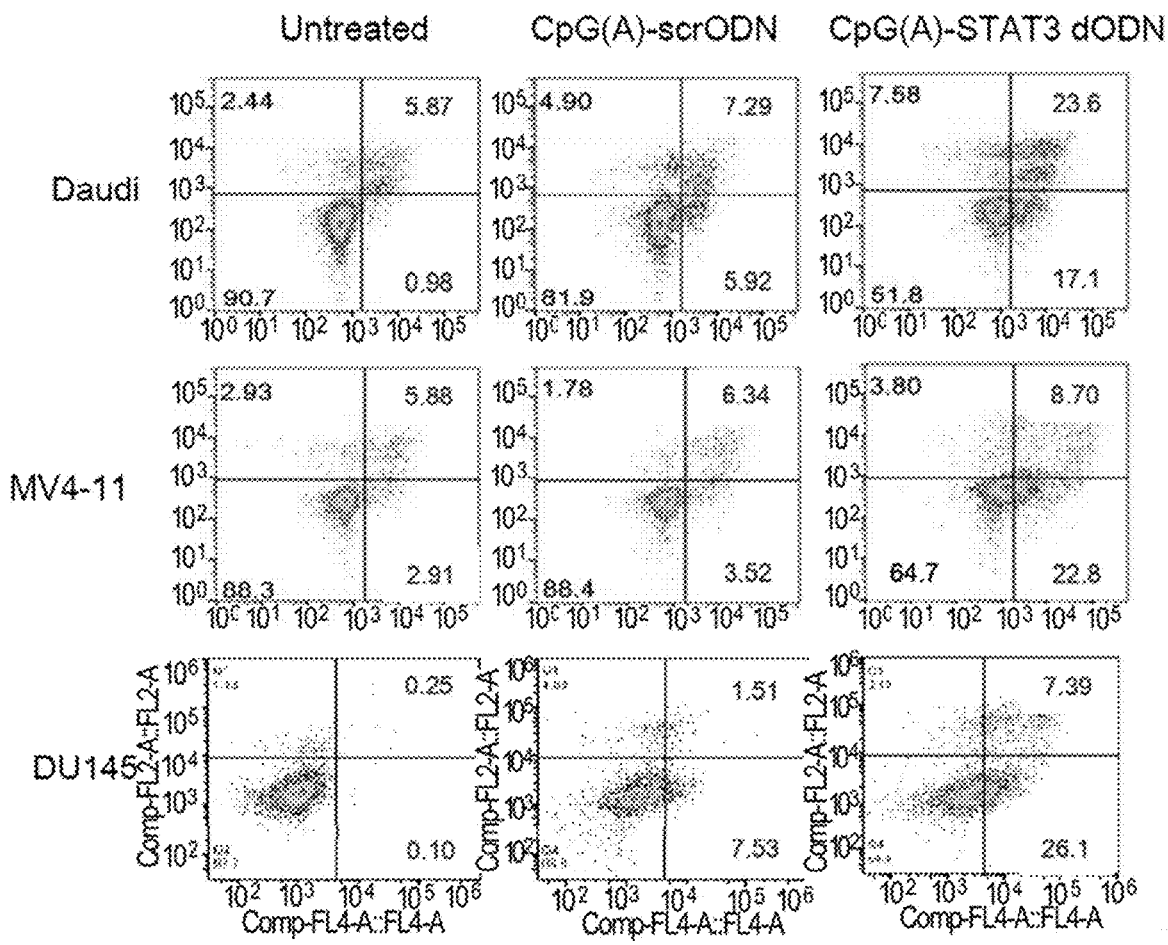
FIGS. 6A-6B. CpG-STAT3 dODN induces direct cytotoxic effects in human and mouse cancer cells in vitro.
Figure 6B:
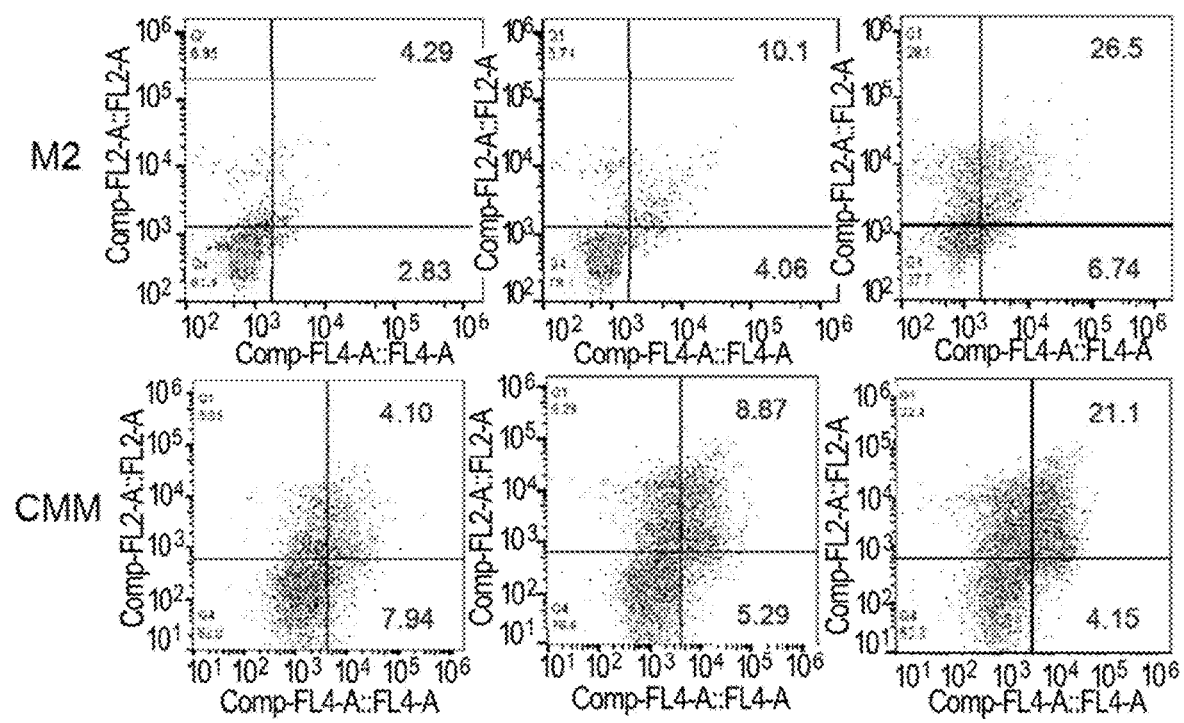

CpG-STAT3 dODN Induces Direct Cytotoxic Effects in Human and Mouse Cancer Cells in vitro Human B cell lymphoma (Daudi), AML (MV4-11) and prostate cancer cells (DU145) were incubated with 500 nM CpG(A)-STAT3 dODN for 2 days (FIG. 6A). The induction of cell death was measured after Annexin V and 7AAD staining using flow cytometry. The percentages of early apoptotic (Annexin V+ 7AAD−) and late apoptotic (Annexin V+ 7AAD+) cells is shown. Mouse M2 melanoma and Cbfb/MYH11 Mp11 AML (CMM) cells were incubated 500 nM CpG(B)-STAT3 dODN for 2 days and analyzed as described as above, (FIG. 6B).

Example G

Figure 7A:
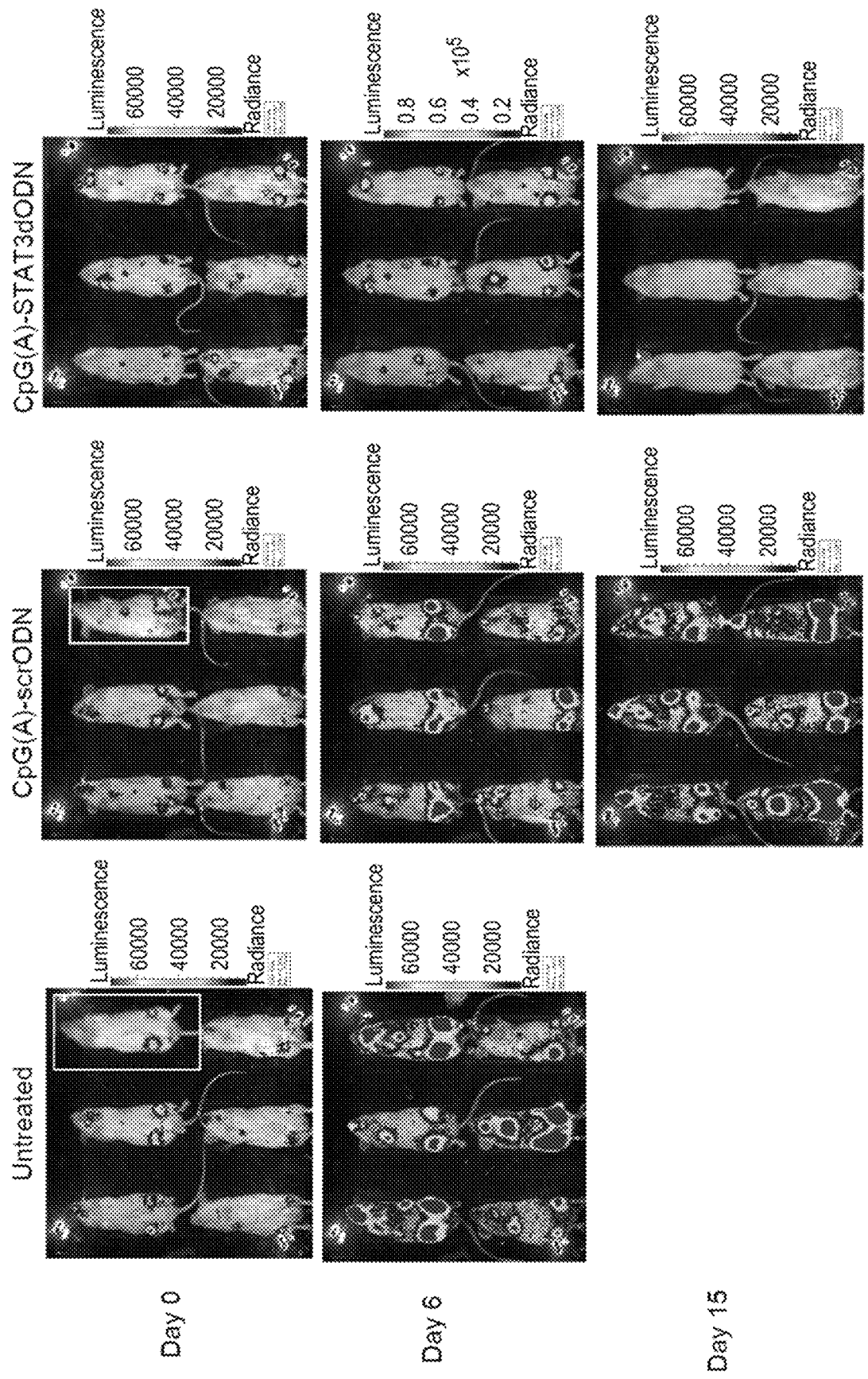
FIGS. 7A-7B. Systemic CpG(A)-STAT3 dODN treatment induces regression of disseminated human MV4-11 leukemia in mice. NSG mice were injected i.v. with $0.5 \times 10^6$ MV4-11luc acute myeloid leukemia cells. After 2-3 weeks when tumors were engrafted as confirmed by Xenogen imaging, mice were injected daily using 5 mg/kg of CpG (A)-STAT3 dODN or negative control CpG(A)-scrODN or left untreated.
Figure 7B:
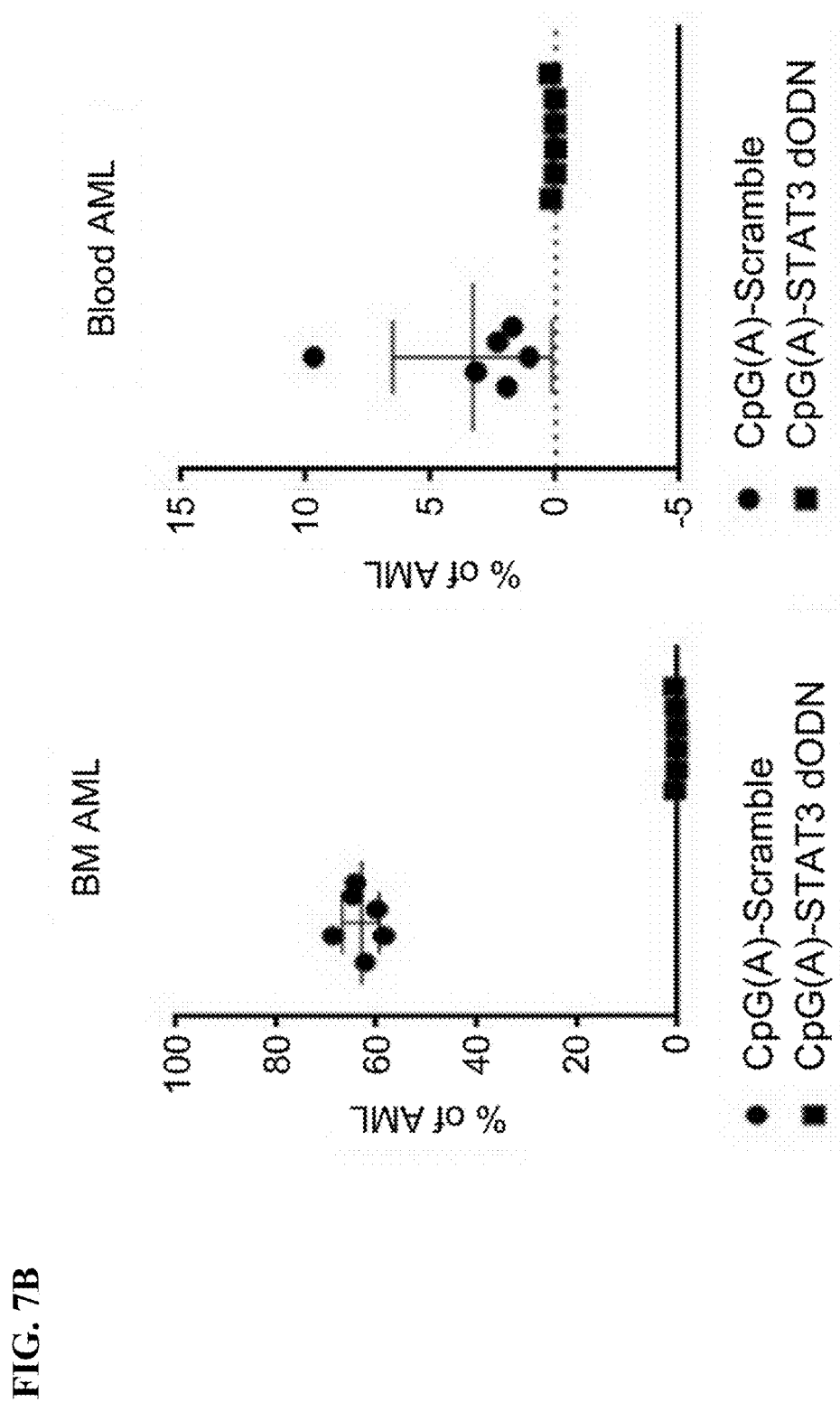

Systemic CpG(A)-STAT3 dODN Treatment Induces Regression of Disseminated Human MV4-11 leukemia in Mice NSG mice were injected i.v. with $0.5 \times 10^6$ MV4-11luc acute myeloid leukemia cells (FIGS. 7A-7B). After 2-3 weeks when tumors were engrafted as confirmed by Xenogen imaging, mice were injected daily using 5 mg/kg of CpG(A)-STAT3 dODN or negative control CpG(A)-scrODN or left untreated. Xenogen imaging before and during treatment to detect AML regression after repeated injections of CpG(A)-STAT3 dODN compared to both control groups (FIG. 7A). CpG(A)-STAT3 dODN treatment reduces the percentage of AML cells in various organs including bone marrow (BM) and blood as assessed using flow cytometry (FIG. 7B). Shown are combined results from 6 mice/group; means±SEM.

Example H

Figure 8A:
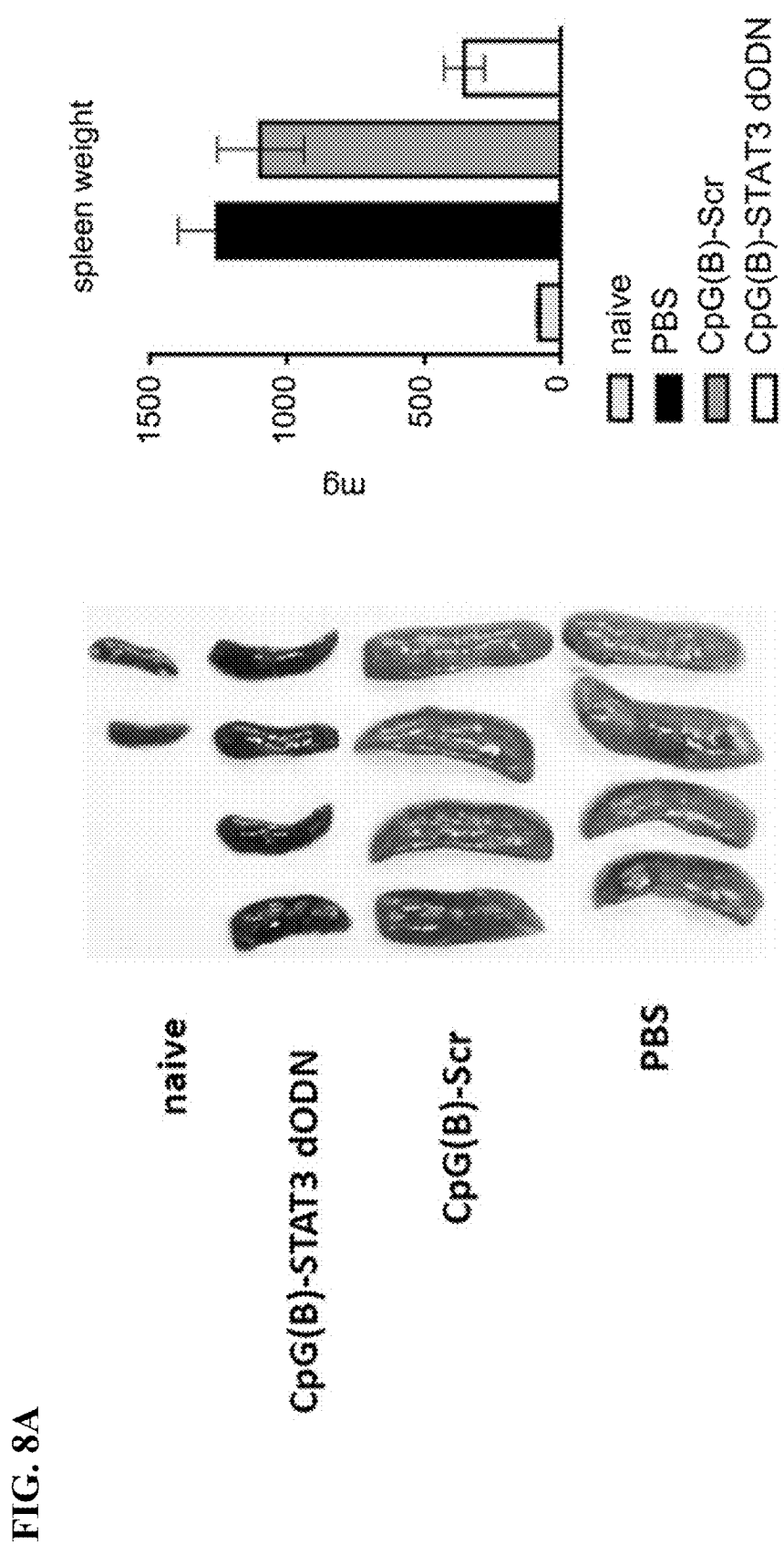
FIGS. 8A-8C. Systemic CpG-STAT3 dODN treatment induces complete regression of mouse Cbfb/MYH11/Mpl leukemia in immunocompetent mice. After 2-3 weeks when tumors were engrafted (>1%, ranging 1-5% of AML cells in blood), mice were injected six times with CpG-Stat3 siRNA or control CpG-Luciferase siRNA (5 mg/kg) every other day and euthanized one day after last treatment.
Figure 8B:
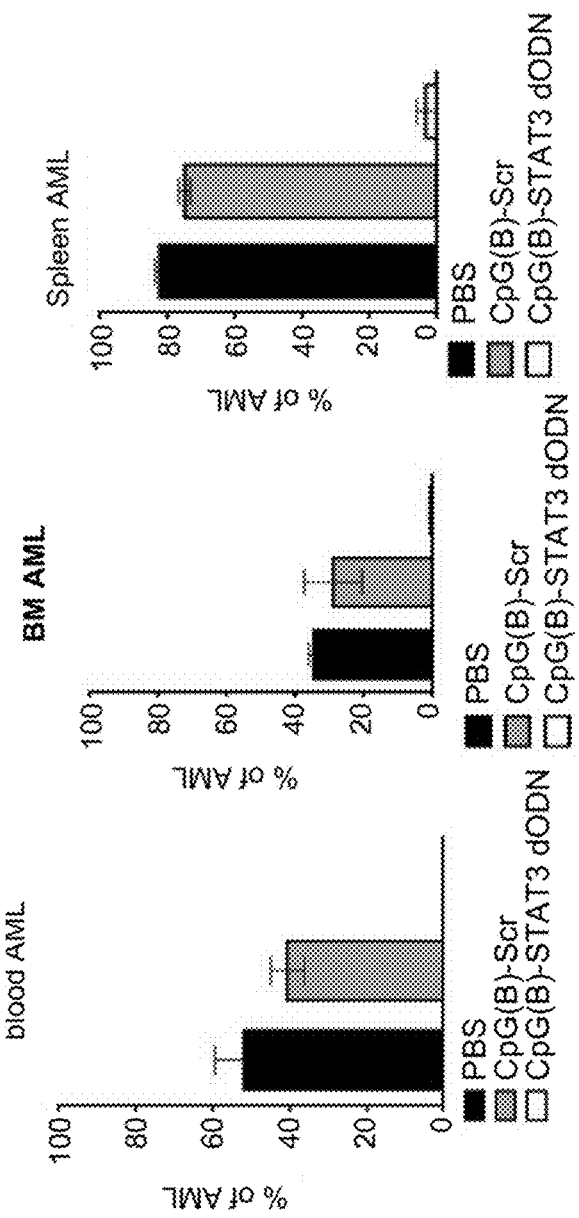
Figure 8C:
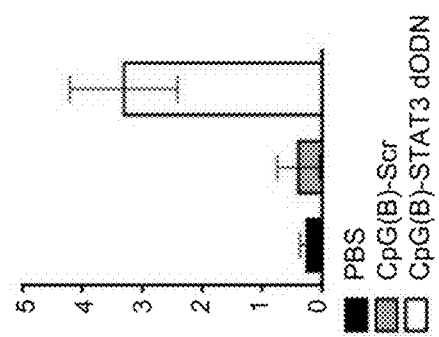

Systemic CpG-STAT3 dODN Treatment Induces Complete Regression of Mouse Cbfb/MYH11/Mpl leukemia in Immunocompetent Mice After 2-3 weeks when tumors were engrafted (>1%, ranging 1-5% of AML cells in blood), mice were injected six times with CpG-Stat3 siRNA or control CpG-Luciferase siRNA (5 mg/kg) every other day and euthanized one day after last treatment (FIGS. 8A-8C). CpG-STAT3 dODN treatment reduces the percentage of AML cells in various organs (FIGS. 8A-8C). The effect of CpG-STAT3 dODN treatments on spleen cellularity (FIG. 8A). Shown are representative spleen sizes (left) and the measurement of spleens weight (right). Flow cytometric analysis of GFP+c-Kit+ AML cells in blood, bone marrows, spleens and the percentage of CD8+ T cells infiltrating spleens from various groups of mice (FIGS. 8B-8C). Shown are combined results from 6 mice/group; means±SEM.

Example I

Figure 9:
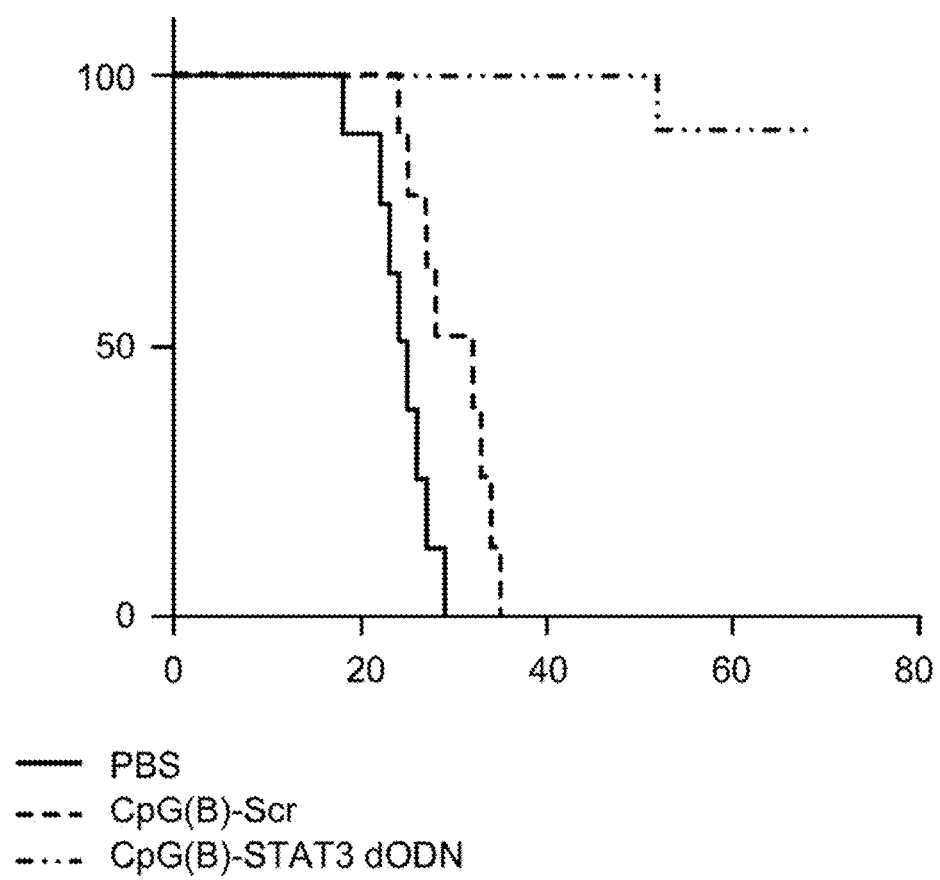
FIG. 9. In vivo administration of CpG-STAT3dODN reduces leukemia-initiating potential of Cbfb/MYH11/Mpl AML cells FIGS. 10A-10C. Intravenously injected CpG-STAT3dODN conjugates are more effective than CpG-Stat3 siRNA against disseminated leukemia in vivo. After 2-3 weeks from tumor challenge, with confirmed AML engraftment (>1%, ranging 1-5% of AML cells in blood), mice were injected iv. only 3 times every other day using 5 mg/kg of CpG(B)-Stat3 siRNA, CpG(A)-STAT3dODN, CpG(B)-STAT3dODN or CpG(B)-scrambled ODN conjugates and euthanized one day after the last treatment. Treatments using both types of CpG-STAT3 dODN were more effective than CpG-Stat3 siRNA in reducing percentages of AML cells in blood (FIG. 10A), lymph nodes (FIG. 10B) and bone marrow (FIG. 10C). Shown are combined results from 6 mice/group; means±SEM.

In vivo Administration of CpG-STAT3dODN Reduces leukemia-initiating Potential of Cbfb/MYH11/Mpl AML Cells AML cells were enriched from spleens of primary recipient mice treated using CpG-STAT3dODN or CpG-scrambled ODN (5 mg/kg) injected i.v. 6 times every other day or untreated as described in FIGS. 8A-8C (FIG. 9). Leukemic cells from each treatment group were pooled, counted and injected at identical cell numbers into secondary recipient mice. Mice survival was monitored daily without any further treatment or intervention. Shown in FIG. 9 are results from a single experiment using 10 mice per each group.

Example J

Figure 10A:
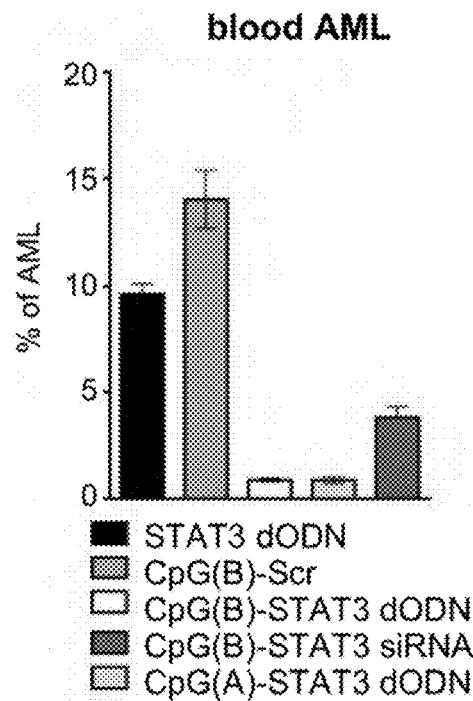
Figure 10B:
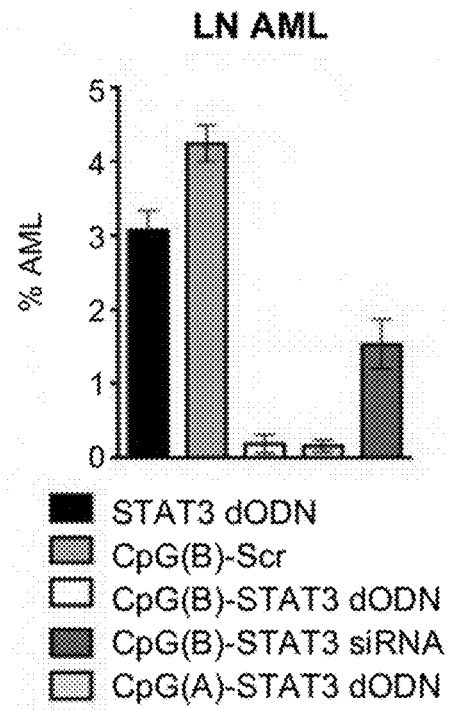
Figure 10C:
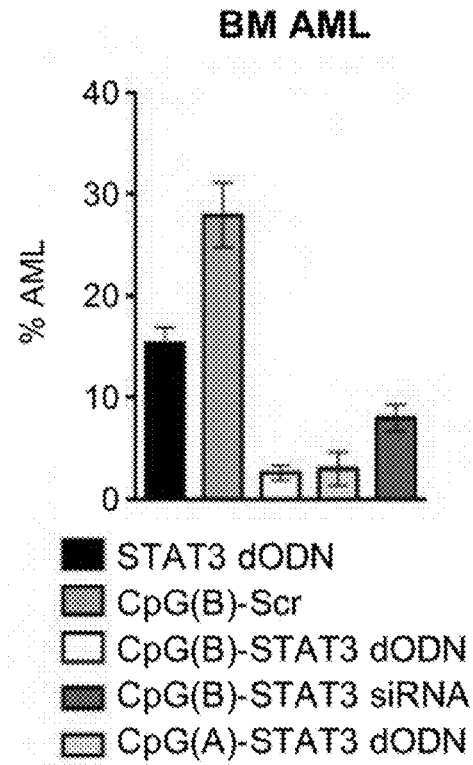

Intravenously Injected CpG-STAT3dODN Conjugates are more Effective than CpG-Stat3 siRNA Against Disseminated leukemia in vivo After 2-3 weeks from tumor challenge, with confirmed AML engraftment (>1%, ranging 1-5% of AML cells in blood), mice were injected iv. only 3 times every other day using 5 mg/kg of CpG(B)-Stat3 siRNA, CpG(A)-STAT3dODN, CpG(B)-STAT3dODN or CpG(B)-scrambled ODN conjugates and euthanized one day after the last treatment (FIGS. 10A-10C). Treatments using both types of CpG-STAT3 dODN were more effective than CpG-Stat3 siRNA in reducing percentages of AML cells in blood (FIG. 10A), lymph nodes (FIG. 10B) and bone marrow (FIG. 10C). Shown are combined results from 6 mice/group; means±SEM.

Example K

CpG-dODN Conjugates are Strongly Immunostimulatory Comparing to the Unconjugated Decoy STAT3

Figure 11:
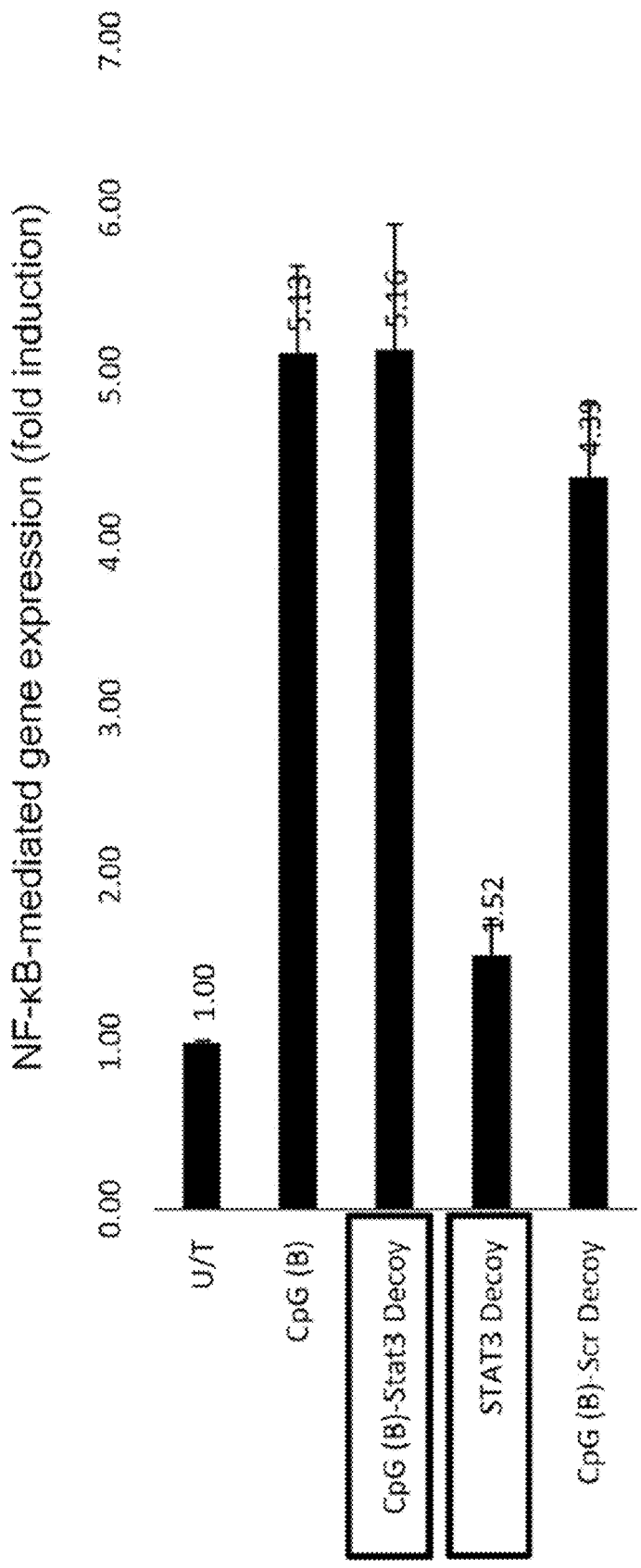
FIG. 11. CpG-dODN conjugates are strongly immunostimulatory comparing to the unconjugated decoy STAT3.

RAW-Blue cells with stable expression of the NF-κB-responsive promoter/SEAP reporter gene construct were incubated in the presence of 250 nM of indicated oligonucleotides or left untreated (FIG. 11). After 24 hrs the SEAP activity was assessed colorimetrically in cell culture supernatants. The results derived from triplicates were shown as means±SD (FIG. 11).

Example L

Figure 12:
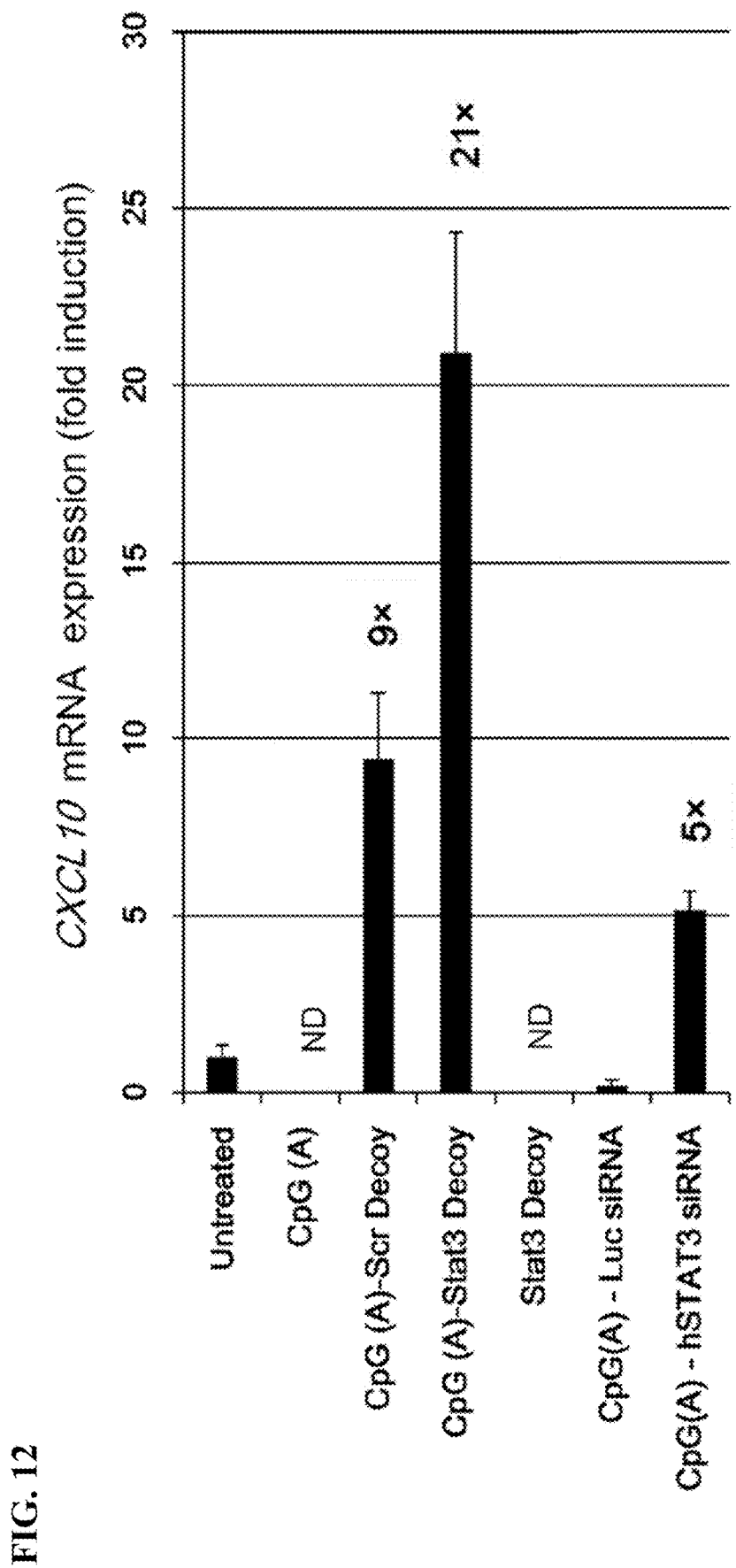
FIG. 12. CpG(A)-STAT3dODN induce potent immunostimulatory effects in human immune cells derived from late-stage prostate cancer patients.

CpG(A)-STAT3dODN Induce Potent Immunostimulatory Effects in Human Immune Cells Derived from Late-Stage Prostate Cancer Patients PBMCs isolated from prostate cancer patients were incubated in 10% autologous patients' plasma in the presence of the indicated oligonucleotides (125 nM each) (FIG. 12). After 36 h, cells were lysed and the expression of CXCL-10/IP-10 mRNA was assessed in total RNA samples using real-time qPCR (Roche). Results were normalized to TBP gene expression and recalculated as fold induction using the level in untreated PBMCs as a 1; ND—not detectable; means±SEM (n=3) (FIG. 12).

Example M

Figure 13:
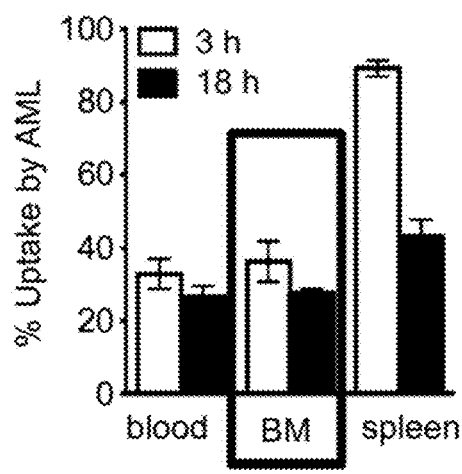
FIG. 13. CpG-STAT3dODN but not the unconjugated STAT3dODN is efficiently internalized by bone-marrow resident leukemia cells and tumor-associated myeloid cells.
Figure 13:
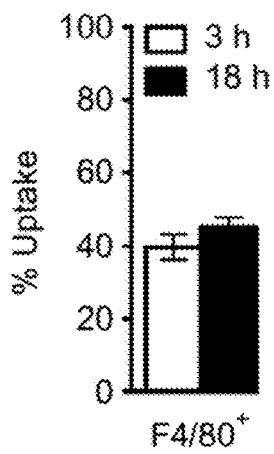
Figure 13:
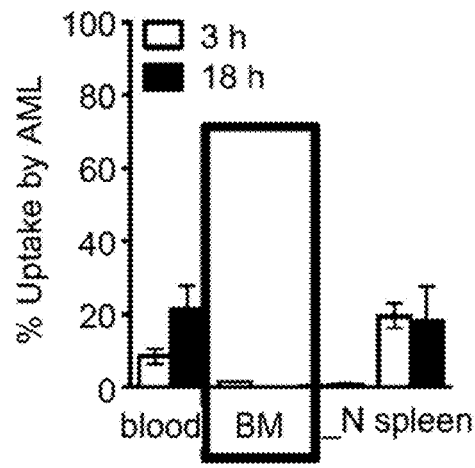
Figure 13:
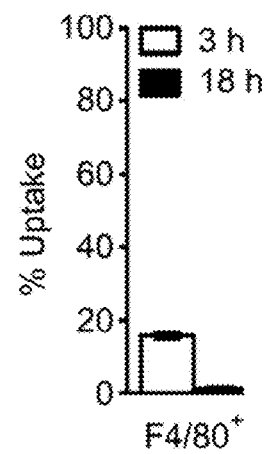

CpG-STAT3dODN but not the Unconjugated STAT3dODN is Efficiently Internalized by Bone-Marrow Resident leukemia Cells And Tumor-Associated Myeloid Cells CMM+ AML-bearing C57BL/6 mice (n=6) were injected with a single intravenous 5 mg/kg dose of Cy3-labeled CpGSTAT3dODN (FIG. 13 top row) or STAT3dODN alone (FIG. 13 bottom row). The biodistribution of fluorescently labeled oligonucleotides was assessed in the indicated organs at 3 or 18 hrs after injection using flow cytometry. The internalization by bone marrow-resident leukemia cells was indicated by rectangles (FIG. 13). Results are representative of two independent experiments.

Example N

Figure 14A:
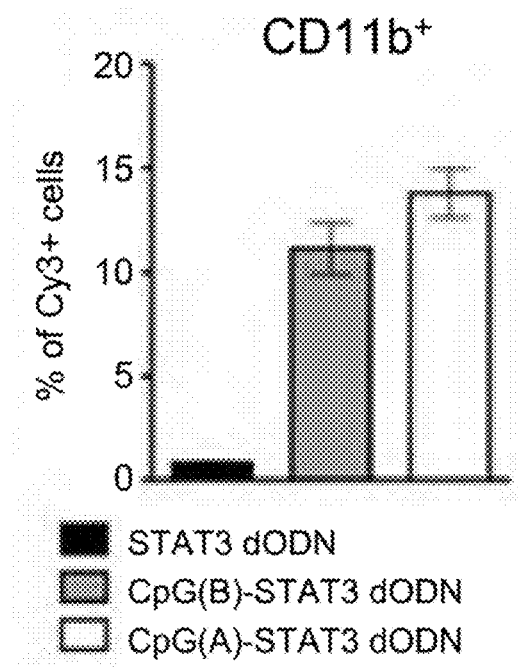
FIGS. 14A-14B. CpG-STAT3dODN but not the unconjugated STAT3dODN targets perivascular macrophages in the brain. Naïve C57BL/6 mice (n=4) were injected with a single intravenous 5 mg/kg dose of Cy3-labeled CpG(A)-STAT3dODN, CpG(B)-STAT3dODN or STAT3dODN alone as indicated (FIG. 14A-B). The uptake of fluorescently labeled oligonucleotides by total myeloid cells (FIG. 14A) and perivascular macrophages (FIG. 14B) was assessed using flow cytometry in brain tissues collected at 18 hrs after injection.
Figure 14B:
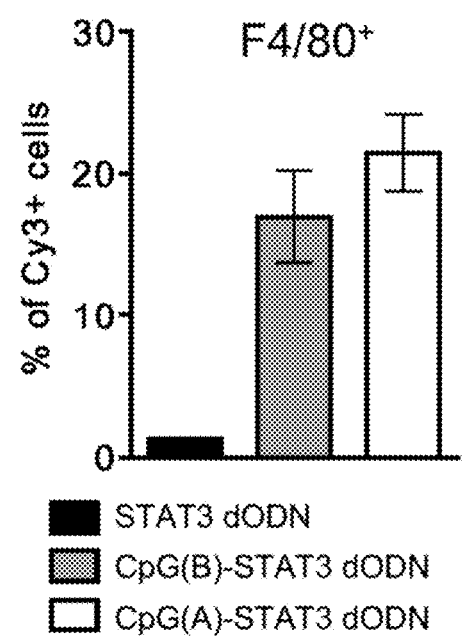

CpG-STAT3dODN but not the Unconjugated STAT3dODN Targets Perivascular Macrophages in the Brain Naïve C57BL/6 mice (n=4) were injected with a single intravenous 5 mg/kg dose of Cy3-labeled CpG(A)-STAT3dODN, CpG(B)-STAT3dODN or STAT3dODN alone as indicated (FIGS. 14A-14B). The uptake of fluorescently labeled oligonucleotides by total myeloid cells (FIG. 14A) and perivascular macrophages (FIG. 14B) was assessed using flow cytometry in brain tissues collected at 18 hrs after injection.

CpG(A)-STAT3dODN is not cytotoxic for normal human immune cells

Figure 15A:
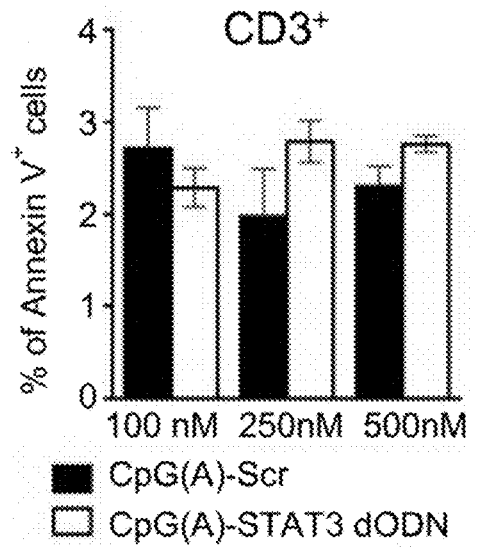
FIGS. 15A-15C. CpG(A)-STAT3dODN is not cytotoxic for normal human immune cells. PBMCs isolated from healthy subjects were incubated in the presence of various concentrations of CpG(A)-STAT3dODN or control CpG (A)-scrambled ODN (FIG. 15A-C). Cells were collected after 72 h to analyze percentages of Annexin V-positive apoptotic cells among $CD3^+$ T cells (FIG. 15A), $CD19^+$ B cells (FIG. 15B) and $CD303^+$ pDC (FIG. 15C) using flow cytometry. Shown are means±SEM (n=3).
Figure 15B:
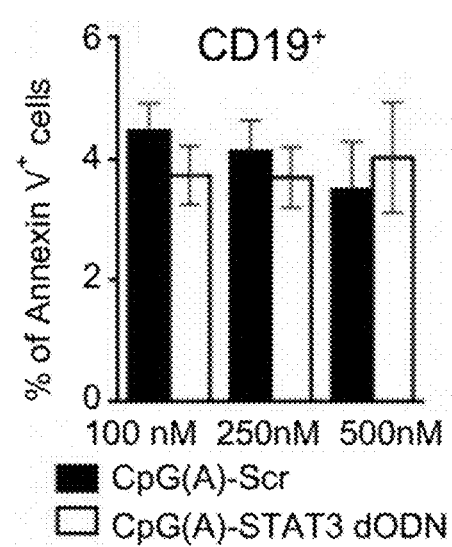
Figure 15C:
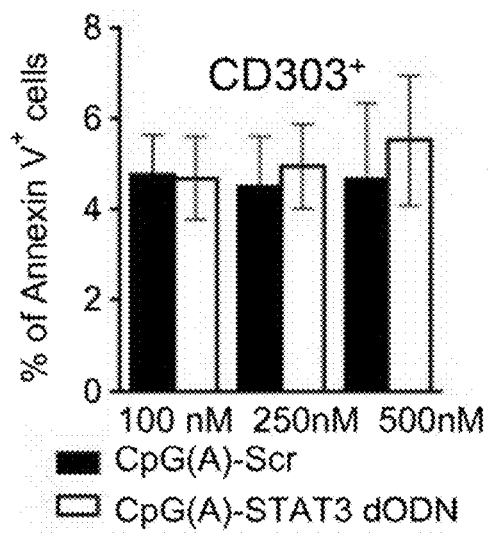
Figure 16A:
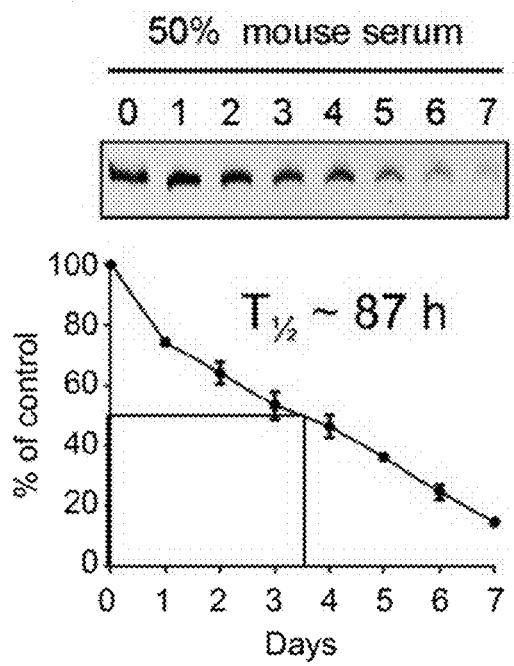
FIGS. 16A-16B. Half-life of chemically modified CpG-STAT3 decoy oligodeoxynucleotides in mouse and human sera.
Figure 16B:
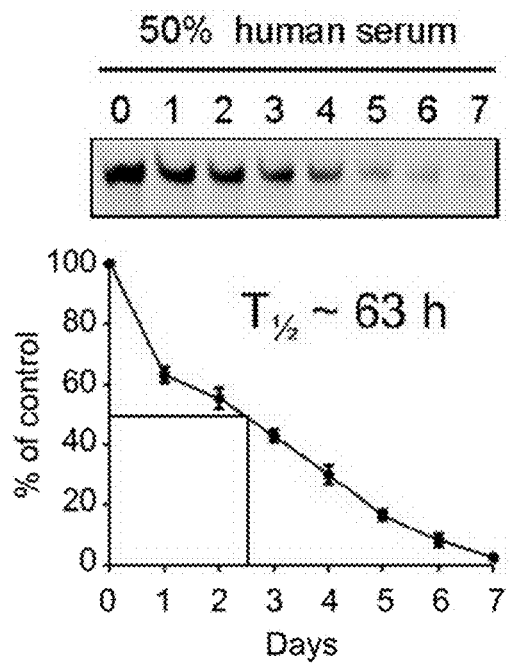
Figure 17A:
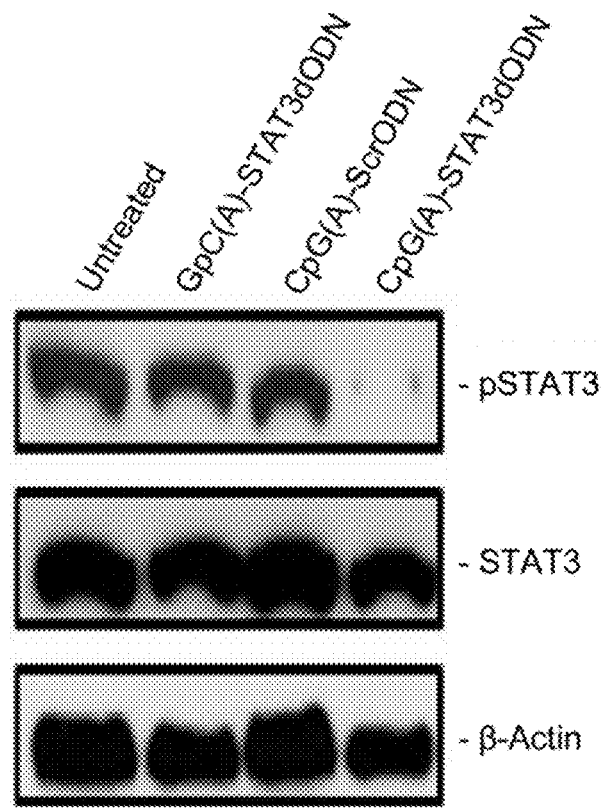
FIGS. 17A-17B. CpG-STAT3dODN inhibits STAT3 activity in dose-dependent manner.
Figure 17B:
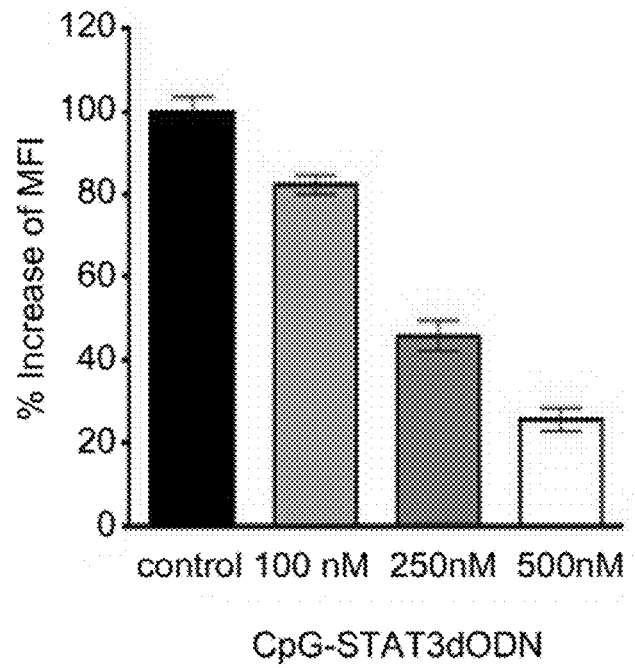
Figure 18A:
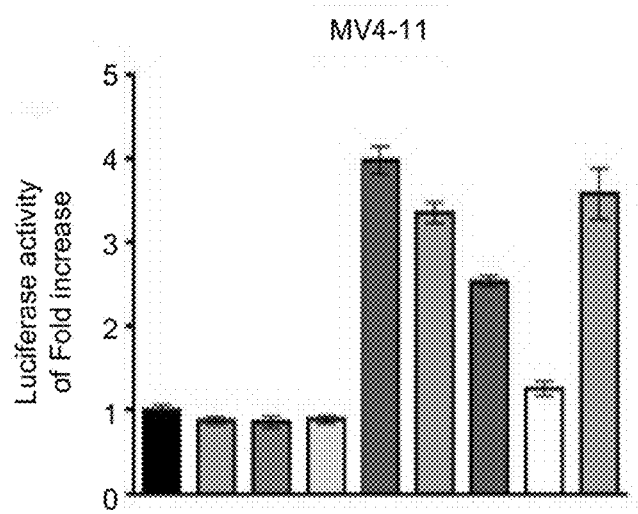
FIGS. 18A-18B. CpG-STAT3dODN reduces transcriptional STAT3 activity in dose-dependent manner.
Figure 18B:
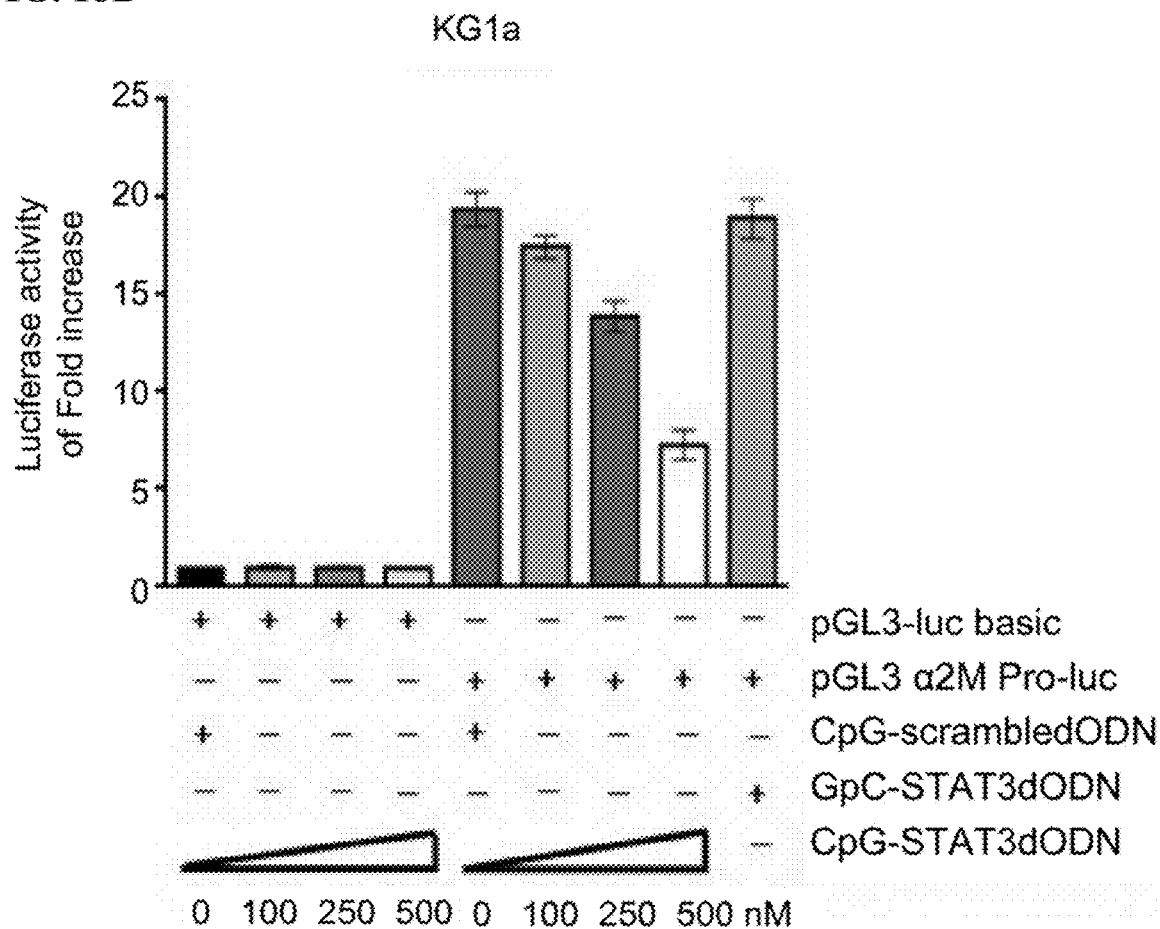
Figure 19:
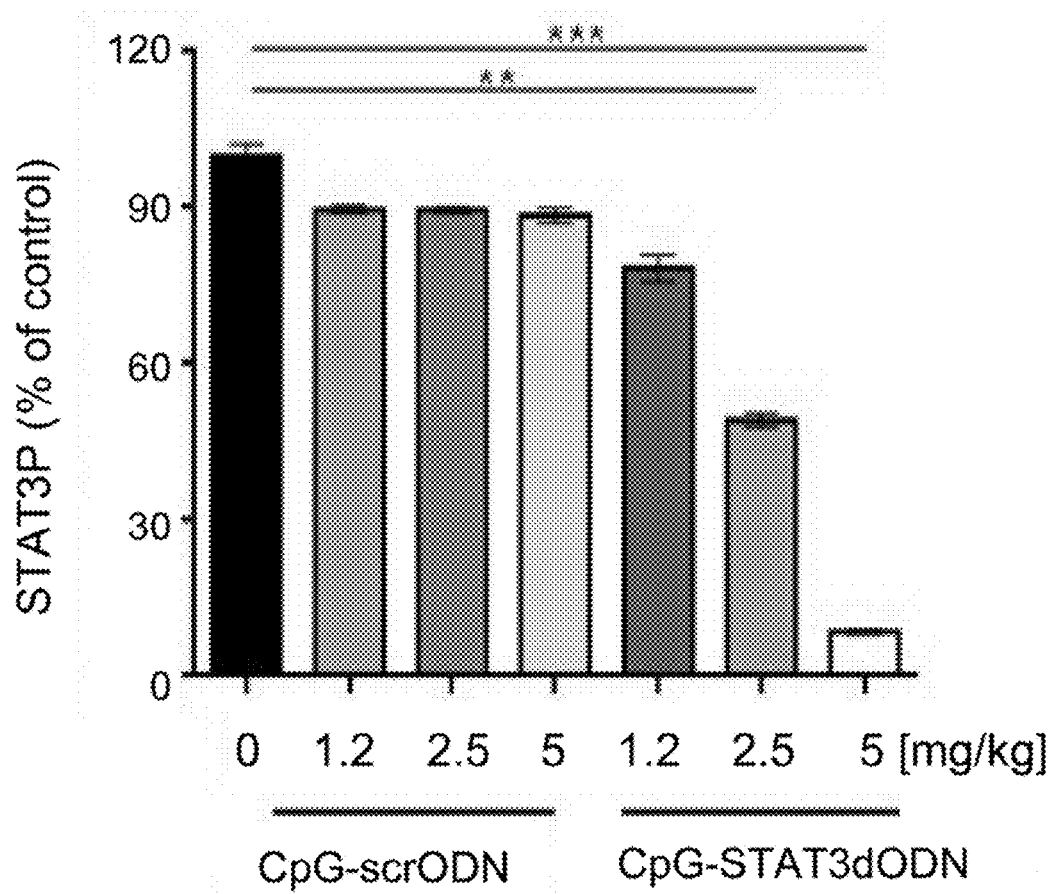
FIG. 19. Systemic administration of CpG-STAT3dODN reduces STAT3 activity in target TLR9-positive leukemia cells in dose-dependent manner. NSG mice were injected i.v. using MV4-11-luc AML cells. After leukemia was established in various organs as confirmed by bioluminescent imaging, mice were injected intravenously using various doses of CpGSTAT3dODN or control CpG-scrODN. Mice were euthanized a day later, spleens were harvested to prepare single cell suspension and the level of STAT3 activity was assessed using intracellular staining with pSTAT3-specific antibodies and flow cytometry; means±SEM (n=4).
Figure 20A:
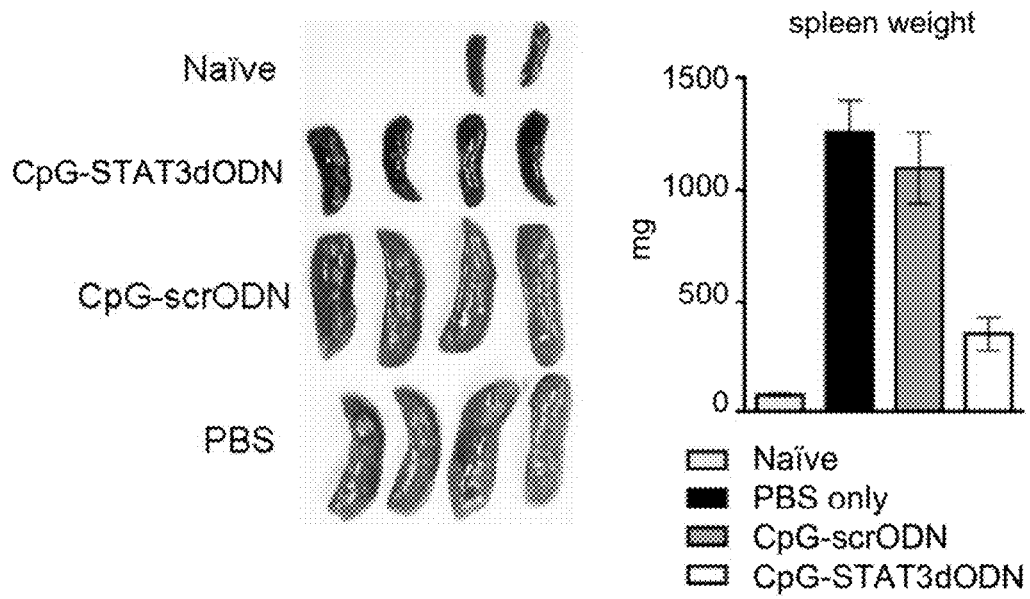
FIGS. 20A-20D. Systemic administration of CpG-STAT3dODN inhibits STAT3 signaling and induces AML regression in mice. C57BL/6 mice were injected i.v. using Cbfb-MYH11 AML cells. After leukemia was established (1-5% of circulating AML cells), mice were injected 6 times every other day i.v. using 5 mg/kg of CpG-STAT3dODN or control CpG-scrODN.
Figure 20B:
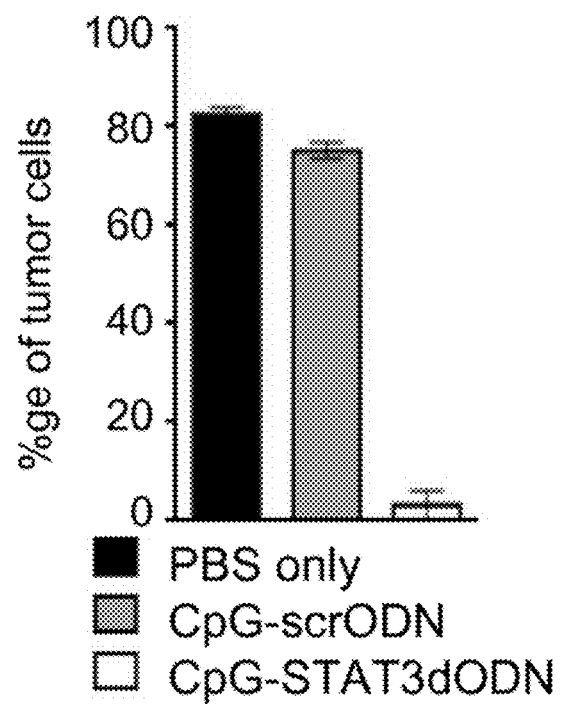
Figure 20C:
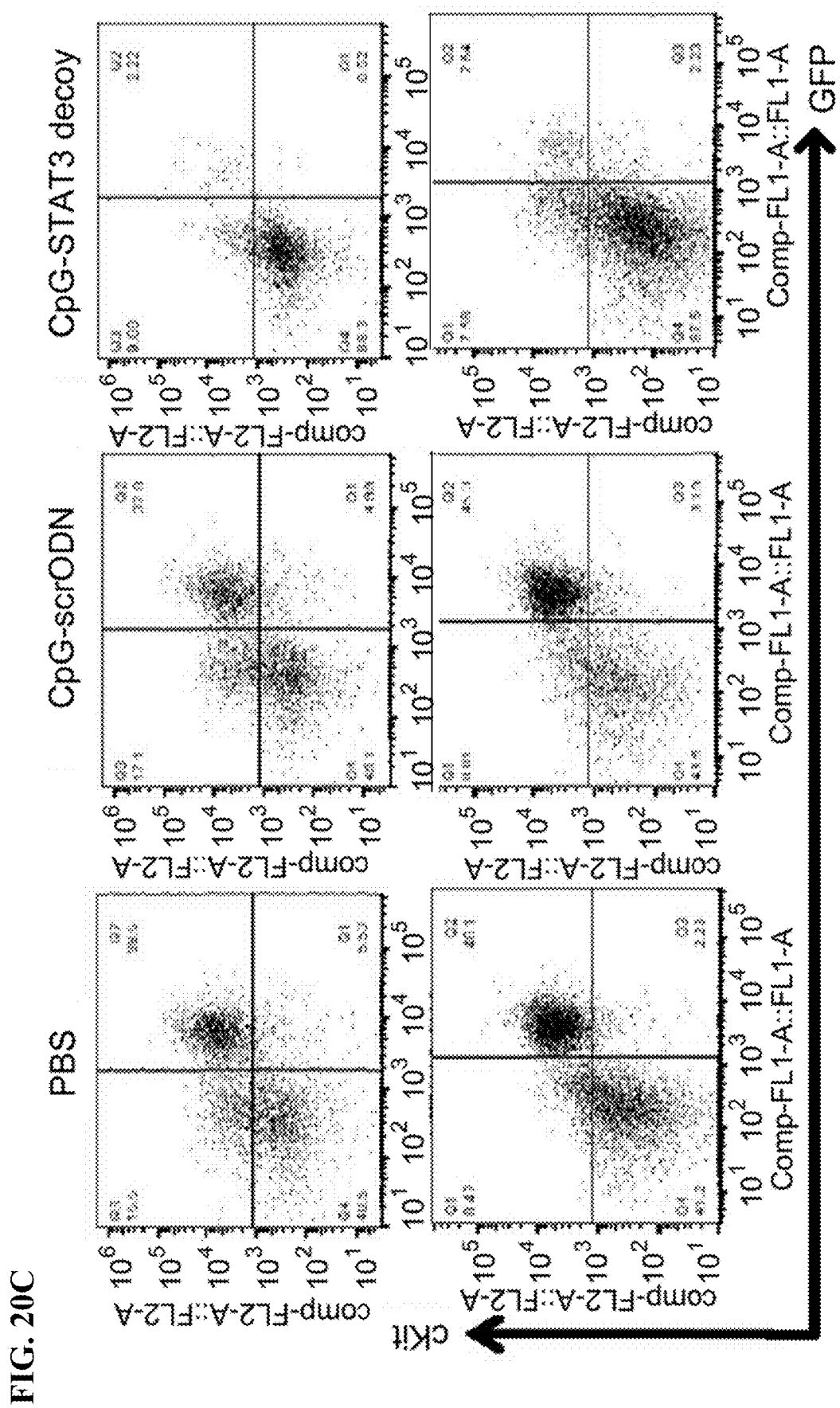
Figure 20D:
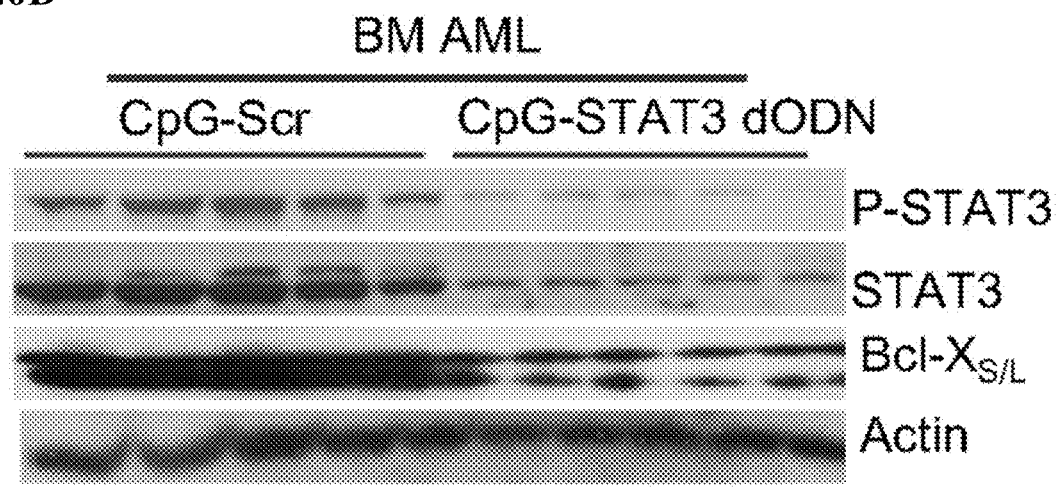
Figure 21C:
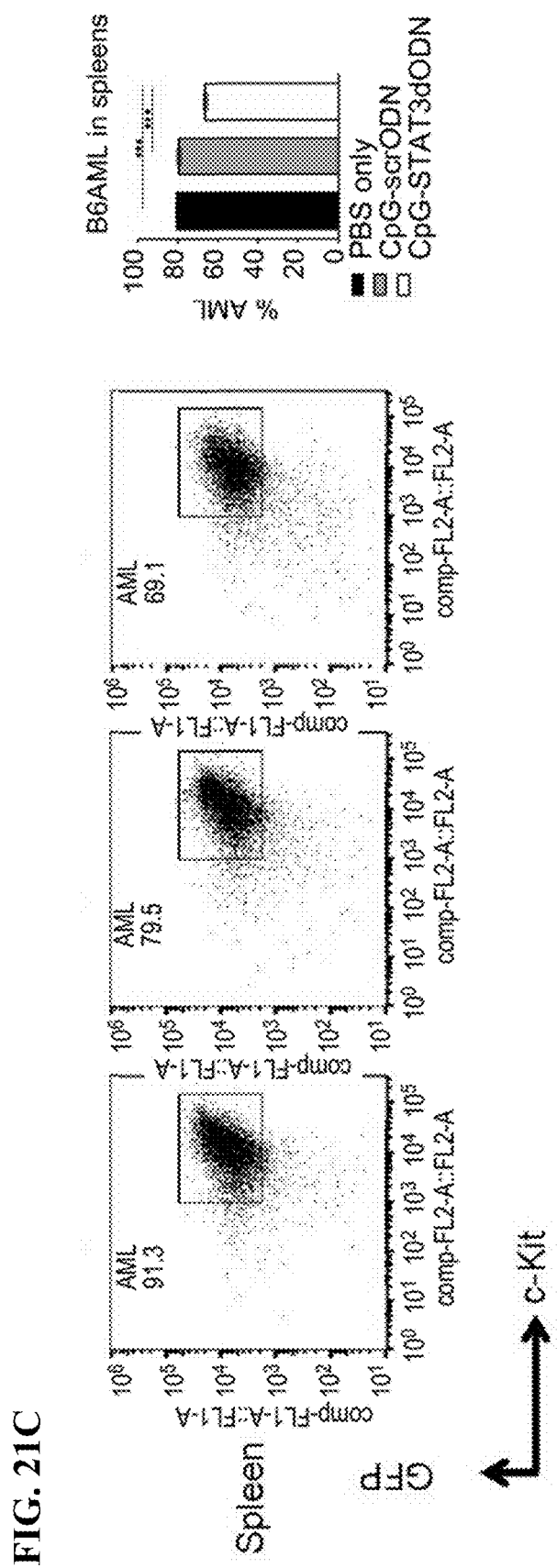
Figure 22A:
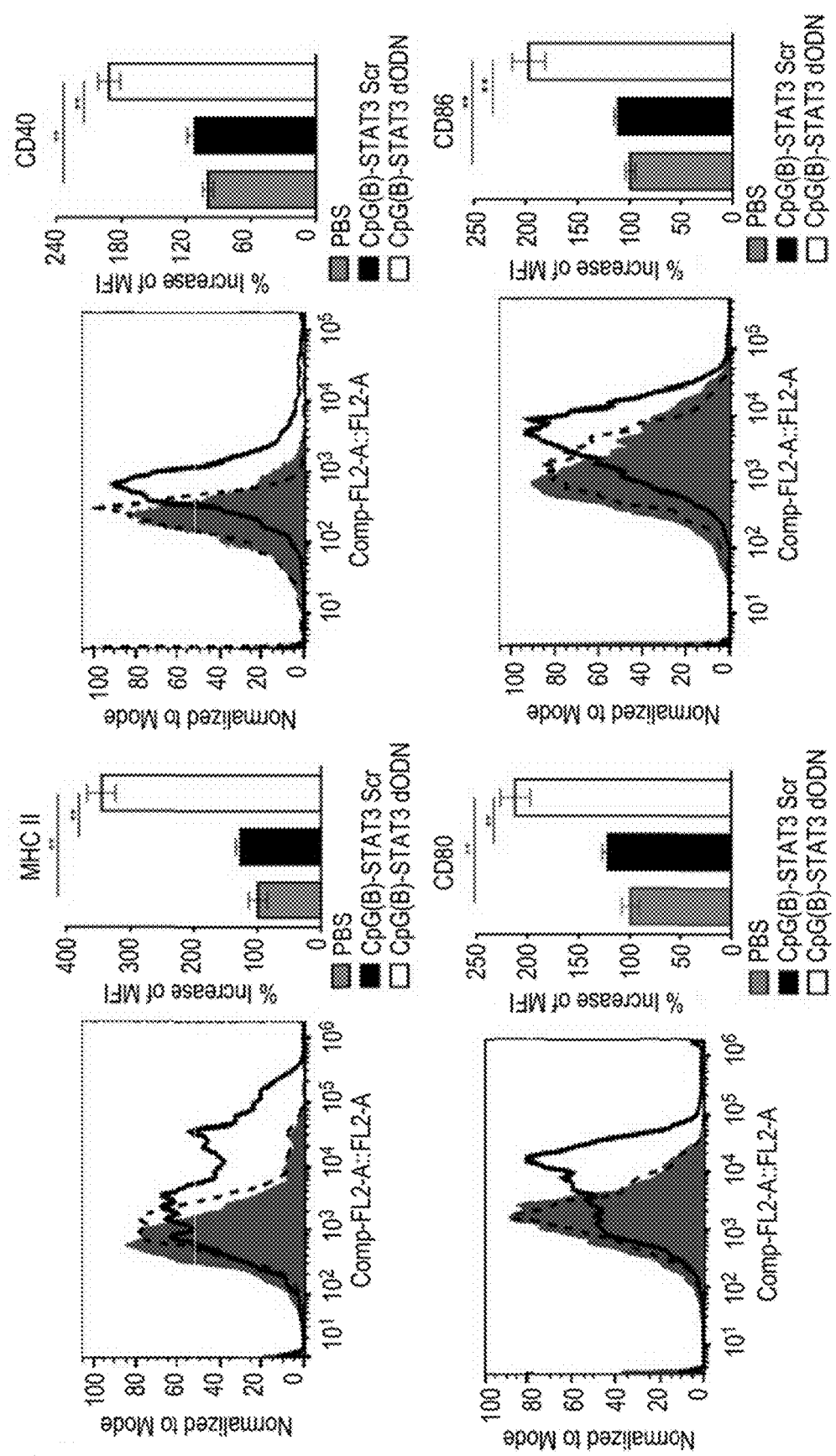
FIGS. 22A-22B. CpG-STAT3dODN treatment triggers immune activation of both dendritic cells (DC) and AML cells in vivo. C57BL/6 mice bearing disseminated Cbfb-MYH11 AML were treated as in FIG. 20A-D. The level of immune activation was assessed in both splenic CD11c+ DCs (FIG. 22A) and AML cells (FIG. 22B) detecting surface expression of MHC class II and costimulatory molecules such as CD40, CD80 and CD86 using flow cytometry. Shown are results from two independent experiments; means±SEM (n=5).
Figure 22B:
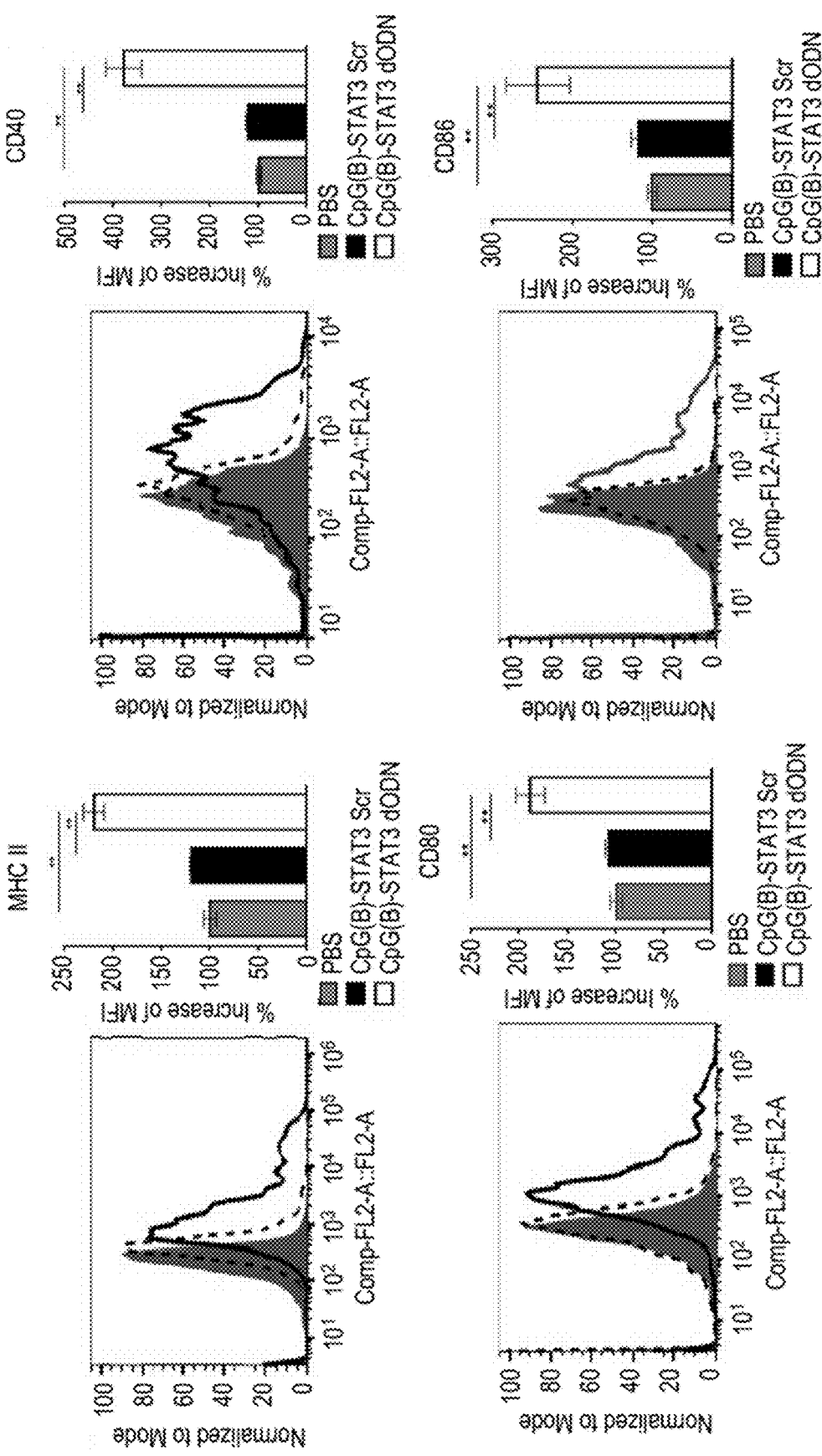
Figure 23:
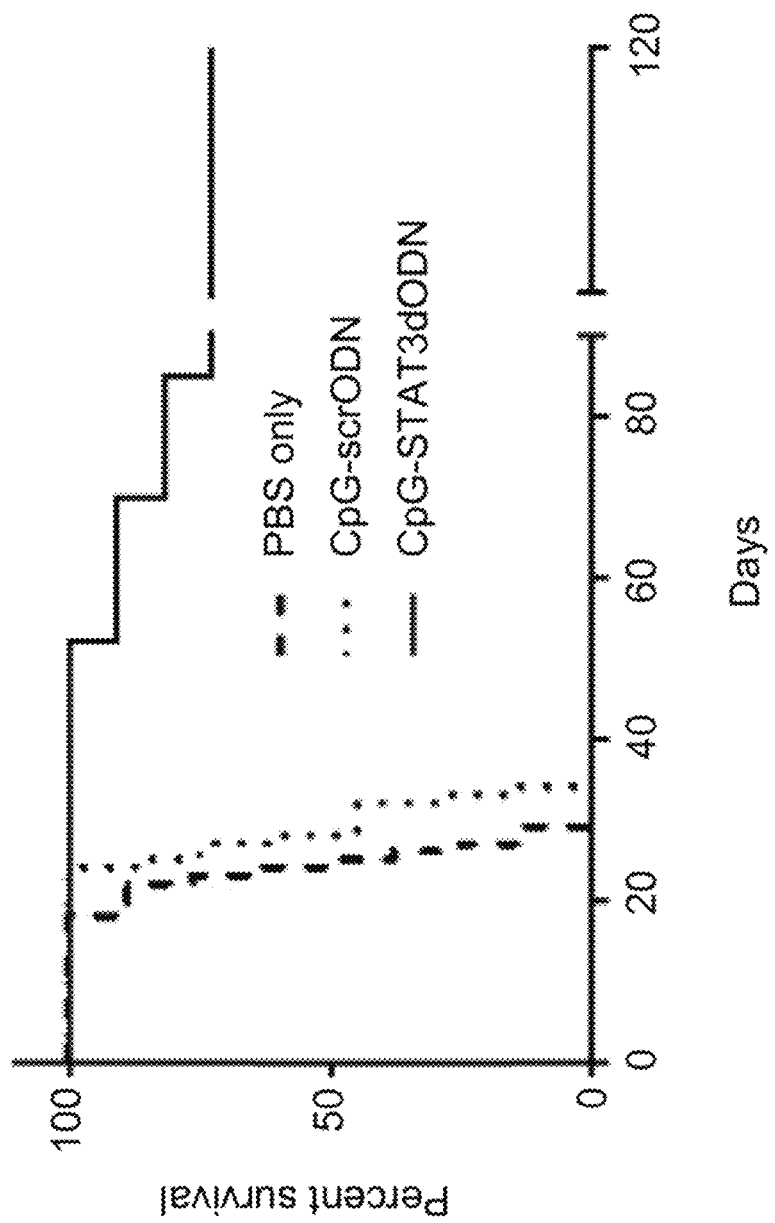
FIG. 23. In vivo treatment using CpG-STAT3dODN reduces leukemia-initiating potential and promotes long-term survival. C57BL/6 mice were injected i.v. using the same number of Cbfb-MYH11 AML cells isolated from donor mice treated using CpG-STAT3dODN, control CpG-scrODN or PBS treated (as in FIGS. 20A-20D). The survival of recipient mice was monitored for 120 days as indicated. Shown are means±SEM (n=6).
Figure 24A:
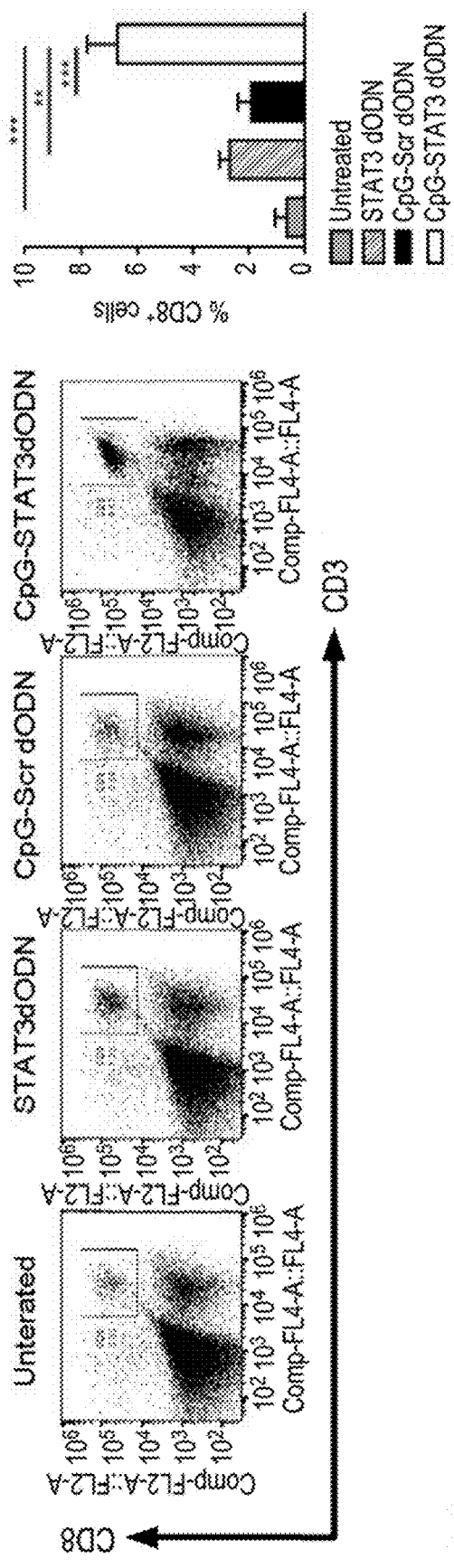
FIGS. 24A-24B. Systemic administration of CpG-STAT3dODN shift the balance between CD8 and regulatory T cells. C57BL/6 mice bearing disseminated Cbfb-MYH11 AML were treated as in FIGS. 20A-20D. The percentages of CD8+ effector T cells (FIG. 24A) and CD4+/FoxP3+regulatory T cells (FIG. 24B) were assessed using flow cytometry; left panels—representative dot plot data; right panel—data summary. Shown are results from two independent experiments; means±SEM (n=5).
Figure 24B:
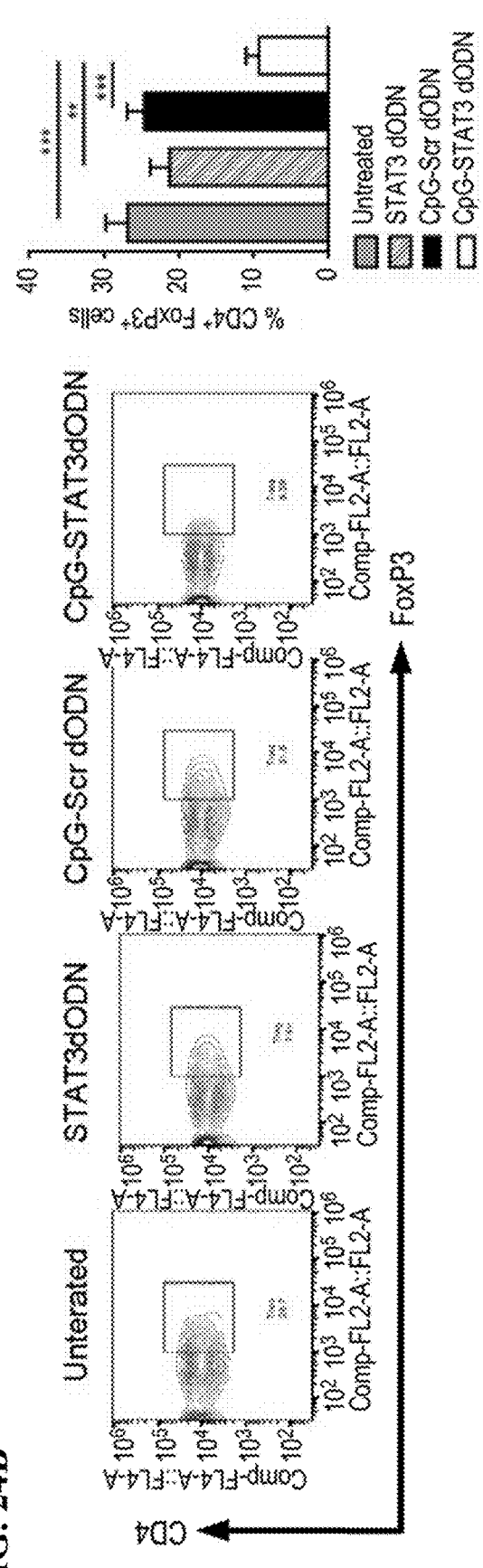
Figure 25A:
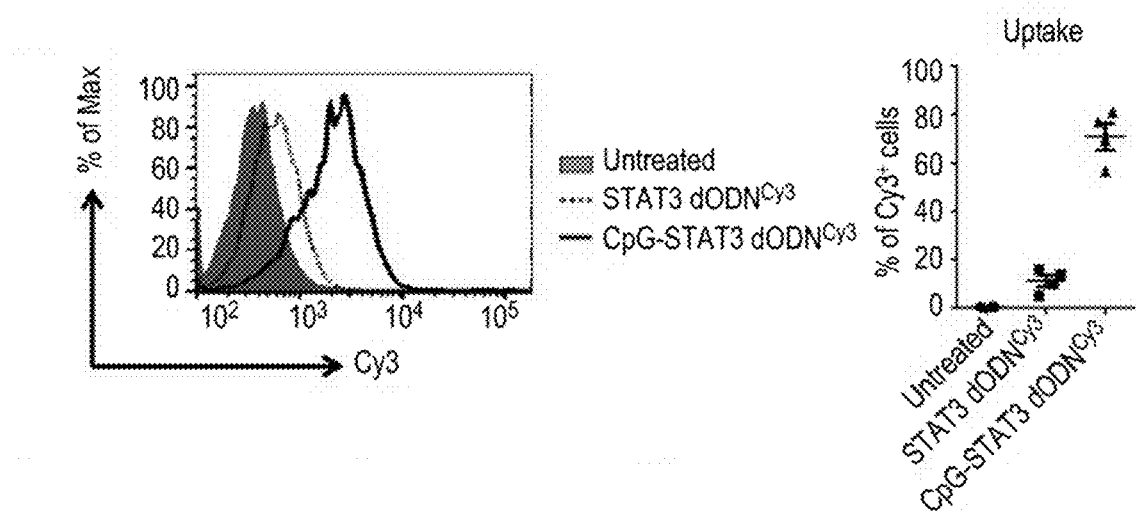
FIGS. 25A-25F. CpG-STAT3dODN induces immunogenic effects on human primary AML cells from patients with recurrent leukemia.
Figure 25B:
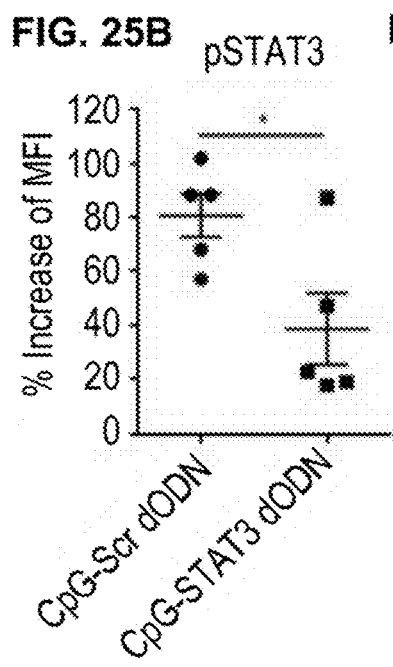
Figure 25C:
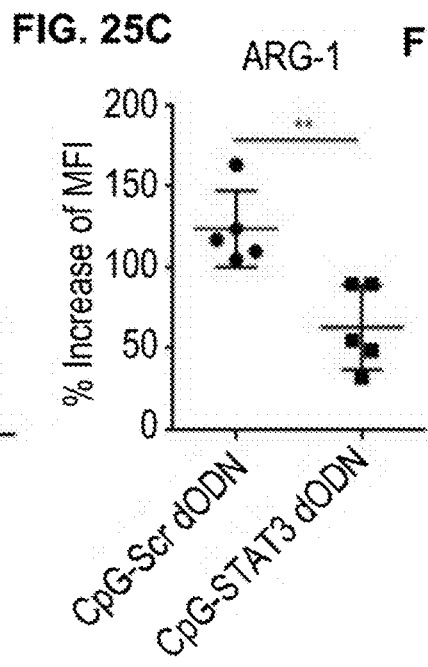
Figure 25D:
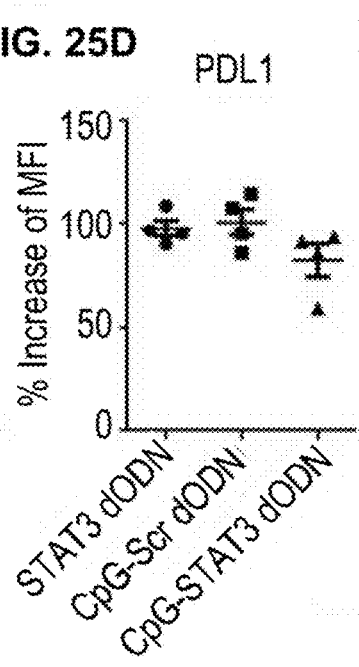
Figure 25E:
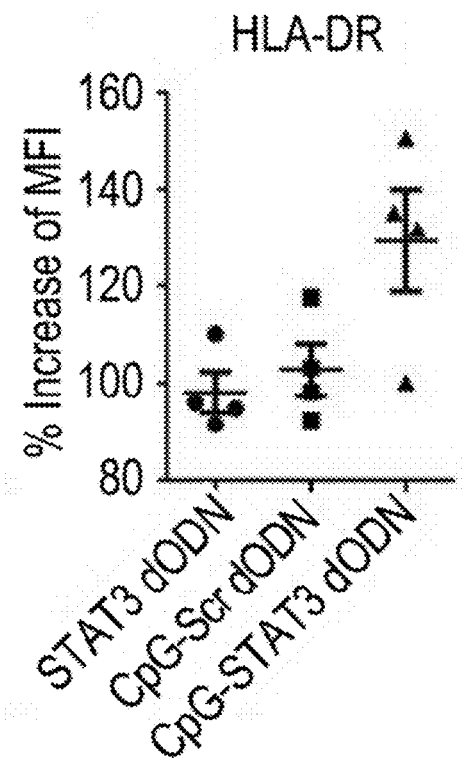
Figure 25F:
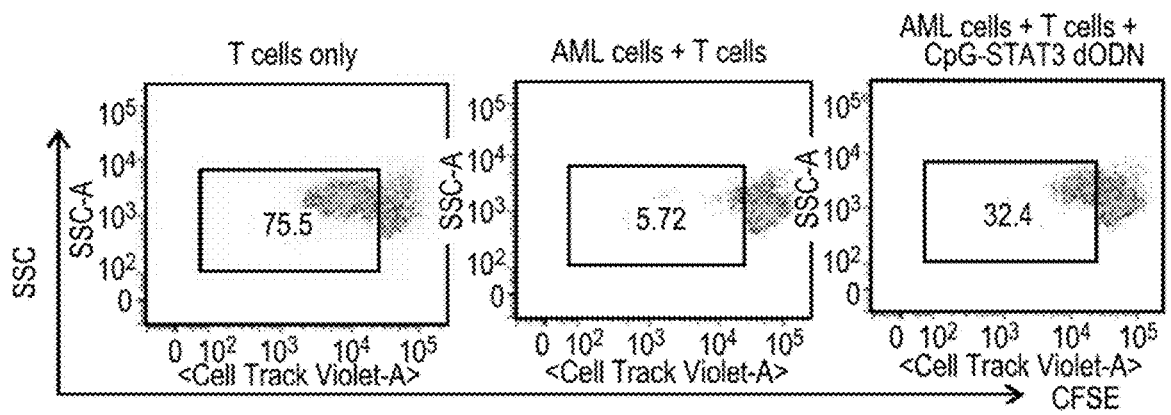
Figure 26A:
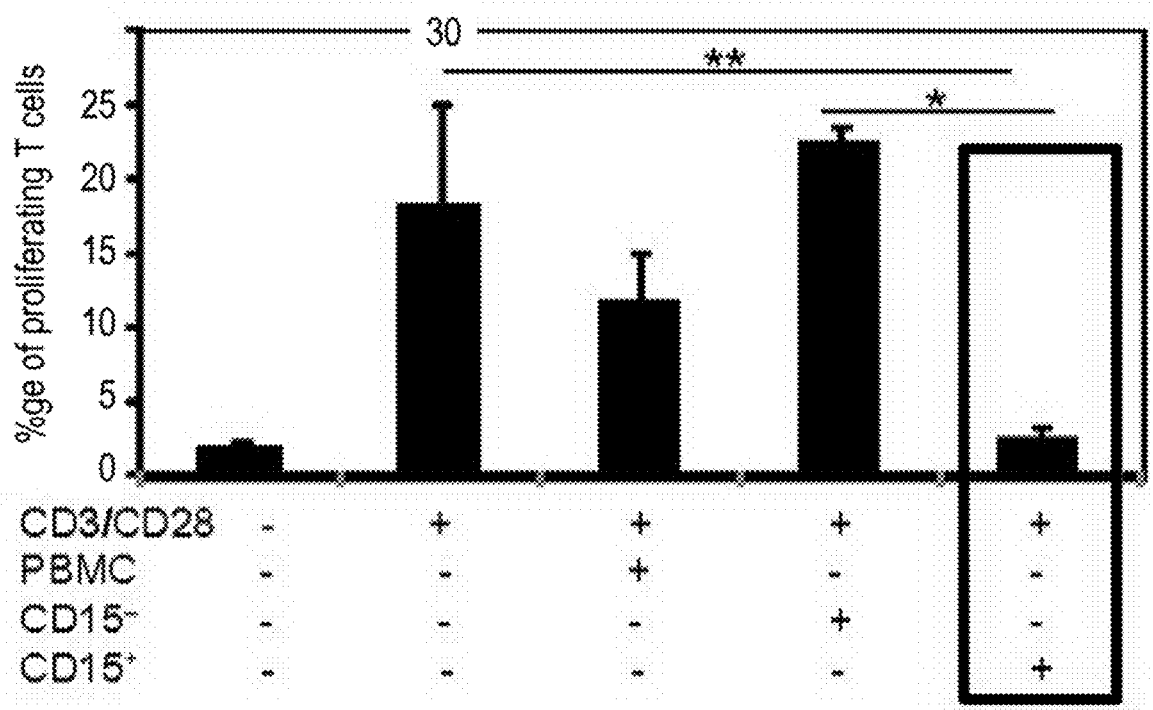
FIGS. 26A-26C. CpG-STAT3dODN alleviates immunosuppressive effects of myeloid-derived suppressor cells (MDSC) in vitro.
Figure 26B:
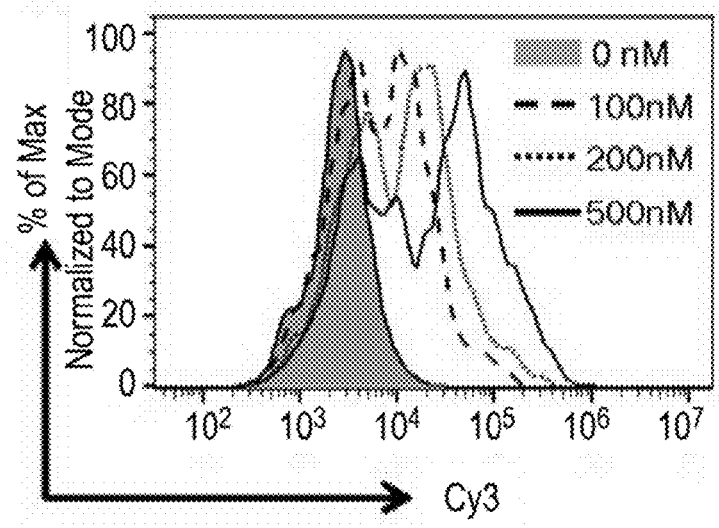
Figure 26C:
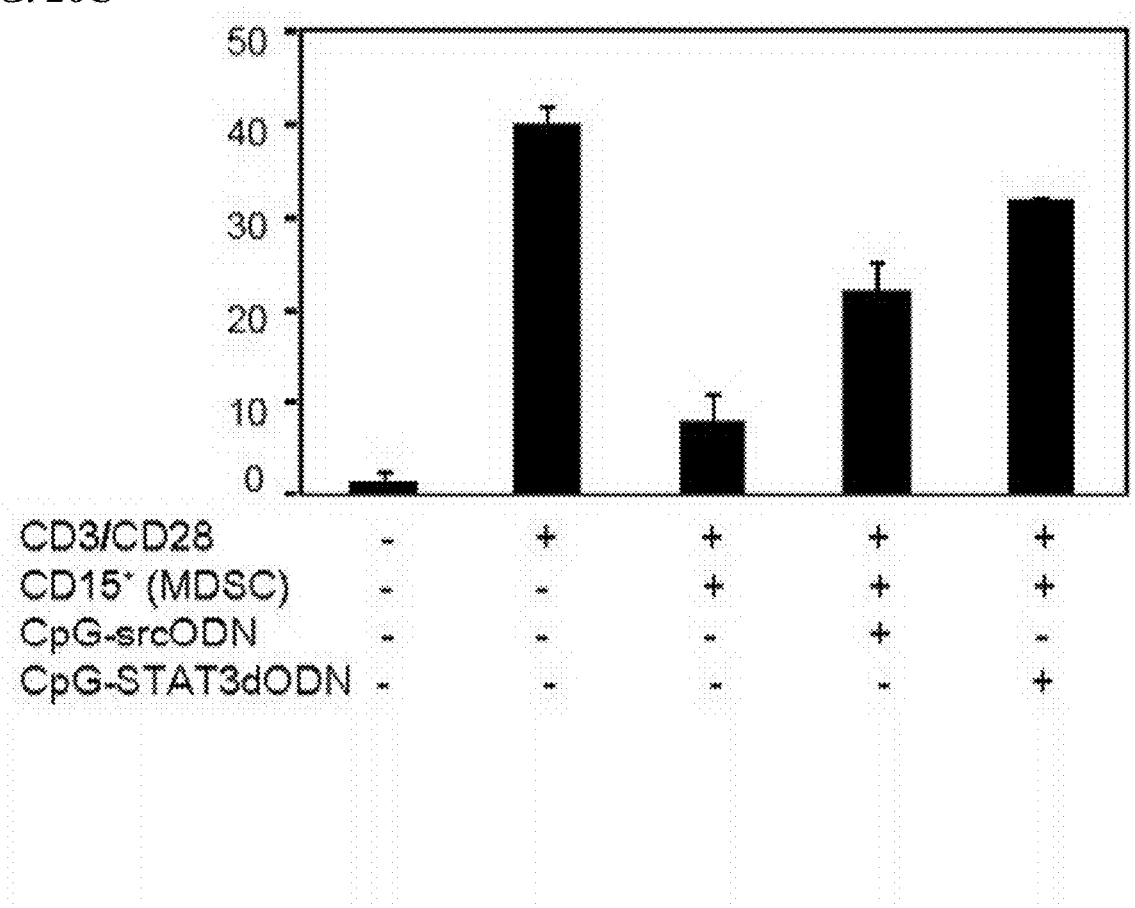
Figure 27:
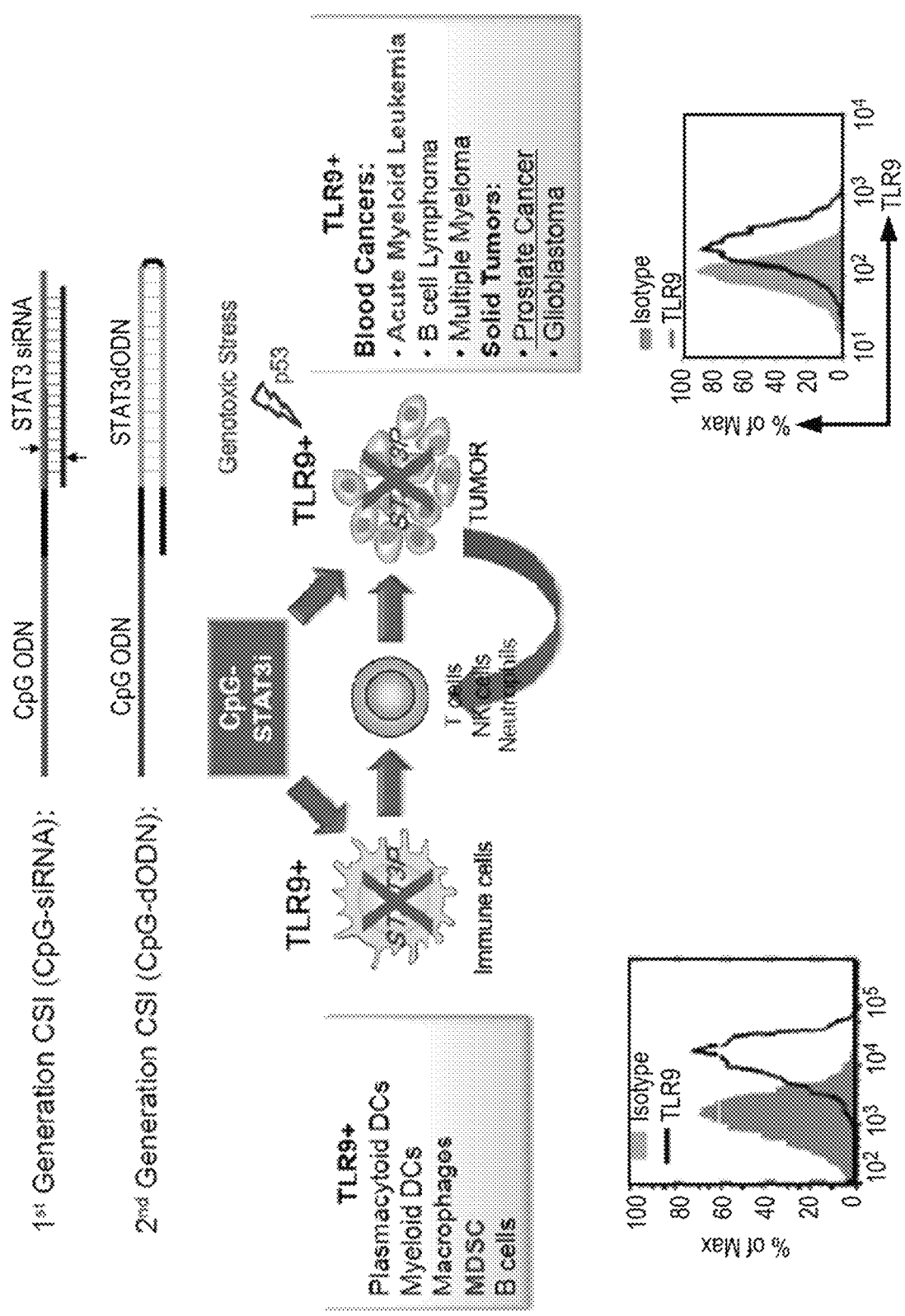
FIG. 27. CpG-STAT3dODN: DNA-based STAT3 inhibitor.
Figure 28A:
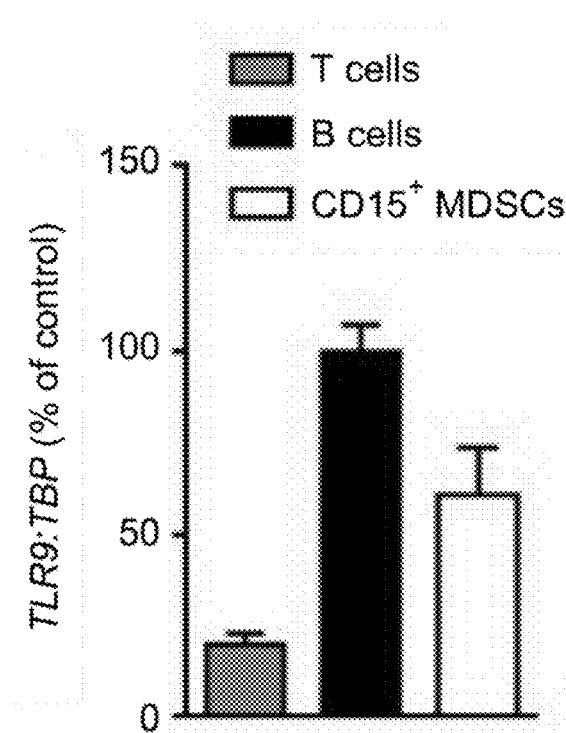
FIGS. 28A-28B. TLR9 expression in human and mouse myeloid cells.
Figure 28B:
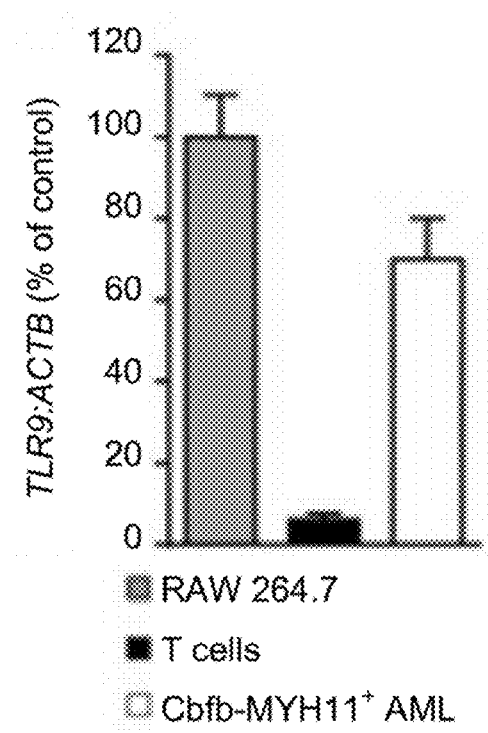
Figure 29:
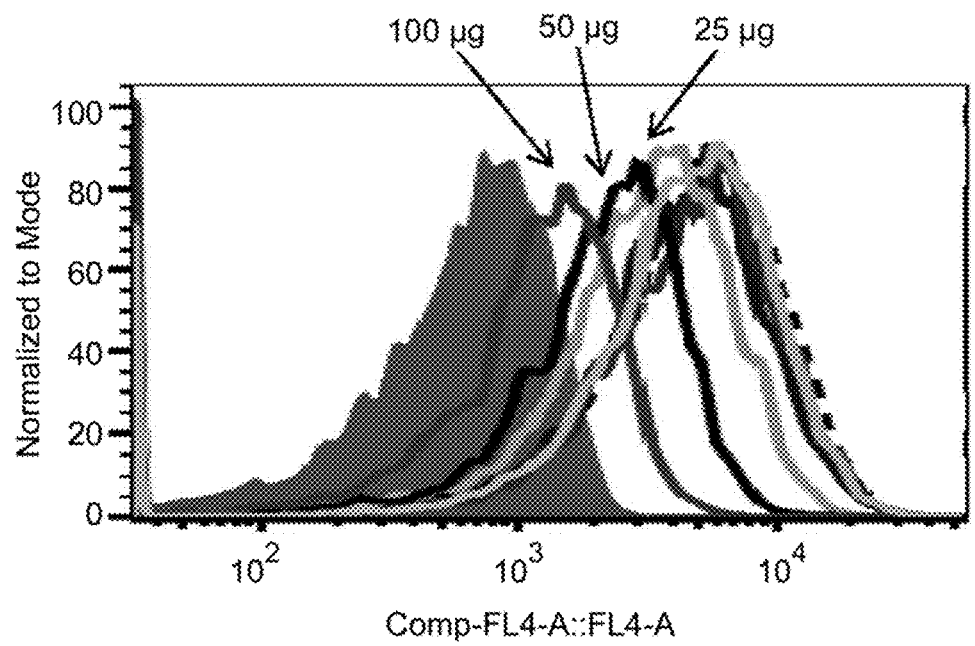
FIG. 29. Systemic administration of CpG-STAT3dODN reduces STAT3 activity in target TLR9-positive leukemia cells in dose-dependent manner. NSG mice were injected i.v. using MV4-11-luc AML cells. After leukemia was established in various organs as confirmed by bioluminescent imaging, mice were injected intravenously using various doses of CpGSTAT3dODN or control CpG-scrODN. Animals were euthanized a day later, spleens were harvested to prepare single cell suspension and the level of STAT3 activity was assessed using intracellular staining with pSTAT3-specific antibodies and flow cytometry; means±SEM (n=4).
Figure 30:
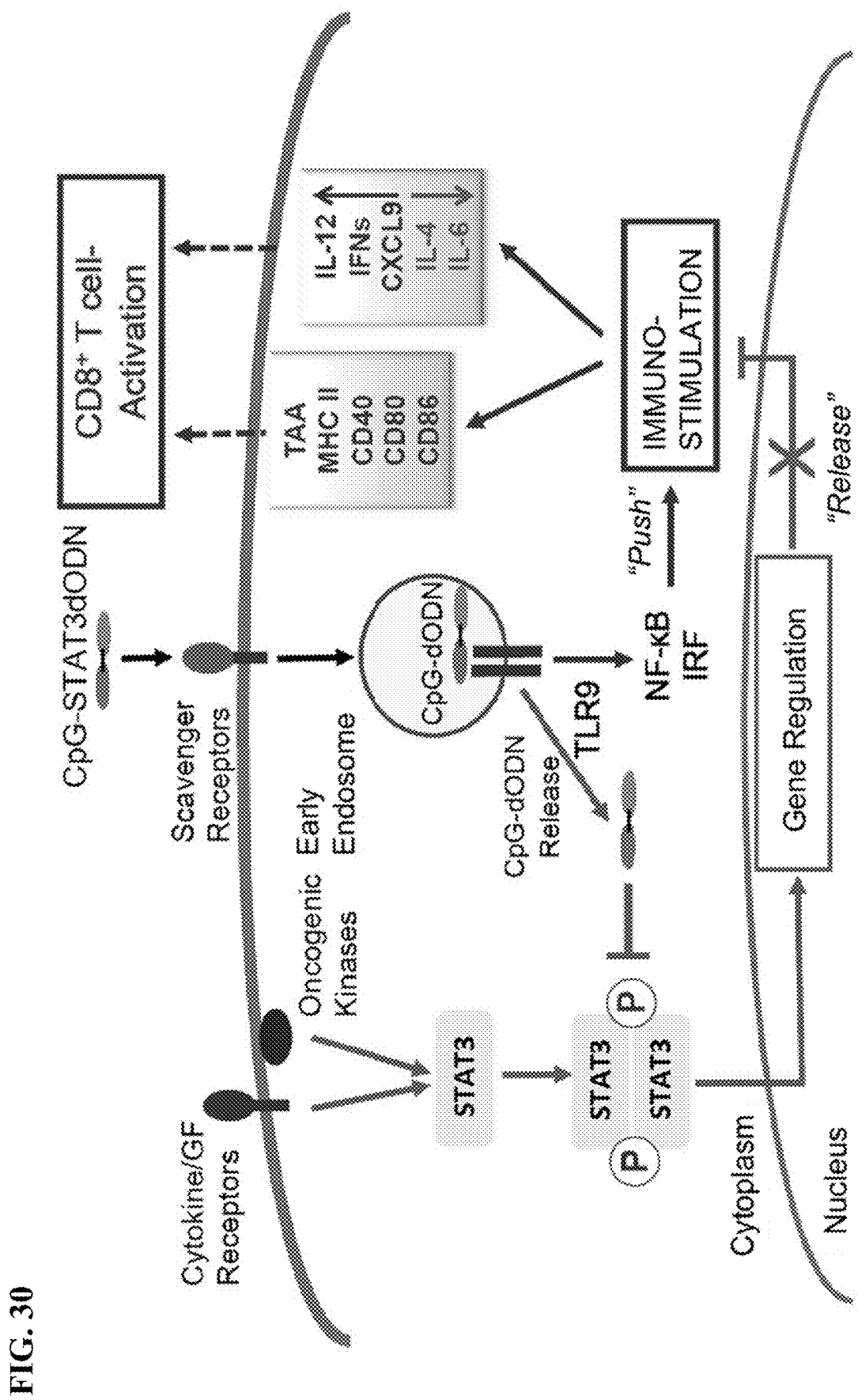
FIG. 30. "Push & Release" Strategy for leukemia immunotherapy. CpG-STAT3dODN induces immunogenic effects in normal and malignant myeloid cells as a result of coordinated immune stimulation through TLR9 triggering ("push" signal) and the elimination of negative regulation by STAT3 ("release" signal).

PBMCs isolated from healthy subjects were incubated in the presence of various concentrations of CpG(A)-STAT3dODN or control CpG(A)-scrambled ODN (FIGS. 15A-15C). Cells were collected after 72 h to analyze percentages of Annexin V-positive apoptotic cells among CD3+ T cells (FIG. 15A), CD19+ B cells (FIG. 15B) and CD303+ pDC (FIG. 15C) using flow cytometry. Shown are means±SEM (n=3)

Experimental Materials and Methods

Cells and Mice. Cbfb$^{+/56M}$/Mx-Cre$^+$ mice (Kuo et al. Cancer Cell 2006) were backcrossed to wild-type C57BL/6 mice for >10 generations to generate the syngeneic AML model. Two weeks after poly(I:C)-induced (Invivogen) expression of CBFβ-SMMHC, bone marrow cells from Cbfb$^{+/56M}$/MX-Cre$^+$ mice were transduced with retroviral MIG-Mpl vector encoding thrombopoietin receptor and GFP genes to generate transplantable Cbfb-MYH11/Mpl mouse AML (Landrette et al. Leukemia. 2011). Mouse RAW264.7 macrophages and human PC3, DU145 prostate cancer cells were purchased from ATCC. The reporter RAW-Blue cells were obtained from Imgenex and handled as suggested by the manufacturer. Human KG1a, MV4-11 leukemia and Raji, REC1 lymphoma cell lines were obtained. Mousec B16-F10 melanoma, TRAMP-C2 (TC2) prostate cancer, MB49 bladder cancer and K1739-M2 melanoma cells were kindly provided. Healthy PBMCs were isolated from discarded blood samples from anonymous donors provided by the Blood Donor Center at City of Hope.

Reagents. The CpG-siRNAs were synthesized in the DNA/RNA Synthesis Core (COH) by linking CpG(B)-ODN (CpG1668), CpG(A) (D19) or GpC(A) to STAT3 decoy or scrambled ODN sequences similarly as previously described (Kortylewski et al. Nat. Biotech. 2009) using 4-5 units of C3 carbon chain, $(CH_2)_3$ (Glen Research, Virginia). The resulting ODN conjugates are shown below, x indicates a single C3 unit bonded to phosphate groups at both ends, except at the 5' end and 3' end where the last 3' x is —C[6]—NH$_2$ following the final phosphate group and a 5' terminal x has an OH group at the terminus. A 5' nucleotide has a terminal 5' OH group. Asterisks indicate phosphothioation sites):

```
CpG(A)-STAT3dODN
                                            (SEQ ID NO: 6)
5' G*G*TGCATCGATGCAGG*G*G*G*G-xxxxx-C*A*T*TTCCCGTA
AATC-xxxx-GATTTACGGGAA*A*T*G-xxxxx 3'

GpC(A)-STAT3dODN
                                            (SEQ ID NO: 7)
5' G*G*TGCATGCATGCAGG*G*G*G*G-xxxxx-C*A*T*TTCCCGTA
AATC-xxxx-GATTTACGGGAA*A*T*G-xxxxx 3'

CpG(A)-scrambled ODN
                                            (SEQ ID NO: 8)
5' G*G*TGCATCGATGCAGG*G*G*G*G-xxxxx-A*C*T*CTTGCCAA
TTAC-xxxx-GTAATTGGCAAG*A*G*T-xxxxx 3'

CpG(B)-STAT3dODN
                                            (SEQ ID NO: 9)
5' T*C*C*A*T*G*A*C*G*T*T*C*C*T*G*A*T*G*C*T-xxxxx-
C*A*T*TTCCCGTAAATC-xxxx-GATTTACGGGAA*A*T*G-xxxxx
3'

CpG(B)-mutSTAT3dODN
                                            (SEQ ID NO: 10)
5' T*C*C*A*T*G*A*C*G*T*T*C*C*T*G*A*T*G*C*T-xxxxx-
C*A*T*TTCCCTAAATC-xxxx-GATTTAAGGGAA*A*T*G-xxxxx
3'

CpG(B)-scrambled ODN
                                            (SEQ ID NO: 11)
5' T*C*C*A*T*G*A*C*G*T*T*C*C*T*G*A*T*G*C*T-xxxxx-
A*C*T*CTTGCCAATTAC-xxxx-GTAATTGGCAAG*A*G*T-xxxxx
3'

STAT3dODN alone
                                            (SEQ ID NO: 12)
5' xxxxx-C*A*T*TTCCCGTAAATC-xxxx-GATTTACGGGAA*A*T*
G-xxxxx 3'
```

For uptake studies, various ODN were labeled on the 3' end (via linker) using Alexa 488 or Cy3.

In vivo experiments. NOD/SCID/IL-2RγKO (NSG) and C57BL/6 mice (6-8 weeks old) were from the NCI (Frederick, Md.) or from the Jackson Laboratory, respectively. TLR9KO mice were originally from provided. Animal care/procedures were performed in accordance with established institutional guidance and approved protocols from the IACUC (COH). NSG or C57BL/6 mice were injected into lateral tail vein with $0.5 \times 10^6$ MV4-11luc or $1 \times 10^6$ of Cbfb-MYH11/Mpl$^+$ AML cells in PBS, respectively. Blood was drawn from the retro-orbital venous sinus to monitor the percentage of circulating c-Kit[30]/GFP$^+$ AML cells. After AML levels in blood exceeded 1% which corresponds to 10-20% of bone marrow-residing AML cells (Kuo), NSG and C57BL/6 mice were injected i.v. with various CpG-conjugates (5 mg/kg) every day or every other day, respectively, and euthanized a day after the last treatment.

Flow cytometry and Immunohistochemistry. Single cell suspensions were prepared by mechanic tissue disruption and collagenase D/DNase I treatment as described (Kortylewski et al. Nat. Med 2005). The AML cell percentages were determined by GFP and c-Kit expression. For extracellular staining, cells were incubated with fluorochrome-labeled Annexin V or antibodies to B220, CD3, CD11c, Gr1, F4/80, MHC class II, CD40, CD80, CD86, PDL1, CD3, CD4, CD8 or CD69 after anti-FcγIII/IIR blocking (eBioscience). For intracellular staining, cells were fixed/permeabilized and stained with antibodies to TLR9 (eBioscience), Stat3P or FoxP3 (BD) as described (Kortylewski et al. Nat. Med 2005). Fluorescence data were analyzed on a BD-AccuriC6 Flow Cytometer (BD) using FlowJo software (TreeStar). Immunohistochemical staining was performed on formalin-fixed/paraffin-embedded bone sections (5 μm) at the Pathology Core (COH).

Quantitative real-time PCR and protein assays. Total RNA isolation and cDNA synthesis were carried out as described previously (Zhang et al. Blood 2013). Western blot to detect STAT3, STAT3P and β-actin expression and EMSA assays to detect STAT3 binding to DNA were performed as described (Kortylewski et al. Nat. Biotech. 2009; Zhang et al. Blood 2013). Plasma cytokines were analyzed using Bio-Plex arrays (Bio-Rad) at the Clinical Immunobiology Core (COH).

Statistical analysis. One- or two-way analysis of variance plus Bonferroni posttest were applied to assess statistical significance of differences between multiple treatment groups or in tumor growth kinetics between treatment groups, respectively. Data were analyzed using GraphPad Prism vs4.0 software (GraphPad).

TABLE 2

Compound and component sequences.

| NAME | SEQUENCE (* = phosphorothioate linkage), x = (-(CH$_2$)$_3$-) bonded to phosphate groups at both ends except at the termini where terminal phosphates are optionally added and 5'x has an OH terminus and 3' x has a -C[6]-NH$_2$ bonded to the final phosphate group, other linkages are phosphodiester. | SEQ ID NO.: |
|---|---|---|
| CpG(A)-STAT3dODN | 5' G*G*TGCATCGATGCAGG*G*G*G*G-xxxxx-C*A*T*TTCCCGTAAATC-xxxx-GATTTACGGGAA*A*T*G-xxxxx 3' | 6 |
| GpC(A)-STAT3dODN | 5' G*G*TGCATGCATGCAG G*G*G*G*G-xxxxx-C*A*T*TTCCCGTAAATC-xxxx-GATTTACGGGAA*A*T*G-xxxxx 3' | 7 |
| CpG(A)-scrambled ODN | 5' G*G*TGCATCGATGCAGG*G*G*G*G-xxxxx-A*C*T*CTTGCCAATTAC-xxxx-GTAATTGGCAAG*A*G*T-xxxxx 3' | 8 |
| CpG(B)-STAT3dODN | 5' T*C*C*A*T*G*A*C*G*T*T*C*C*T*G*A*T*G*C*T-xxxxx-C*A*T*TTCCCGTAAATC-xxxx-GATTTACGGGAA*A*T*G-xxxxx 3' | 9 |

TABLE 2-continued

Compound and component sequences.

| NAME | SEQUENCE (* = phosphorothioate linkage), x = (-(CH$_2$)$_3$-) bonded to phosphate groups at both ends except at the termini where terminal phosphates are optionally added and 5'x has an OH terminus and 3' x has a -C$^6$-NH$_2$ bonded to the final phosphate group, other linkages are phosphodiester. | SEQ ID NO.: |
|---|---|---|
| CpG(B)-mutSTAT3dODN | 5' T*C*C*A*T*G*A*C*G*T*T*C*C*T*G*A*T*G*C*T-xxxxx-C*A*T*TTCCCTTAAATC-xxxx-GATTTAAGGGAA*A*T*G-xxxxx 3' | 10 |
| CpG(B)-scrambled ODN | 5' T*C*C*A*T*G*A*C*G*T*T*C*C*T*G*A*T*G*C*T-xxxxx-A*C*T*CTTGCCAATTAC-xxxx-GTAATTGGCAAG*A*G*T-xxxxx 3' | 11 |
| STAT3dODN | 5' xxxxx-C*A*T*TTCCCGTAAATC-xxxx-GATTTACGGGAA*A*T*G-xxxxx 3' | 12 |
| ODN 1585 | 5'-G*G*GGTCAACGTTGAG*G*G*G*G*G-3' or 5'-G*GGGTCAACGTTGAG*G*G*G*G*G-3' | 13 or 14 |
| ODN 2216 | 5'-G*G*GGGACGATCGTCG*G*G*G*G*G-3' or 5'-G*GGGACGATCGTCG*G*G*G*G*G-3' | 15 or 16 |
| ODN D19 | 5'-G*G*TGCATCGATGCAGG1*G*G*G*G-3' or 5'-G*GTGCATCGATGCAGG*G*G*G*G-3' | 17 or 18 |
| ODN 2336 | 5'-G*G*G*GACGACGTCGTGG*G*G*G*G*G-3' or 5'-G*G*GGACGACGTCGTGG*G*G*G*G*G-3' | 19 or 20 |
| ODN 1668 | 5'-T*C*C*A*T*G*A*C*G*T*T*C*C*T*G*A*T*G*C*T-3' | 21 |
| ODN 1826 | 5'-T*C*C*A*T*G*A*C*G*T*T*C*C*T*G*A*C*G*T*T-3' | 22 |
| ODN 2006 (ODN7909) | 5'-T*C*G*T*C*G*T*T*T*T*G*T*C*G*T*T*T*T*G*T*C*G*T*T-3' | 23 |
| ODN 2007 | 5'-T*C*G*T*C*G*T*T*G*T*C*G*T*T*T*T*G*T*C*G*T*T-3' | 24 |
| ODN 2395 | 5'-T*C*G*T*C*G*T*T*T*T*C*G*G*C*G*C*G*C*G*C*C*G-3' | 25 |
| ODN M362 | 5'-T*C*G*T*C*G*T*C*G*T*T*C*G*A*A*C*G*A*C*G*T*T*G*A*T-3' | 26 |

STAT3 is a transcription factor with crucial role in promoting tumor progression and immune evasion. To achieve STAT3 inhibition specifically in antigen-presenting cells (APCs), we linked STAT3 decoy oligodeoxynucleotides (STAT3dODN) to a TLR9 ligand, CpG ODN as successfully done before for delivery of siRNA molecules. The CpG-STAT3dODN conjugates are quickly internalized by both human and mouse TLR9-positive target cells such as dendritic cells (DCs), macrophages and B lymphocytes as well as by myeloid leukemia cells. After uptake, CpG-STAT3dODN molecules bind and sequester activated STAT3 proteins. The hairpin design and partial phosphorothioation of the backbone increases half-life of the CpG-STAT3dODN in human serum. Therefore, we assessed the feasibility of using CpG-STAT3dODNs for systemic administration against disseminated human TLR9+ acute myeloid leukemia (AML). As shown in xenotransplanted MV4-11 AML model repeated intravenous injections of CpG-STAT3dODN resulted in potent and direct antitumor effects effectively eliminating leukemic cells from all tested organs. The antitumor efficacy of this strategy is enhanced in immunocompetent mice. Systemic administration of CpG-STAT3dODN induced regression of the syngeneic mouse Cbfb/MYH11 leukemia within 12 days of treatment. The potent immune activation was associated with enhanced expression of antigen-presenting and co-stimulatory molecules not only on DCs but also on AML cells. These immunostimulatory effects correlated with activation and infiltration of CD8+ T cells into various organs with reduction in regulatory T cell numbers. Our findings highlight the potential of using CpGSTAT3dODN for the two-pronged TLR9/STAT3-targeted immunotherapy of human AML.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating lymphoma, leukemia, or prostate cancer in a patient in need thereof, the method comprising administering to the patient a therapeutically effective amount of a compound which comprises SEQ ID NO:23 covalently bonded to SEQ ID NO:12.

2. The method of claim 1 for treating leukemia.

3. The method of claim 2, wherein the leukemia is acute myeloid leukemia.

4. The method of claim 1, for treating lymphoma.

5. The method of claim 4, wherein the lymphoma is non-Hodgkin's lymphoma.

6. The method of claim 5, wherein the non-Hodgkin's lymphoma is a large cell lymphoma.

7. The method of claim 5, wherein the non-Hodgkin's lymphoma is Burkitt lymphoma or small cell lymphoma.

8. The method of claim 4, wherein the lymphoma is B cell lymphoma.

9. The method of claim 1, comprising systemically administering the compound to the patient.

10. The method of claim 1, comprising intravenously administering the compound to the patient.

11. The method of claim 1, comprising intratumorally administering the compound to the patient.

12. A method of treating lymphoma, leukemia, or prostate cancer in a patient in need thereof, the method comprising administering to the patient a therapeutically effective amount of a compound which comprises a toll-like receptor (TLR)-binding nucleic acid substituent conjugated to a signal transducer and activator of transcription (STAT)-binding nucleic acid substituent, wherein the STAT-binding nucleic acid substituent is capable of binding to a STAT transcription factor.

13. The method of claim 12 for treating leukemia.

14. The method of claim 13, wherein the leukemia is acute myeloid leukemia.

15. The method of claim 12, for treating lymphoma.

16. The method of claim 15, wherein the lymphoma is non-Hodgkin's lymphoma.

17. The method of claim 16, wherein-the TLR9-binding DNA substituent comprises a Class A CpG DNA sequence, a Class B CpG DNA sequence, or a Class C CpG DNA sequence.

18. The method of claim 12, wherein the toll-like receptor (TLR)-binding nucleic acid substituent is a toll-like receptor 9 (TLR9)-binding DNA substituent; and wherein the activator of transcription (STAT)-binding nucleic acid substituent is a signal transducer and activator of transcription 3 (STAT3)-binding DNA substituent.

19. The method of claim 12, wherein the TLR-binding nucleic acid substituent is a nucleic acid sequence comprising SEQ ID NO:21, SEQ ID NO:22, SEQ ID NO:23, or SEQ ID NO:24.

20. The method of claim 12, wherein the STAT3-binding DNA substituent comprises a first STAT3-binding DNA sequence covalently bound to a second STAT3-binding DNA sequence by a spacer; and the spacer is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

* * * * *